US006020371A

United States Patent [19]
Dragovich et al.

[11] Patent Number: 6,020,371
[45] Date of Patent: Feb. 1, 2000

[54] ANTIPICORNAVIRAL COMPOUNDS COMPOSITIONS CONTAINING THEM AND METHODS FOR THEIR USE

[75] Inventors: Peter S. Dragovich, Encinitas; Thomas J. Prins, Cardiff; Ru Zhou, Carlsbad, all of Calif.

[73] Assignee: Agouron Pharmaceuticals, Inc., La Jolla, Calif.

[21] Appl. No.: 08/991,282

[22] Filed: Dec. 16, 1997

Related U.S. Application Data

[60] Provisional application No. 60/041,749, Mar. 28, 1997.

[51] Int. Cl.$^7$ ...................... A61K 31/215; C07C 299/02
[52] U.S. Cl. ...................... 514/514; 560/155; 560/19; 546/329; 548/248; 548/329; 549/22; 549/39; 514/351; 514/378; 514/423; 514/436
[58] Field of Search .................................. 560/41, 9, 19, 560/155; 514/532, 514, 351, 378, 423, 436, 440; 546/329; 548/248, 530; 549/22, 39

[56] References Cited

U.S. PATENT DOCUMENTS 5,344,957  9/1994  Bovy et al. ............................... 560/35

FOREIGN PATENT DOCUMENTS

| 0 201 844 | 11/1986 | European Pat. Off. . |
|---|---|---|
| 632051 | 1/1995 | European Pat. Off. . |
| WO92/22570 | 12/1992 | WIPO . |
| WO95/23222 | 8/1995 | WIPO . |
| WO95/31433 | 11/1995 | WIPO . |

OTHER PUBLICATIONS

Hanzlik et al., "Vinylogous Amino Acid Esters: A New Class of Inactivators for Thiol Proteases," *J. Med. Chem.*, vol. 27, No. 6, Jun. 1984, pp. 711–712.

Thompson et al., "Carboxyl–Modified Amino Acids and Peptides as Protease Inhibitors," *J. Med. Chem.*, vol. 29, No. 1, 1986, pp. 104–111.

Liu et al., "Structure–Activity Relationships for Inhibition of Papain by Peptide Michael Acceptors," *J. Med. Chem.*, vol. 35, 1992, pp. 1067–1075.

White et al., *Principles of Biochemistry*, 6th Ed., McGraw Hill, 1978, pp. 893–895.

Callahan et al., "Molecular cloning and complete sequence determination of RNA genome of human rhinovirus type 14," *Proc. Natl. Acad. Sci. USA*, vol. 82, Feb. 1985, pp. 732–736.

Olson et al., "Structure of a human rhinovirus complexed with its receptor molecule," *Proc. Natl. Acad. Sci. USA*, vol. 90, Jan. 1993, pp. 507–511.

Hammerle et al., "Site–directed Mutagenesis of the Putative Catalytic Triad of Poliovirus 3C Proteinase," *J. Biol. Chem.*, vol. 266, No. 9, 1991, pp. 5412–5416.

Orr et al., "Hydrolysis of a Series of Synthetic Peptide Substrates by the Human Rhinovirus 14 3C Proteinase, Cloned and Expressed in *Escherichia coli*," *J. Gen. Virol*, vol. 70, 1989, pp. 2931–2942.

Leong et al., "Human Rhinovirus–14 Protease 3C (3C$^{pro}$) Binds Specifically to the 5'–Noncoding Region of the Viral RNA," *J. Biol. Chem.*, vol. 268, 1993, pp. 25735–25739.

*Comprehensive Medicinal Chem.*, vol. 2, C. Hansch, Eds., Pergamon Press, Oxford, 1990, pp. 431–433, 440–441.

Shaw, "Cysteinyl Proteinases and Their Selective Inactivation," *Advance Enz*, vol. 63, 1990, pp. 271–347.

Matthews et al., "Structure of Human Rhinovirus 3C Protease Reveals a Trypsin–like Polypeptide Fold, RNA–Binding Site, and Means for Cleaving Precursor Polyprotein," *Cell*, vol. 77, Jun. 1994, pp. 761–771.

Allaire et al., "Picornaviral 3C cysteine proteinases have a fold similar to chymotrypsin–like serine proteinases," *Nature*, vol. 369, May 1994, pp. 72–76.

Bazan et al., "Viral cysteine proteases are homologous to the trypsin–like family of serine proteases: Structural and functional implications," *Proc. Natl. Acad. Sci. USA*, vol. 85, Nov. 1988, pp. 7872–7876.

Cordingley et al., "Cleavage of Small Peptides In Vitro by Human Rhinovirus 14 3C Protease Expressed in *Escherichia coli*," *Journal of Virology*, vol. 63, No. 12, Dec. 1989, pp. 5037–5045.

Kaldor et al,. "Glutamine–Derived Aldehydes for the Inhibition of Human Rhinovirus 3C Protease," *Bioorganic & Medicinal Chemistry Letters*, vol. 5, No. 17, 1995, pp. 2021–2026.

Malcolm et al., "Peptide Aldehyde Inhibitors of Hepatitis A Virus 3C Proteinase," *Biochemistry*, vol. 34, 1995, pp. 8172–8179.

Skiles et al., "Spiro Indolinone Beta–Lactams, Inhibitors of Poliovirus and Rhinovirus 3C–Proteinases," *Tetrahedron Letters*, vol. 31, No. 50, 1990, pp. 7277–7280.

Singh et al., "Structure and Stereochemistry of Thysanone; A Novel Human Rhinovirus 3C–Protease Inhibitor from *Thysanophora penicilloides*," *Tetrahedron Letters*, vol. 32, No. 39, 1991, pp. 5279–5282.

Kadam et al., "Citrinin Hydrate and Radicinin: Human Rhinovirus 3C–Protease Inhibitors Discovered in a Target–Directed Microbial Screen," *The Journal of Antibiotics*, vol. 47, No. 7, Jul. 1994, pp. 836–839.

Palmer et al., "Vinyl Sulfones as Mechanism–Based Cysteine Protease Inhibitors," *J. Med. Chem.*, vol. 38, 1995, pp. 3913–3196.

Maryanoff et al., "Molecular basis for the inhibition of human α–thrombin by the macrocylic peptide cyclotheonamide A," *Proc. Natl. Acad. Sci. USA*. vol. 90, Sep. 1993, pp. 8048–8052.

Rich et al., "Synthesis of Analogues of the Carboxyl Protease Inhibitor Pepstatin. Effect of Structure on Inhibition of Pepsin and Renin," *J. Med. Chem.*, vol. 23, 1980, pp. 27–33.

(List continued on next page.)

*Primary Examiner*—John Kight
*Assistant Examiner*—Charanjit S. Aulakh
*Attorney, Agent, or Firm*—Fitzpatrick, Cella, Harper & Scinto

[57] ABSTRACT

Picornaviral 3C protease inhibitors, obtainable by chemical synthesis, inhibit or block the biological activity of the picornaviral 3C protease. These compounds, as well as pharmaceutical compositions that contain these compounds, are suitable for treating patients or hosts infected with one or more picornaviruses.

38 Claims, No Drawings

OTHER PUBLICATIONS

Hagihara et al., "Reassignment of Stereochemistry and Total Synthesis of the Thrombin Inhibitor Cyclotheonamide B," *J. Am. Chem. Soc.*, vol. 114, 1992, pp. 6570–6571.

Haberson et al., "Inhibition of Aminopeptidases by Peptides Containing Ketomethylene and Hydroxyethylene Amide Bond Replacements," *J. Med. Chem.*, vol. 32, 1989, pp. 1378–1392.

Barton et al., "Synthesis of Novel α–Amino–Acids and Derivatives Using Radical Chemistry: Synthesis of L– and D–α–Amino–Adipic Acids, L–α–Aminopimelic Acid and Appropriate Unsaturated Derivatives," *Tetrahedron*, vol. 43, No. 19, 1987, pp. 4297–4308.

Smith et al., "Synthesis and Renin Inhibitory Activity of Angioitensinogen Analogues Having Dehydrostatine, LeuΨ[$CH_2S$]Val, or LeuΨ[$CH_2SO$]Val at the $P_1$–$P_1'$ Cleavage Site", *J. Med. Chem.*, vol. 31, 1988, pp. 1377–1382.

Meng et al., "Synthetic Approaches toward Glidobamine, the Core Structure of the Glidobactin Antibiotics," *Tetrahedron*, vol. 47, No. 32, 1991, pp. 6251–6264.

Kolter et al., "Configuratively Stable Dipeptide Aldehydes from D–Glucosamine Hydrochloride," *Angew. Chem. Int. Ed. Engl.*, vol. 31, No. 10, 1992, pp. 1391–1392.

Reetz et al., "Stereoselective Nucleophilic Addition Reactions of Reactive Pseudopeptides," *Angew. Chem. Int. Ed. Engl.*, vol. 31, No. 12, 1992, pp. 1626–1629.

Aoyagi et al., "Structures and Activities of Protease Inhibitors of Microbial Origin," Institute of Microbial Chemistry, Tokyo, Japan, 1975, pp. 429–454.

Rich, "Inhibitors of cysteine proteinases," *Proteinase Inhibitors*, Barrett and Salvesen (eds.), Elsevier Science Publishers BV, 1986, pp. 154–178.

Herold et al., "A Versatile and Stereocontrolled Synthesis of Hydroxyethylene Dipeptide Isosteres," *J. Org. Chem.*, vol. 54 (1989), pp. 1178–1185.

Bradbury et al., "An Efficient Synthesis of the γ–Lactone Corresponding to a Hydroxyethylene Dipeptide Isostere Using Stereoselective Bromolactonisation of a Chiral Acyloxazolidinone," *Tetrahedron Letters*, vol. 30, No. 29 (1989), pp. 3845–3848.

Bradbury et al., "1,2,4–Triazolo[4,3–a]pyrazine Derivatives with Human Renin Inhibitory Activity," *J. Med. Chem.*, vol. 33 (1990), pp. 2335–2342.

Wuts et al., "Synthesis of the Hydroxyethylene Isostere of Leu–Val," *J. Org. Chem.*, vol. 57 (1992), pp. 6696–6700.

Jones et al., "A Short Stereocontrolled Synthesis of Hydroxyethylene Dipeptide Isosteres," *J. Org. Chem.*, vol. 58 (1993), pp. 2286–2290.

Pégorier et al., "A General Stereocontrolled Synthesis of Hydroxyethylene Dipeptide Isosteres," *Tetrahedron Letters*, vol. 36, No. 16 (1995), pp. 2753–2756.

Dondoni et al., "Thiazole–Based Stereoselective Routes to Leucine and Phenylalanine Hydroxyethylene Dipeptide Isostere Inhibitors of Renin and HIV–1 Aspartic Protease," *J. Org. Chem.*, vol. 60 (1995), pp. 7927–7933.

Weislow et al., "New Soluble–Formazan Assay for HIV–1 Cytopathic Effects: Application to High–Flux Screening of Synthetic and Natural Products for AIDS–Antiviral Activity," *Journal of the National Cancer Institute*, vol. 81, No. 8 (1989), pp. 577–586.

L.A. Carpino, "1–Hydroxy–7–Azabenzotriazole. An Efficient Peptide Coupling Additive," *Journal of the American Chemical Society*, vol. 115, No. 10 (1993), pp. 4397–4398.

J.E. Baldwin, et al., "An Intramolecular Cobalt Cyclisation for the Construction of Substituted Pyrrolidines," *Tetrahedron*, vol. 48, No. 42 (1992), pp. 9373–9384.

J.J. Willard, et al., "New Method of Removing Xanthate Groups from Carbohydrates. Chemical Structure of Methyl α–D–Glucopyranoside Monoxanthate," *Journal of the American Chemical Society*, vol. 82, No. 16 (1960), pp. 4347–4350.

R.M. Freidinger, et al., "Synthesis of 9–Fluorenylmethyloxycarbonyl–Protected N–Alkyl Amino Acids by Reduction of Oxazolidinones," *Journal of Organic Chemistry*, vol. 48, No. 4 (1983), pp. 77–81.

D.A. Niederer, et al., "Amination with N–Benzyloxycarbonyl–3–Phenyloxaziridine as a Route to Sensitive Chiral α–Hydrazino Acids: Synthesis of L–Hydrazino Serine," *Tetrahedron Letters*, vol. 34, No. 43 (1993), pp. 6859–6862.

C.A. Veale, et al., "Nonpeptidic Inhibitors of Human Leukocyte Elastase. 5. Design, Synthesis, and X–ray Crystallography of a Series of Orally Active 5–Aminopyrimidin–6–one–Containing Trifluoromethyl Ketones," *Journal of Medicinal Chemistry*, vol. 38, No. 1 (1995), pp. 98–108.

R.V. Hoffman, et al., "A Simple, Stereoselective Synthesis of Ketomethylene Dipeptide Isosteres," *Tetrahedron*, vol. 53, No. 21 (1997), pp. 7119–7126.

D. Askin, et al., "Highly Diastereoselective Alkylations of Chiral Amide Enolates: New Routes to Hydroxyethylene Dipeptide Isostere Inhibitors of HIV–1 Protease," *Journal of Organic Chemistry*, vol. 57, No. 10 (1992), pp. 2771–2773.

J.C. McWilliams, et al., "Tandem Asymmetric Transformations: An Asymmetric 1,2–Migration from a Higher Order Zincate Coupled with a Stereoselective Homoaldol Reaction," *Journal of the American Chemical Society*, vol. 118, No. 47 (1996), pp. 11970–11971.

J.R. Luly, et al., "A Synthesis of Protected Aminoalkyl Epoxides from α–Amino Acids," *Journal of Organic Chemistry*, vol. 52, No. 8 (1987), pp. 1487–1492.

Mar., *Advanced Organic Chemistry*, Fourth Edition, John Wiley & Sons, Inc. (New York), 1992, pp. 205, 351–356, 642–643, 647, 652–653, 666, 501, 520–521, 569, 579–580, 992–994, 999–1000, 1005, and 1008.

H. Ikuta, et al., "Synthesis and Antiinflammatory Activities of 3–(3,5–Di–tert–butyl–4–hydroxybenzylidene)pyrrolidin–2–ones," *Journal of Medicinal Chemistry*, vol. 30, No. 11 (1987), pp. 1995–1998.

Shcherbina, et al., *Chemical Abstract* No. 68:69376 (1968).

Venkatramam, et al., "Synthesis of Potential Inhibitors for Human Rhinovirus 3 C Protease," *The Second Winter Conference on Medicinal and Bioorganic Chemistry*, Steamboat Springs, Colorado, Jan. 26–31, 1997.

Hellen, et al., "Proteolytic Processing of Polyproteins in the Replication of RNA Viruses," *Biochemistry*, vol. 28, No. 26 (1989), pp. 9881–9890.

Matthews, et al., "Structure of Human Rhinovirus 3C Protease Reveals a Trypsin–like Polypeptide Fold, RNA–Binding Site, and Means for Cleaving Precursor Polyprotein," *Cell*, vol. 77, No. 5 (1994), pp. 761–771.

Cordingley, et al., Substrate Requirements of Human Rhinovirus 3C Protease for Peptide Cleavage in Vitro, *The Journal of Biological Chemistry*, vol. 265, No. 16 (1990), pp. 9062–9065.

Wellink, et al., "Proteases Involved in the Processing of Viral Polyproteins," *Archives of Virology*, vol. 98 (1988), pp. 1–26.

Vagner, J. et al.: Solid–phase organic synthesis: Creation of carbon–carbon double bonds under mild conditions by wittig–type reactions. Collect. Czech. Chem. Commun. vol. 61, pp. 1697–1702.

P. Wipf et al., "$S_n$ 2 '— Reactions of Peptide Aziridines. A Cuprate—Based Approach to (E)—Alkene Isosteres", *Journal of Organic Chemistry,* vol. 59, No. 17, Aug. 26, 1994, pp. 4875–4886.

N. Moss et al., "Peptidomimetic Inhibitors of Herpes Simplex Virus Ribonucleotide reductase with Improved *in Vivo* Antivity", *Journal of Medicinal Chemistry,* vol. 39, 1996. pp. 4173–4180.

ANTIPICORNAVIRAL COMPOUNDS COMPOSITIONS CONTAINING THEM AND METHODS FOR THEIR USE

RELATED APPLICATION DATA

This application claims priority benefits under 35 U.S.C. § 119 based on U.S. Provisional Patent Appln. No. 60/041,749, filed Mar. 28, 1997.

Additionally, this application relates to U.S. patent application Ser. No. 08/850,398, filed May 2, 1997, and U.S. Provisional Patent Appln. No. 60/046,204, filed May 12, 1997. Each of these U.S. patent applications relates to antipicornaviral compounds, compositions containing them, and methods for their production and use. Each of these applications also is entirely incorporated herein by reference. This application also relates to a concurrently filed U.S. patent application entitled "Antipicornaviral Compounds and Methods for Their Use and Preparation," U.S. patent application Ser. No. 08/991,739, filed in the names of inventors Stephen E. Webber, Peter S. Dragovich, Thomas J. Prins, Ethel S. Littlefield, Joseph T. Marakovits, and Robert E. Babine. This concurrently filed application also is entirely incorporated herein by reference.

BACKGROUND OF THE INVENTION

The invention pertains to the discovery and use of new compounds that inhibit the enzymatic activity of picornaviral 3C proteases, specifically rhinovirus proteases (RVPs), as well as retard viral growth in cell culture.

The picornaviruses are a family of tiny non-enveloped positive stranded RNA containing viruses that infect humans and other animals. These viruses include the human rhinoviruses, human polioviruses, human coxsackieviruses, human echoviruses, human and bovine enteroviruses, encephalomyocarditis viruses, menigovirus, foot and mouth viruses, hepatitis A virus and others. The human rhinoviruses are a major cause the common cold. To date, there are no effective therapies to cure the common cold, only treatments that relieve the symptoms.

Picornaviral infections may be treated by inhibiting the proteolytic 3C enzymes. These enzymes are required for the natural maturation of the picornaviruses. They are responsible for the auto catalytic cleavage of the genomic, large polyprotein into the essential viral proteins. Members of the 3C protease family are cysteine proteases, where the sulfhydryl group most often cleaves the glutamine-glycine amide bond. Inhibition of 3C proteases is believed to block proteolytic cleavage of the polyprotein, which in turn can retard the maturation and replication of the viruses by interfering with viral particle production. Therefore, inhibiting the processing of this cysteine protease with selective, small molecules that are specifically recognized should represent an important and useful approach to treat and cure viral infections of this nature and, in particular, the common cold.

SUMMARY OF THE INVENTION

The present invention is directed to compounds that function as picornaviral 3C protease inhibitors, particularly those that have antiviral activity. It is further directed to the use of such 3C protease inhibitors. The Inventors demonstrate the compounds of the present invention bind to rhinovirus 3C proteases and preferably have antiviral cell culture activity. The enzymatic inhibition assays used reveal that these compounds can bind irreversibly, and the cell culture assays demonstrate that these compounds can possess antiviral activity.

The present invention is directed to compounds of the formula (I):

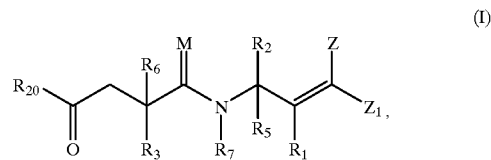

wherein:

M is O or S;

$R_1$ is H, F, an alkyl group, OH, SH, or an O-alkyl group;

$R_2$ and $R_5$ are independently selected from H,

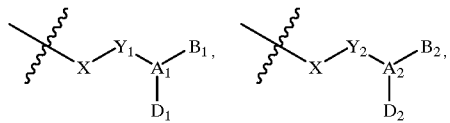

or an alkyl group, wherein the alkyl group is different from

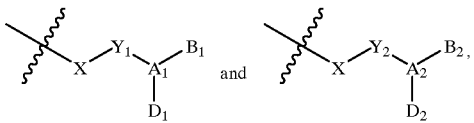

with the proviso that at least one of $R_2$ or $R_5$ must be

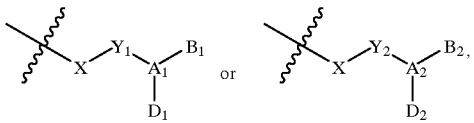

and wherein, when $R_2$ or $R_5$ is

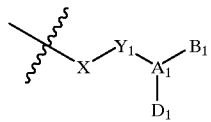

is =CH or =CF and $Y_1$ is =CH or =CF, or X and $Y_1$ together with Q' form a three-membered ring in which Q' is —C($R_{10}$)($R_{11}$)— or —O—, X is —CH— or —CF—, and $Y_1$ is —CH—, —CF—, or —C(alkyl)—, where $R_{10}$ and $R_{11}$ independently are H, a halogen, or an alkyl group, or, together with the carbon atom to which they are attached, form a cycloalkyl group or a heterocycloalkyl group, or X is —CH$_2$—, —CF$_2$—, —CHF—, or —S—, and $Y_1$ is —O—, —S—, —NR$_{12}$—, —C($R_{13}$)($R_{14}$)—, —C(O)—, —C(S)—, or —C(CR$_{13}R_{14}$)—, wherein $R_{12}$ is H or alkyl, and $R_{13}$ and $R_{14}$ independently are H, F, or an alkyl group, or, together with the atoms to which they are bonded, form a cycloalkyl group or a heterocycloalkyl group;

$A_1$ is C, CH, CF, S, P, Se, N, NR$_{15}$, S(O), Se(O), P—OR$_{15}$, or P—NR$_{15}R_{16}$, wherein $R_{15}$ and $R_{16}$ independently are an alkyl group, a cycloalkyl group, a heterocycloalkyl group, an aryl group, or a heteroaryl group, or, together with the atom to which they are bonded, form a heterocycloalkyl group;

$D_1$ is a moiety with a lone pair of electrons capable of forming a hydrogen bond; and $B_1$ is H, F, an alkyl group, a cycloalkyl group, a heterocycloalkyl group, an aryl group, a heteroaryl group, —$OR_{17}$, —$SR_{17}$, —$NR_{17}R_{18}$, —$NR_{19}NR_{17}R_{18}$, or —$NR_{17}OR_{18}$, wherein $R_{17}$, $R_{18}$, and $R_{19}$ independently are H, an alkyl group, a cycloalkyl group, a heterocycloalkyl group, an aryl group, a heteroaryl group, or an acyl group;

and with the provisos that when $D_1$ is the moiety ≡N with a lone pair of electrons capable of forming a hydrogen bond, $B_1$ does not exist; and when $A_1$ is an $sp^3$ carbon, $B_1$ is not —$NR_{17}R_{18}$ when $D_1$ is the moiety —$NR_{25}R_{26}$ with a lone pair of electrons capable of forming a hydrogen bond, wherein $R_{25}$ and $R_{26}$ are independently H, an alkyl group, a cycloalkyl group, a heterocycloalkyl group, an aryl group, or a heteroaryl group; and wherein $D_1$—$A_1$—$B_1$ optionally forms a nitro group where $A_1$ is N; and further wherein, when $R_2$ or $R_5$ is

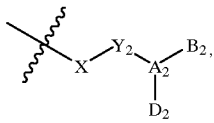

X is =CH or =CF and $Y_2$ is =C, =CH, or =CF, or X and $Y_2$ together with Q' form a three-membered ring in which Q' is —$C(R_{10})(R_{11})$— or —O—, X is —CH— or —CF—, and $Y_2$ is —CH—, —CF—, or —C(alkyl)—, where $R_{10}$ and $R_{11}$ independently are H, a halogen, or an alkyl group, or, together with the carbon atom to which they are attached, form a cycloalkyl group or a heterocycloalkyl group, or X is —$CH_2$—, —$CF_2$—, —CHF—, or —S—, and $Y_2$ is —O—, —S—, —$N(R'_{12})$—, —C(O)—, —$C(R'_{13})(R'_{14})$—, —C(S)—, or —$C(CR'_{13}R'_{14})$—, wherein $R'_{12}$ is H, an alkyl group, a cycloalkyl group, a heterocycloalkyl group, an aryl group, a heteroaryl group, —$OR'_{13}$, —$NR'_{13}R'_{14}$, —C(O)—$R'_{13}$, —$SO_2R'_{13}$, or —$C(S)R'_{13}$, and $R'_{13}$ and $R'_{14}$, independently are H, F, or an alkyl group, a cycloalkyl group, or, together with the atom to which they are attached, form a cycloalkyl group or a heterocycloalkyl group;

$A_2$ is C, CH, CF, S, P, Se, N, $NR_{15}$, S(O), Se(O), P—$OR_{15}$, or P—$NR_{15}R_{16}$, wherein $R_{15}$ and $R_{16}$ independently are an alkyl group, a cycloalkyl group, a heterocycloalkyl group, an aryl group, or a heteroaryl group or, together with the atom to which they are bonded, form a heterocycloalkyl group;

$D_2$ is a moiety with a lone pair of electrons capable of forming a hydrogen bond; and $B_2$ is H, F, an alkyl group, a cycloalkyl group, a heterocycloalkyl group, an aryl group, a heteroaryl group, —$OR_{17}$, —$SR_{14}$, —$NR_{17}R_{18}$, —$NR_{19}NR_{17}R_{18}$, or —$NR_{17}OR_{18}$, wherein $R_{17}$, $R_{18}$, and $R_{19}$ independently are H, an alkyl group, a cycloalkyl group, a heterocycloalkyl group, an aryl group, a heteroaryl group, or an acyl group;

and further wherein any combination of $Y_2$, $A_2$, $B_2$, and $D_2$ forms a cycloalkyl group, a heterocycloalkyl group, an aryl group, or a heteroaryl group;

$R_3$ and $R_6$ are independently H, F, an alkyl group, a cycloalkyl group, a heterocycloalkyl group, an aryl group, a heteroaryl group, —$C(O)R_{17}$, —$OR_{17}$, —$SR_{17}$, —$NR_{17}R_{18}$, —$NR_{19}NR_{17}R_{18}$, or —$NR_{17}OR_{18}$, wherein $R_{17}$, $R_{18}$, and $R_{19}$ independently are H, an alkyl group, a cycloalkyl group, a heterocycloalkyl group, an aryl group, a heteroaryl group, or an acyl group; or, $R_3$ and $R_6$, together with the carbon atom to which they are attached, form a cycloalkyl group or a heterocycloalkyl group;

$R_7$ is H, an alkyl group, a cycloalkyl group, a heterocycloalkyl group, a heteroaryl group, —$OR_{17}$, —$SR_{17}$, —$NR_{17}R_{18}$, —$NR_{19}NR_{17}R_{18}$, or —$NR_{17}OR_{18}$, wherein $R_{17}$, $R_{18}$, and $R_{19}$ independently are H, an alkyl group, a cycloalkyl group, a heterocycloalkyl group, an aryl group, a heteroaryl group, or an acyl group;

or $R_7$, together with $R_3$ or $R_6$ and the atoms to which they are attached, form a heterocycloalkyl group;

$R_{20}$ is H, OH, or any suitable organic moiety; and Z and $Z_1$ are independently H, F, an alkyl group, a cycloalkyl group, a heterocycloalkyl group, an aryl group, a heteroaryl group, —$C(O)R_{21}$, —$CO_2R_{21}$, —CN, —$C(O)NR_{21}R_{22}$, —$C(O)NR_{21}OR_{22}$, —$C(S)R_{21}$, —$C(S)NR_{21}R_{22}$, —$NO_2$, —$SOR_{21}$, —$SO_2R_{21}$, —$SO_2NR_{21}R_{22}$, —$SO(NR_{21})(OR_{22})$, —$SONR_{21}$, —$SO_3R_{21}$, —$PO(OR_{21})_2$, —$PO(R_{21})(R_{22})$, —$PO(NR_{21}R_{22})(OR_{23})$, —$PO(NR_{21}R_{22})(NR_{23}R_{24})$, —$C(O)NR_{21}NR_{22}R_{23}$, or —$C(S)NR_{21}NR_{22}R_{23}$, wherein $R_{21}$, $R_{22}$, $R_{23}$, and $R_{24}$ are independently H, an alkyl group, a cycloalkyl group, a heterocycloalkyl group, an aryl group, a heteroaryl group, an acyl group, or a thioacyl group, or wherein any two of $R_{21}$, $R_{22}$, $R_{23}$, and $R_{24}$, together with the atom(s) to which they are bonded, form a heterocycloalkyl group; or $Z_1$, as defined above, together with $R_1$, as defined above, and the atoms to which $Z_1$ and $R_1$ are bonded, form a cycloalkyl or heterocycloalkyl group, or Z and $Z_1$, both as defined above, together with the atoms to which they are bonded, form a cycloalkyl or heterocycloalkyl group;

and pharmaceutically acceptable prodrugs, salts, active metabolites, and solvates thereof, and wherein these compounds, pharmaceutically acceptable prodrugs, salts, active metabolites, and solvates preferably have antipicornaviral activity with an $EC_{50}$ less than or equal to 10 μM in the HI-HeLa cell culture assay, and more preferably antirhinoviral activity with an $EC_{50}$ less than or equal to 10 μM in the HI-HeLa cell culture assay and/or anticoxsachieviral activity with an $EC_{50}$ less than or equal to 10 μM in the HI-HeLa cell culture assay.

DETAILED DESCRIPTION OF THE INVENTION

The present invention relates to compounds of the formula I:

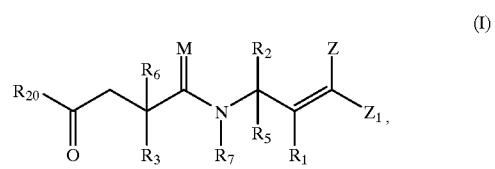

wherein $R_1$, $R_2$, $R_3$, $R_5$, $R_6$, $R_7$, $R_{20}$, M, Z, and $Z_1$ are as defined above, and to the pharmaceutically acceptable prodrugs, salts, active metabolites, and solvates thereof, where these compounds, pharmaceutically acceptable prodrugs, salts, active metabolites, and solvates preferably have antipicornaviral activity with an $EC_{50}$ less than or equal to 10 μM in the HI-HeLa cell culture assay, and more preferably antirhinoviral activity with an $EC_{50}$ less than or equal to 10 μM in the HI-HeLa cell culture assay and/or anticoxsachieviral activity with an $EC_{50}$ less than or equal to 10 μM in the HI-HeLa cell culture assay.

The present invention preferably relates to compounds of the formula X:

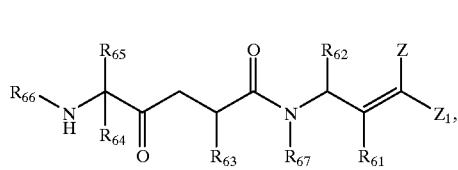

wherein:

$R_{61}$ is H, F, or an alkyl group;

$R_{62}$ is selected from one of the following moieties:

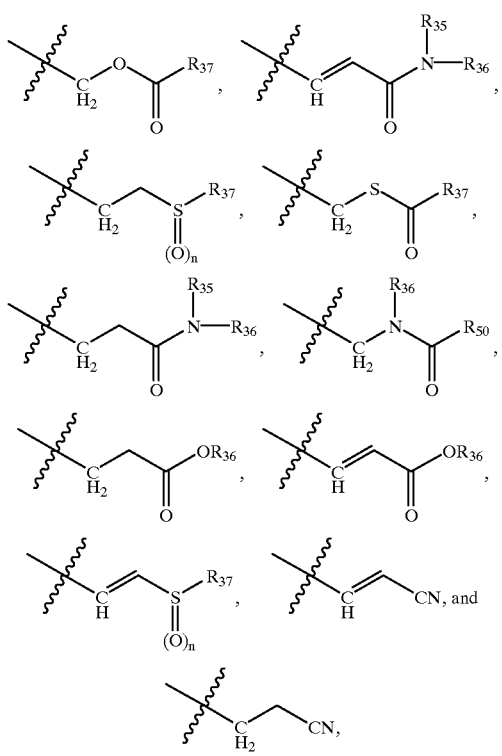

wherein:

$R_{35}$ is H, an alkyl group, an aryl group, —$OR_{38}$, or —$NR_{38}R_{39}$, wherein $R_{38}$ and $R_{39}$ independently are H, an alkyl group, a cycloalkyl group, a heterocycloalkyl group, an aryl group, a heteroaryl group, or an acyl group; and $R_{36}$ is H or an alkyl group, or $R_{35}$ and $R_{36}$, together with the nitrogen atom to which they are attached, form a heterocycloalkyl group or a heteroaryl group;

$R_{37}$ is an alkyl group, an aryl group, or —$NR_{38}R_{39}$, wherein $R_{38}$ and $R_{39}$ are as defined above;

$R_{50}$ is H, an alkyl group, an aryl group, —$OR_{38}$, —$SR_{39}$, —$NR_{38}R_{39}$, —$NR_{40}NR_{38}R_{39}$, or —$NR_{38}OR_{39}$, or $R_{50}$ and $R_{36}$, together with the atoms to which they are attached, form a heterocycloalkyl group;

wherein $R_{38}$ and $R_{39}$ are as defined above and $R_{40}$ is H, an alkyl group, a cycloalkyl group, a heterocycloalkyl group, an aryl group, a heteroaryl group, or an acyl group; and n is 0, 1, or 2;

$R_{63}$ is H or an alkyl group;

$R_{64}$ is H, an alkyl group, a cycloalkyl group, a heterocycloalkyl group, an aryl group, or a heteroaryl group;

$R_{65}$ is H or an alkyl group;

$R_{66}$ is H, an acyl group, an alkyl group, a cycloalkyl group, a heterocycloalkyl group, an aryl group, a sulfonyl group, or a heteroaryl group;

$R_{67}$ is H or an alkyl group; and

Z and $Z_1$ are independently H, F, an alkyl group, a cycloalkyl group, heterocycloalkyl group, an aryl group, a heteroaryl group, —$C(O)R_{21}$, —$CO_2R_{21}$, —CN, —$C(O)NR_{21}R_{22}$, —$C(O)NR_{21}OR_{22}$, —$C(S)R_{21}$, —$C(S)NR_{21}R_{22}$, —$NO_2$, —$SOR_{21}$, —$SO_2R_{21}$, —$SO_2NR_{21}R_{22}$, —$SO(NR_{21})(OR_{22})$, —$SONR_{21}$, —$SO_3R_{21}$, —$PO(OR_{21})_2$, —$PO(R_{21})(R_{22})$, —$PO(NR_{21}R_{22})OR_{23})$, —$PO(NR_{21}R_{22})(NR_{23}R_{24})$, —$C(O)NR_{21}NR_{22}R_{23}$, or —$C(S)NR_{21}NR_{22}R_{23}$, wherein $R_{21}$, $R_{22}$, $R_{23}$, and $R_{24}$ are independently H, an alkyl group, a cycloalkyl group, a heterocycloalkyl group, an aryl group, a heteroaryl group, an acyl group, or a thioacyl group, or wherein any two of $R_{21}$, $R_{22}$, $R_{23}$, and $R_{24}$, together with the atom(s) to which they are bonded, form a heterocycloalkyl group, or Z and $Z_1$, both as defined above, together with the atoms to which they are attached, form a heterocycloalkyl group; and pharmaceutically acceptable prodrugs, salts, active metabolites, and solvates thereof.

As used in the preset application, the following definitions apply:

An "alkyl group" is intended to mean a straight or branched chain monovalent radical of saturated and/or unsaturated carbon atoms and hydrogen atoms, such as methyl, ethyl, propyl, isopropyl, butyl, isobutyl, t-butyl, ethenyl, pentenyl, butenyl, propenyl, ethynyl, butynyl, propynyl, pentynl, hexynyl, and the like, which may be unsubstituted (i.e., containing only carbon and hydrogen) or substituted by one or more suitable substituents as defined below.

A "cycloalkyl group" is intended to mean a non-aromatic, monovalent monocyclic, bicyclic, or tricyclic radical containing 3, 4, 5, 6, 7, 8, 9, 10, 11, 12, 13, or 14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more suitable substituents.

Illustrative examples of cycloalkyl groups include, but are not limited to, the following moieties:

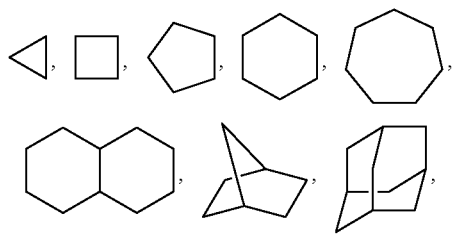

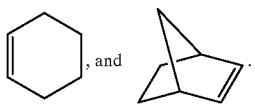

A "heterocycloalkyl group" is intended to mean a non-aromatic, monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, and which includes 1, 2, 3, 4, or 5 heteroatoms selected from nitrogen, oxygen, and sulfur, wherein the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include, but are not limited to the following moieties:

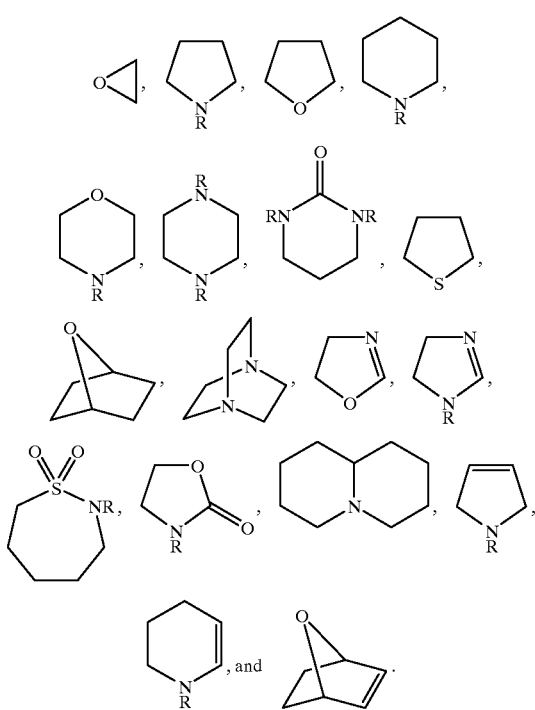

An "aryl group" is intended to mean an aromatic, monovalent monocyclic, bicyclic, or tricyclic radical containing 6, 10, 14, 18 carbon ring atoms, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Illustrative examples of aryl groups include, but are not limited to, the following moieties:

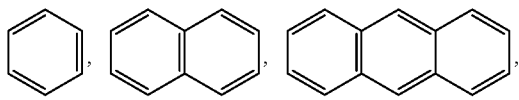

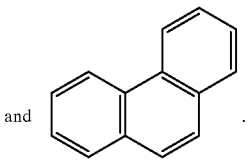

A "heteroaryl group" is intended to mean an aromatic monovalent monocyclic, bicyclic, or tricyclic radical containing 4, 5, 6, 7, 8, 9, 10, 11, 12, 13, 14, 15, 16, 17, or 18 ring atoms, including 1, 2, 3, 4, or 5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include, but are not limited to, the following moieties:

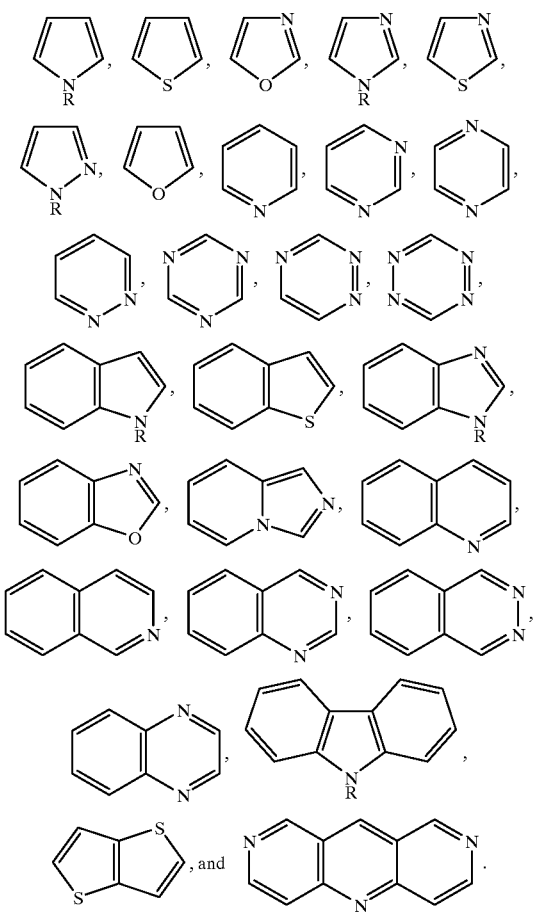

An "acyl group" is intended to mean a —C(O)—R radical, wherein R is any suitable substituent as defined below.

A "thioacyl group" is intended to mean a —C(S)—R radical, wherein R is any suitable substituent as defined below.

A "sulfonyl group" is intended to mean a —SO$_2$R radical, wherein R is any suitable substituent as defined below.

The term "suitable substituent" is intended to mean any of the substituents recognizable, such as by routine testing, to those skilled in the art as not adversely affecting the inhibitory activity of the inventive compounds. Illustrative examples of suitable substituents include, but are not limited to, hydroxy groups, oxo groups, alkyl groups, acyl groups, sulfonyl groups, mercapto groups, alkylthio groups, alkoxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroaryloxy groups, arylthio groups, heteroarylthio groups, and the like.

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxy groups, alkyl groups, oxo groups, cycloalkyl groups, heterocycloalkyl groups, aryl groups, heteroaryl groups, acyl groups, sulfonyl groups, mercapto groups, alkylthio groups, alkoxy groups, carboxy groups, amino groups, alkylamino groups, dialkylamino groups, carbamoyl groups, arylthio groups, heteroarylthio groups, and the like.

A "hydroxy group" is intended to mean the radical —OH.

An "amino group" is intended to mean the radical —NH$_2$.

An "alkylamino group" is intended to mean the radical —NHR where R is an alkyl group as defined above.

A "dialkylamino group" is intended to mean the radical —NR$_a$R$_b$ where R$_a$ and R$_b$ are each independently an alkyl group as defined above.

An "alkoxy group" is intended to mean the radical —OR where R is an alkyl group as defined above, for example, methoxy, ethoxy, propoxy, and the like.

An "alkoxycarbonyl group" is intended to mean the radical —C(O)OR where R is an alkyl group as defined above.

An "alkylsulfonyl group" is intended to mean the radical —SO$_2$R where R is an alkyl group as defined above.

An "alkylaminocarbonyl group" is intended to mean the radical —C(O)NHR where R is an alkyl group as defined above.

A "dialkylaminocarbonyl group" is intended to mean the radical —C(O)NR$_a$R$_b$ where R$_a$ and R$_b$ are each independently an alkyl group as defined above.

A "mercapto group" is intended to mean the radical —SH.

An "alkylthio group" is intended to mean the radical —SR where R is an alkyl group as defined above.

A "carboxy group" is intended to mean the radical —C(O)OH.

A "carbamoyl group" is intended to mean the radical —C(O)NH$_2$.

An "aryloxy group" is intended to mean the radical —OR$_c$ where R$_c$ is an aryl group as defined above.

A "heteroaryloxy group" is intended to mean the radical —OR$_d$ where R$_d$ is a heteroaryl group as defined above.

An "arylthio group" is intended to mean the radical —SR$_c$ where R$_c$ is an aryl group as defined above.

A "heteroarylthio group" is intended to mean the radical —SR$_d$ where R$_d$ is a heteroaryl group as defined above.

A "pharmaceutically acceptable prodrug" is intended to mean a compound that may be converted under physiological conditions or by solvolysis to a compound of formula I or formula X.

A "pharmaceutically acceptable active metabolite" is intended to mean a pharmacologically active product produced through metabolism in the body of a compound of formula I or formula X.

A "pharmaceutically acceptable solvate" is intended to mean a solvate that retains the biological effectiveness and properties of the biologically active components of compounds of formulas I and X. Examples of pharmaceutically acceptable solvates include, but are not limited to, compounds of formula I or X in combination with water, isopropanol, ethanol, methanol, DMSO, ethyl acetate, acetic acid, or ethanolamine.

A "pharmaceutically acceptable salt" is intended to mean a salt that retains the biological effectiveness and properties of the free acids and bases of compounds of formulas I and X and that is not biologically or otherwise undesirable. Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates.

If the inventive compound is a base, the desired salt may be prepared by any suitable method known to the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acids such as glucuronic acid and galacturonic acid; alpha-hydroxy acids such as citric acid and tartaric acid; amino acids such as aspartic acid and glutamic acid; aromatic acids such as benzoic acid and cinnamic acid; sulfonic acids such as p-toluenesulfonic acid or ethanesulfonic acid; or the like.

If the inventive compound is an acid, the desired salt may be prepared by any suitable method known to the art, including treatment of the free acid with an inorganic or organic base, such as an amine (primary, secondary or tertiary); an alkali metal or alkaline earth metal hydroxide; or the like. Illustrative examples of suitable salts include organic salts derived from amino acids such as glycine and arginine; ammonia; primary, secondary and tertiary amines; and cyclic amines such as piperidine, morpholine, and piperazine, and inorganic salts derived from sodium, calcium, potassium, magnesium, manganese, iron, copper, zinc, aluminum, and lithium.

In the case of compounds, salts, or solvates that are solids, it is understood by those skilled in the art that the inventive compounds, salts, and solvates may exist in different crystal forms, all of which are intended to be within the scope of the present invention.

The inventive compounds may exist as single stereoisomers, racemates, and/or mixtures of enantiomers and/or diastereomers. All such single stereoisomers, racemates, and mixtures thereof are intended to be within the scope of the present invention. Preferably, the inventive compounds are used in optically pure form.

As generally understood by those skilled in the art, an optically pure compound is one that is enantiomerically pure. As used herein, the term "optically pure" is intended to mean a compound which comprises at least a sufficient amount of a single enantiomer to yield a compound having the desired pharmacological activity. Preferably, "optically pure" is intended to mean a compound that comprises at least 90% of a single isomer (80% enantiomeric excess), preferably at least 95% (90% e.e.), more preferably at least 97.5% (95% e.e.), and most preferably at least 99% (98% e.e.).

Preferably in the above formulas I and X, $R_1$ and $R_{61}$ are H or F. In the compounds of formula I, preferably M is O.

Preferably $R_{20}$ in formula I is H, an alkyl group, a cycloalkyl group, a heterocycloalkyl group, an aryl group, a heteroaryl group, $-OR_{17}$, $-SR_{17}$, $-NR_{17}R_{18}$, $-NR_{19}NR_{17}R_{18}$, or $-NR_{17}OR_{18}$, wherein $R_{17}$, $R_{18}$, and $R_{19}$ independently are H, an alkyl group, a cycloalkyl group, a heterocycloalkyl group, an aryl group, a heteroaryl group, or an acyl group. More preferably $R_{20}$ is the alkyl group $-C(R_{41})(R_{42})NR_{43}R_{44}$, wherein $R_{41}$ and $R_{42}$ independently are H, an alkyl group, a cycloalkyl group, a heterocycloalkyl group, an aryl group, or a heteroaryl group; and $R_{43}$ and $R_{44}$ independently are H, an alkyl group, a cycloalkyl group, a heterocycloalkyl group, an aryl group, a heteroaryl group, $-NR_{45}R_{46}$, $-C(O)R_{45}$, $-C(S)R_{45}$, $-C(O)NR_{45}R_{46}$, $-C(S)NR_{45}R_{46}$, $-C(O)NR_{45}OR_{46}$, $-C(S)NR_{45}OR_{46}$, $-C(O)SR_{45}$, $-C(O)OR_{45}$, $-C(S)OR_{45}$, $-C(S)SR_{45}$, $-OR_{45}$, $-SR_{45}$, $-C(O)NR_{45}NR_{46}R_{47}$, $-C(S)NR_{45}NR_{46}R_{47}$, $-SOR_{45}$, $-SO_2R_{45}$, $-S(O)NR_{45}R_{46}$, $-S(O)NR_{45}(OR_{46})$, $-SO_2NR_{45}R_{46}$, $-SO_2NR_{45}(OR_{46})$, or $-SO_3R_{45}$, wherein $R_{45}$, $R_{46}$, and $R_{47}$ independently are H, an alkyl group, a cycloalkyl group, a heterocycloalkyl group, an aryl group, a heteroaryl group, or wherein any combination of $R_{41}$, $R_{42}$, $R_{43}$, and $R_{44}$, together with the atoms to which they are attached, form a cycloalkyl group or a heterocycloalkyl group. Preferably at least one of $R_{43}$ and $R_{44}$ is $-C(O)SR_{45}$ or $-C(O)OR_{45}$. Preferably $R_{45}$ is an alkyl group, a cycloalkyl group, an aryl group, a heterocycloalkyl group, or a heteroaryl group, and more preferably a $C_1-C_{10}$ alkyl group.

In the compounds of formula I, preferably $D_1$ and $D_2$ are $-OR_{25}$, $=O$, $=S$, $\equiv N$, $=NR_{25}$, or $-NR_{25}R_{26}$, wherein $R_{25}$ and $R_{26}$ are independently H, an alkyl group, a cycloalkyl group, a heterocycloalkyl group, an aryl group, or a heteroaryl group, or, together with the nitrogen atom to which they are bonded, form a heterocycloalkyl group, and more preferably $D_1$ and $D_2$ are $=O$. Preferably, in the compounds of formula I, $A_1$ and $A_2$ are C, CH, S, or S(O), and more preferably $A_1$ and $A_2$ are C.

Preferably, in the compounds of formula I, $B_1$ and $B_2$ are $NR_{17}R_{18}$, wherein $R_{17}$ and $R_{18}$ are independently H, an alkyl group, a cycloalkyl group, a heterocycloalkyl group, an aryl group, a heteroaryl group, or an acyl group.

In the compounds of formula I and X, preferably Z and $Z_1$ are independently H, an aryl group, or a heteroaryl group, $-C(O)R_{21}$, $-CO_2R_{21}$, $-CN$, $-C(O)NR_{21}$, $R_{22}$, $-C(O)NR_{21}OR_{22}$, $-C(S)R_{21}$, $-C(S)NR_{21}R_{22}$, $-NO_2$, $-SOR_{21}$, $-SO_2R_{21}$, $-SO_2NR_{21}R_{22}$, $-SO(NR_{21})(OR_{22})$, $-SONR_{21}$, $-SO_3R_{21}$, $-C(O)NR_{21}NR_{22}R_{23}$, or $-C(S)NR_{21}NR_{22}R_{23}$, wherein $R_{21}$, $R_{22}$, and $R_{23}$ are independently H, an alkyl group, a cycloalkyl group, a heterocycloalkyl group, an aryl group, a heteroaryl group, an acyl group, or a thioacyl group, or wherein any two of $R_{21}$, $R_{22}$, and $R_{23}$, together with the atom(s) to which they are bonded, form a heterocycloalkyl group, or Z and $Z_1$, both as defined above, together with the atoms to which they are attached, form a heterocycloalkyl group.

In the compounds of formula X, preferably $R_{66}$ is $-C(O)OR_{68}$ or $-C(O)SR_{68}$, wherein $R_{68}$ is an alkyl group, a cycloalkyl group, an aryl group, a heterocycloalkyl group, or a heteroaryl group.

Particularly preferred embodiments of the present invention include the following compounds (1–8, 10, and 11) of formula II:

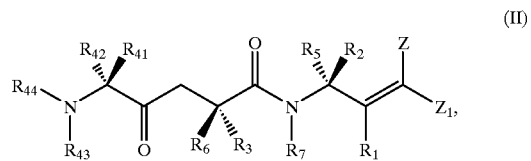

wherein $R_1$, $R_5$, $R_6$, $R_7$, $R_{42}$, $R_{43}$, and Z are H, $R_2$ is $CH_2CH_2C(O)NH_2$, and $R_3$, $R_{41}$, $Z_1$, and $R_{44}$ are selected from one of the following groups:

(1) $R_3$ is $CH_2Ph$, $R_{41}$ is $CH_2CH(CH_3)_2$, $Z_1$ is $CO_2CH_2CH_3$, and

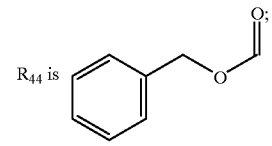

(2) $R_3$ is $CH_2Ph$, $R_{41}$ is $CH_2CH(CH_3)_2$, $Z_1$ is $CO_2CH_2CH_3$, and

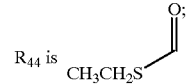

(3) $R_3$ is $CH_2Ph$, $R_{41}$ is $CH_2CH(CH_3)_2$,

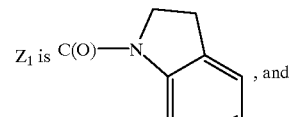

(4) $R_3$ is $CH_2Ph$, $R_{41}$ is $CH(CH_3)_2$, $Z_1$ is $CO_2CH_2CH_3$, and

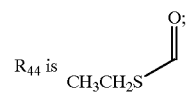

(5) $R_3$ is $CH_2Ph$, $R_{41}$ is $CH(CH_3)_2$, $Z_1$ is $CO_2CH_2CH_3$, and

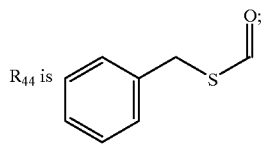

(6) $R_3$ is $CH_2Ph$, $R_{41}$ is $CH_2CH(CH_3)_2$, $Z_1$ is $CO_2CH_2CH_3$, and

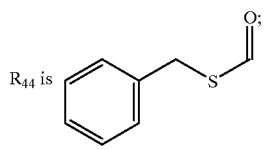

(7) $R_3$ is $CH_2Ph$, $R_{41}$ is $CH(CH_3)_2$, $Z_1$ is $CO_2CH_2CH_3$, and

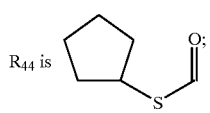

(8) $R_3$ is $CH_2Ph$, $R_{41}$ is $CH_2CH(CH_3)_2$, $Z_1$ is $CO_2CH_2CH_3$, and

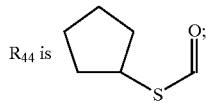

(10) $R_3$ is $CH_2(p{-}CH_3)Ph$, $R_{41}$ is $CH(CH_3)_2$, $Z_1$ is $CO_2CH_2CH_3$, and

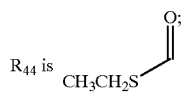

and

(11) $R_3$ is $CH_2(p{-}CH_3)Ph$, $R_{41}$ is $CH(CH_3)_2$, $Z_1$ is $CO_2CH_2CH_3$, and

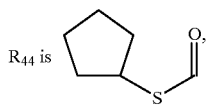

and pharmaceutically acceptable prodrugs, salts, active metabolites, and solvates thereof.

Another preferred embodiment of the invention includes a compound (9) of formula III:

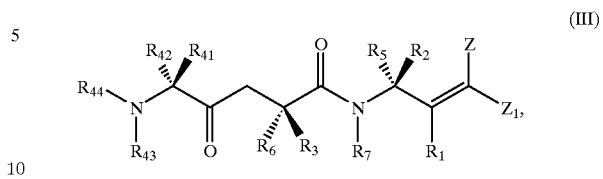

wherein $R_1$, $R_5$, $R_6$, $R_7$, $R_{42}$, $R_{43}$, and Z are H, $R_3$ is $CH_2Ph$, $R_2$ is $CH_2CH_2C(O)NH_2$, $R_{41}$ is $CH_2CH(CH_3)_2$, $Z_1$ is $CO_2CH_2CH_3$, and

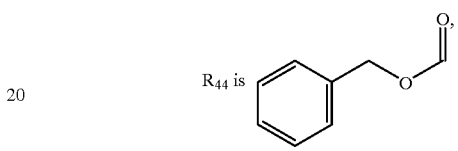

and pharmaceutically acceptable prodrugs, salts, active metabolites, and solvates thereof.

The present invention is still further directed to compositions comprising at least one compound of formula II:

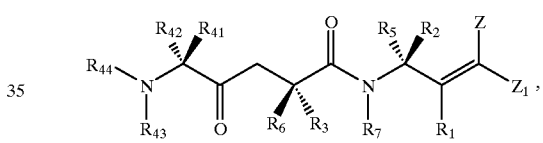

wherein $R_1$, $R_5$, $R_6$, $R_7$, $R_{42}$, $R_{43}$, and Z are H, $R_3$ is $CH_2Ph$, $R_2$ is $CH_2CH_2C(O)NH_2$, $R_{41}$ is $CH_2CH(CH_3)_2$, $Z_1$ is $CO_2CH_2CH_3$, and

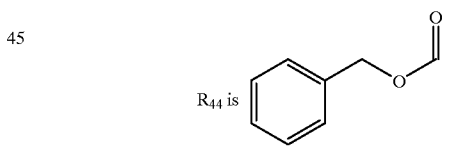

or a pharmaceutically acceptable prodrug, salt, active metabolite, or solvate thereof, and at least one compound of formula III:

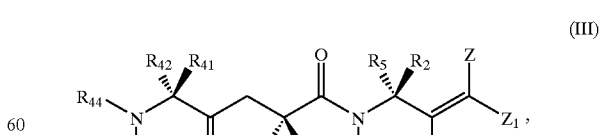

wherein $R_1$, $R_5$, $R_6$, $R_7$, $R_{42}$, $R_{43}$, and Z are H, $R_3$ is $CH_2Ph$, $R_2$ is $CH_2CH_2C(O)NH_2$, $R_{41}$ is $CH_2CH(CH_3)_2$, $Z_1$ is $CO_2CH_2CH_3$, and $R_{44}$ is 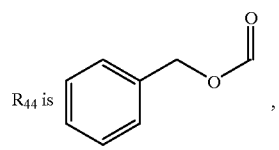, or a pharmaceutically acceptable prodrug, salt, active metabolite, or solvate thereof.

Additional preferred compounds according to the present invention include the following compounds (12 through 34) of formula IV:

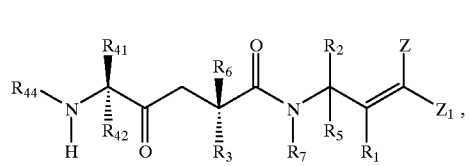
(IV)

wherein $R_1$, $R_5$, $R_6$, $R_7$, and $R_{42}$ are H, $R_2$ is $CH_2CH_2C(O)NH_2$, and $R_3$, Z, $Z_1$, $R_{41}$, and $R_{44}$ are selected from one of the following groups:

(12) $R_3$ is $CH_2(p—CH_3)Ph$, Z is H, $Z_1$ is $CO_2CH_2CH_3$, $R_{41}$ is $CH_2Ph$, and $R_{44}$ is 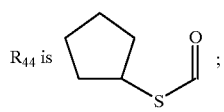;

(13) $R_3$ is $CH_2(p—F)Ph$, Z is H, $Z_1$ is $CO_2CH_2CH_3$, $R_{41}$ is $CH(CH_3)_2$, and $R_{44}$ is ;

(14) $R_3$ is $CH_2(p—F)Ph$, Z is H, $Z_1$ is $CO_2CH_2CH_3$, $R_{41}$ is $CH(CH_3)_2$, and $R_{44}$ is 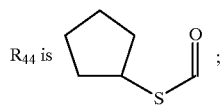;

(15) $R_3$ is $CH_2(p—CF_3)Ph$, Z is H, $Z_1$ is $CO_2CH_2CH_3$, $R_{41}$ is $CH(CH_3)_2$, and $R_{44}$ is ;

(16) $R_3$ is $CH_2(p—CF_3)Ph$, Z is H, $Z_1$ is $CO_2CH_2CH_3$, $R_{41}$ is $CH(CH_3)_2$, and $R_{44}$ is 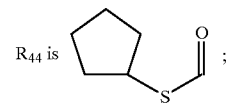;

(17) $R_3$ is $CH_2(p—CH_3)Ph$, Z and $Z_1$ together form

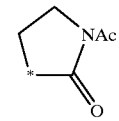

(where * indicates the point of attachment and the carbonyl group is cis to the $R_1$ group), $R_{41}$ is $CH(CH_3)_2$, and $R_{44}$ is 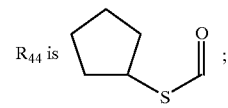;

(18) $R_3$ is $CH_2(p-F)Ph$, Z is H, $Z_1$ is $CO_2CH_2CH_3$, $R_{41}$ is $CH_2Ph$, and $R_{44}$ is 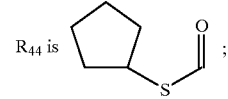;

(19) $R_3$ is $CH_2(p-F)Ph$, Z is H, $Z_1$ is $CO_2CH_2CH_3$, $R_{41}$ is $CH_2CH(CH_3)_2$, and $R_{44}$ is 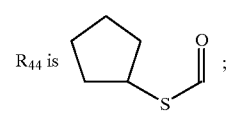;

(20) $R_3$ is $CH_2(p-CH_3)Ph$, Z is H, $Z_1$ is $CO_2CH_2CH_3$, $R_{41}$ is $CH(CH_3)_2$, and $R_{44}$ is 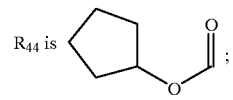;

(21) $R_3$ is $CH_2(p-CH_3)Ph$, Z is H, $Z_1$ is $CO_2CH_2CH_3$, $R_{41}$ is $CH_2CH(CH_3)_2$, and $R_{44}$ is 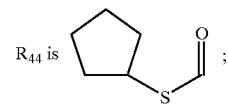;

(22) $R_3$ is $CH_2Ph$, Z is H, $Z_1$ is $CO_2CH_2CH_3$, $R_{41}$ is $C(CH_3)_3$, and $R_{44}$ is [cyclopentyl-S-C(=O)-] ;

(23) $R_3$ is $CH_2(p-CH_3)Ph$, Z is H, $Z_1$ is $CO_2CH_2CH_3$, $R_{41}$ is $CH(CH_3)_2$, and $R_{44}$ is [cyclopentyl-CH_2-C(=O)-] ;

(24) $R_3$ is $CH_2(p-F)Ph$, Z is H, $Z_1$ is $CO_2CH_2CH_3$, $R_{41}$ is cyclohexyl, and $R_{44}$ is [cyclopentyl-S-C(=O)-] ;

(25) $R_3$ is $CH_2(p-F)Ph$, Z is H, $Z_1$ is $CO_2CH_2CH_3$, $R_{41}$ is $CH(CH_3)_2$, and $R_{44}$ is [cyclopentyl-O-C(=O)-] ;

(26) $R_3$ is $CH_2(p-F)Ph$, Z is H, $Z_1$ is $CO_2CH_2CH_3$, $R_{41}$ is $CH(CH_3)_2$, and $R_{44}$ is [(CH_3)_3C-S-C(=O)-] ;

(27) $R_3$ is $CH_2(p-F)Ph$, Z is H, $Z_1$ is $CO_2CH_2CH_3$, $R_{41}$ is $CH(CH_3)_2$, and $R_{44}$ is [1,3-dithiolane-2-C(=O)-] ;

(28) $R_3$ is $CH_2(p-F)Ph$, Z is H, $Z_1$ is [-C(=O)-O-CH_2-(3-pyridyl)] , $R_{41}$ is $CH(CH_3)_2$, and $R_{44}$ is [cyclopentyl-S-C(=O)-] ;

(29) $R_3$ is $CH_2(p-F)Ph$, Z is H, $Z_1$ is [-C(=O)-O-CH_2-(3-pyridyl)]·HCl , $R_{41}$ is $CH(CH_3)_2$, and $R_{44}$ is [cyclopentyl-S-C(=O)-] ;

(30) $R_3$ is $CH_2(p-F)Ph$, Z is H, $Z_1$ is [-C(=O)-O-CH_2-(3-pyridyl)] , $R_{41}$ is $CH(CH_3)_2$, and $R_{44}$ is [1,3-dithiolane-2-C(=O)-] ;

(31) $R_3$ is $CH_2(p-F)Ph$, Z is H, $Z_1$ is $CO_2CH_2CH_3$, $R_{41}$ is $CH(CH_3)_2$, and $R_{44}$ is [1,3-dithiane-2-C(=O)-] ;

(32) $R_3$ is $CH_2(p-F)Ph$, Z is H, $Z_1$ is [-C(=O)-O-CH_2-(3-pyridyl)] , $R_{41}$ is $CH(CH_3)_2$, and

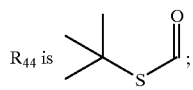

(33) $R_3$ is $CH_2(p-F)Ph$, Z is H, $Z_1$ is $CO_2CH_2CH_2OH$, $R_{41}$ is $CH(CH_3)_2$, and

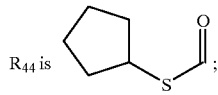

(34) $R_3$ is $CH_2(p-F)Ph$, Z is H, $Z_1$ is $CO_2CH_2CH_3$, $R_{41}$ is $CH(CH_3)_2$, and

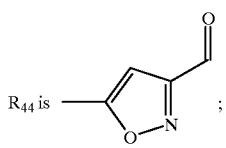

and pharmaceutically acceptable prodrugs, salts, active metabolites, or solvates thereof.

The present invention is even further directed to methods of inhibiting picornaviral 3C protease activity, comprising contacting the protease with an effective amount of a compound of formula I or X or a pharmaceutically acceptable prodrug, salt, active metabolite, or solvate thereof. For example, one can inhibit picornaviral 3C protease activity in mammalian tissue by administering a compound of formula I or X or a pharmaceutically acceptable prodrug, salt, active metabolite, or solvate thereof. More particularly, the present invention is directed to methods of inhibiting rhinoviral protease activity.

The activity of the inventive compounds as inhibitors of picornaviral 3C protease activity may be measured by any of the methods available to those skilled in the art, including in vivo and in vitro assays. An example of a suitable assay for activity measurements is the Antiviral HI-HeLa Cell Culture Assay, described herein.

Administration of the compounds of the formula I or X, or their pharmaceutically acceptable prodrugs, salts, active metabolites, and solvates, may be performed according to any of the accepted modes of administration available to those skilled in the art. Illustrative examples of suitable modes of administration include, but are not limited to, oral, nasal, parenteral, topical, transdermal, and rectal.

The inventive compounds of formulas I and X, and their pharmaceutically acceptable prodrugs, salts, active metabolites, and solvates, may be administered as a pharmaceutical composition in any suitable pharmaceutical form recognizable to the skilled artisan. Suitable pharmaceutical forms include, but are not limited to, solid, semisolid, liquid, or lyopholized formulations, such as tablets, powders, capsules, suppositories, suspensions, and aerosols. The pharmaceutical composition may also include suitable excipients, diluents, vehicles, and carriers, as well as other pharmaceutically active agents, depending upon the intended use.

Acceptable methods of preparing suitable pharmaceutical forms of the pharmaceutical compositions are known to those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

Solid or liquid pharmaceutically acceptable carriers, diluents, vehicles, or excipients may be employed in the pharmaceutical compositions. Illustrative solid carriers include starch, lactose, calcium sulphate dihydrate, terra alba, sucrose, talc, gelatin, pectin, acacia, magnesium stearate, and stearic acid. Illustrative liquid carriers may include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g. solution), or a nonaqueous or aqueous liquid suspension.

A dose of the pharmaceutical composition contains at least a therapeutically effective amount of the active compound (i.e., a compound of formula I or X or a pharmaceutically acceptable prodrug, salt, active metabolite, or solvate thereof) and preferably is made up of one or more pharmaceutical dosage units. The selected dose may be administered to a mammal, for example, a human patient, in need of treatment mediated by inhibition of 3C protease activity, by any known method of administering the dose including topical, for example, as an ointment or cream; orally; rectally, for example, as a suppository; parenterally by injection; or continuously by intravaginal, intranasal, intrabronchial, intraaural, or intraocular infusion.

A "therapeutically effective amount" is intended to mean that amount of a compound of formula I or X that, when administered to a mammal in need thereof, is sufficient to effect treatment for disease conditions alleviated by the inhibition of the activity of one or more picornaviral 3C proteases, such as human rhinoviruses, human poliovirus, human coxsackieviruses, encephalomyocarditis viruses, menigovirus, and hepatitis A virus. The amount of a given compound of formula I or X that will correspond to a "therapeutically effective amount" will vary depending upon factors such as the particular compound, the disease condition and the severity thereof, the identity of the mammal in need thereof, but it can nevertheless be readily determined by one of skill in the art.

"Treating" or "treatment" is intended to mean at least the mitigation of a disease condition in a mammal, such as a human, that is alleviated by the inhibition of the activity of one or more picornaviral 3C proteases, such as human rhinoviruses, human poliovirus, human coxsackieviruses, encephalomyocarditis viruses, menigovirus, and hepatitis A virus, and includes:

(a) prophylactic treatment in a mammal, particularly when the mammal is found to be predisposed to having the disease condition but not yet diagnosed as having it;

(b) inhibiting the disease condition; and/or (c) alleviating, in whole or in part, the disease condition.

The inventive compounds, and their salts, solvates, active metabolites, and prodrugs, may be prepared by employing the techniques available in the art using starting materials that are readily available. Certain novel and exemplary methods of preparing the inventive compounds are described below.

Preferably, the inventive compounds of formula I are prepared by the methods of the present invention, including the general methods shown below. In each of these general methods, $R_1$, $R_2$, $R_3$, $R_5$, $R_6$, $R_7$, $R_{20}$, $R_{41}$, $R_{42}$, Z, and $Z_1$ are as defined above (for formulae I, II, III, IV, and X).

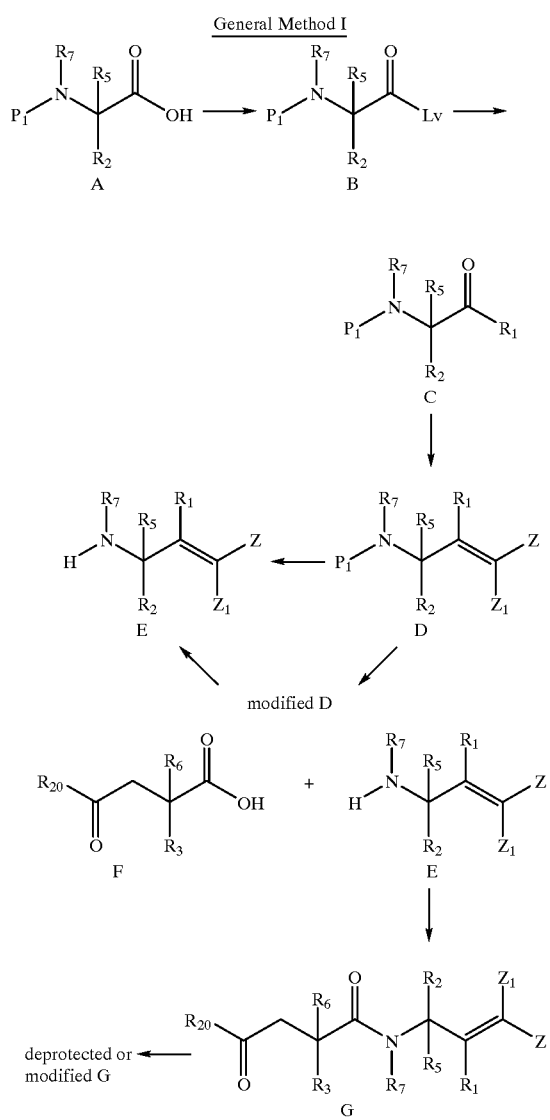

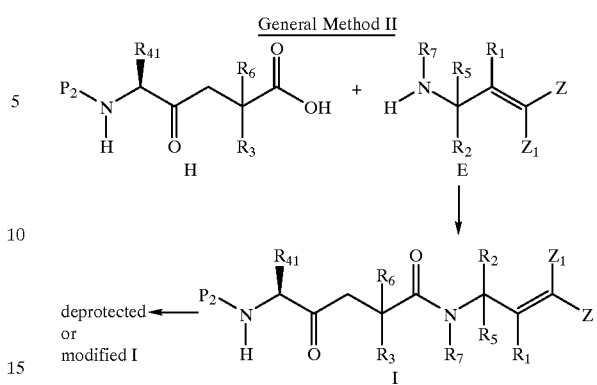

In General Method I, amino acid A, where $P_1$ is an appropriate protecting group for nitrogen, is converted to carbonyl derivative B, where "Lv" is a leaving group. Compound B is subjected to a reaction where "Lv" is replaced by $R_1$ to give derivative C. Derivative C is then transformed into unsaturated product D. Unsaturated compound D is deprotected to give free amine (or salt thereof) E, or modified one or more times at $R_2$, $R_5$, Z, and/or $Z_1$ to give one or more modified D compounds. Modified D is then deprotected to give amine (or salt thereof) E.

Amine E is subsequently subjected to an amide-forming reaction with carboxylic acid F (for which the preparation of representative examples is described below) to give final product G. If protecting groups were used on any R groups ($R_1$, $R_2$, $R_3$, $R_5$, $R_6$, $R_7$, and/or $R_{20}$), on Z and/or on $Z_1$, product G is deprotected and/or further modified to yield "deprotected or modified G."

In General Method II, amine E, which can be prepared as described in General Method I, is subjected to an amide-forming reaction with carboxylic acid H, where $P_2$ is an appropriate protecting group for nitrogen, and where at least one of $R_3$ and $R_6$ is H, to give final product I. Carboxylic acid H can be prepared as a mixture of diastereomers as described in Harbeson, S. L., Rich, D. H., *J. Med. Chem.* 1989, 32, 1378, the disclosure of which is incorporated herein by reference. The $P_2$ protecting group, along with any additional protecting groups that were used on any R groups ($R_1$, $R_2$, $R_3$, $R_5$, $R_6$, $R_7$, and/or $R_{41}$), on Z and/or on $Z_1$, is subsequently deprotected and/or further modified to yield "deprotected or modified I."

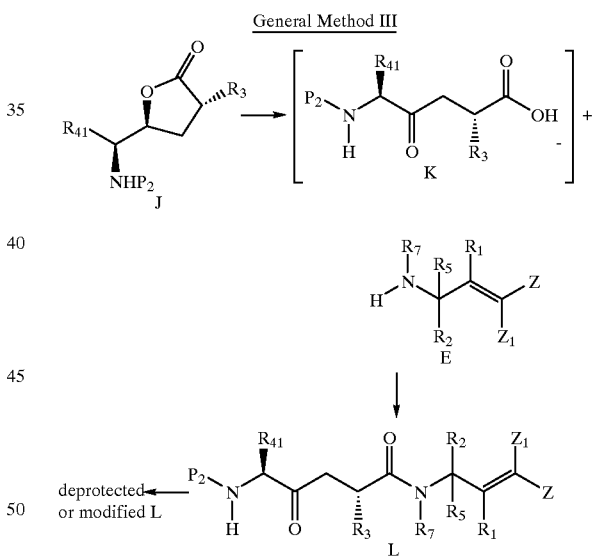

In General Method III, optically active lactone J, where $P_2$ is an appropriate protecting group for nitrogen, is transformed by a two-step procedure (basic hydrolysis and subsequent oxidation) into carboxylic acid K. Lactone J can be prepared by the method described in General Method IV below and by many literature methods including, but not limited to, those described in the following: (a) Herold, P.; Duthaler, R.; Rihs, G.; Angst, C., *J. Org. Chem.* 1989, 54, 1178; (b) Bradbury, R. H.; Revill, J. M.; Rivett, J. E.; Waterson, D., *Tetrahedron Lett.* 1989, 30, 3845; (c) Bradbury, R. H.; Major, J. S.; Oldham, A. A.; Rivett, J. E.; Roberts, D. A.; Slater, A. M.; Timms, D.; Waterson, D., *J. Med. Chem.* 1990, 33, 2335; (d) Wuts, P. G.; Ritter, A. R.; Pruitt, L. E., *J. Org. Chem.* 1992, 57, 6696; (e) Jones, D. M.;

Nilsson, B.; Szelke, M., *J. Org. Chem.* 1993, 58, 2286; (f) Pégorier, L.; Larchevéque, M., *Tetrahedron Lett.* 1995, 36, 2753; (g) Dondoni, A.; Perrone, D.; Semola, M. T., *J. Org. Chem.* 1995, 60, 7927, all of which are incorporated herein by reference. Carboxylic acid K is not isolated in pure form, but is subjected to an amide-forming reaction with amine E, which can be prepared as described in General Method I, to provide final product L. The $P_2$ protecting group, along with any additional protecting groups that were used on any R groups ($R_1$, $R_2$, $R_3$, $R_5$, $R_7$, and/or $R_{41}$), on Z and/or on $Z_1$, is subsequently deprotected and/or further modified to yield "deprotected or modified L."

General Method IV

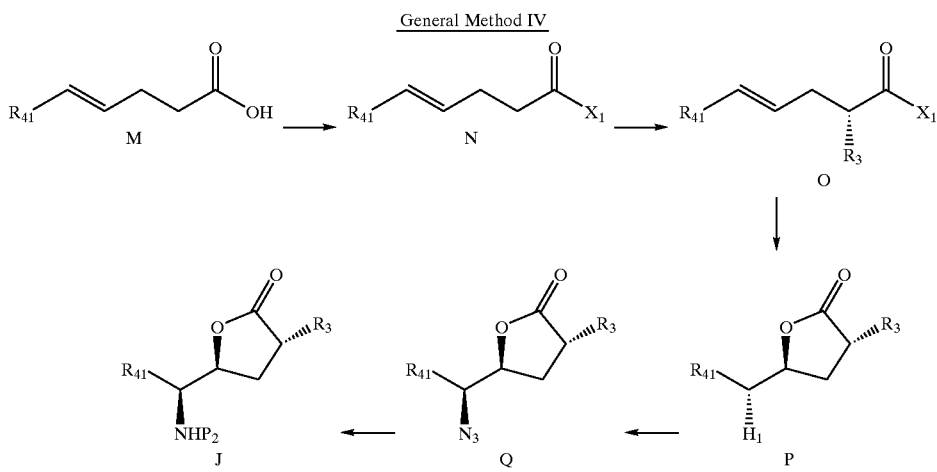

Lactone J may be prepared in optically active form by General Method IV (see: (a) Herold, P.; Duthaler, R.; Rihs, G.; Angst, C., *J. Org. Chem.* 1989, 54, 1178; (b) Bradbury, R. H.; Revill, J. M.; Rivett, J. E.; Waterson, D., *Tetrahedron Lett.* 1989, 30, 3845; (c) Bradbury, R. H.; Major, J. S.; Oldham, A. A.; Rivett, J. E.; Roberts, D. A.; Slater, A. M.; Timms, D.; Waterson, D., *J. Med. Chem.* 1990, 33, 2335). A γ,δ-unsaturated carboxylic acid M, which incorporates $R_{41}$, is transformed into the corresponding acid chloride (not shown). This acid chloride is subjected to an amide-forming reaction with a chiral amine or a chiral oxazolidone to provide derivative N (in which $X_1$ is a chiral amine or a chiral oxazolidone). Compound N is subsequently deprotonated, and the resulting enolate is diastereoselectively alkylated with an electrophile corresponding to $R_3$ to provide compound O. This material is then subjected to a halolactonization reaction to provide halo-lactone P, in which $H_1$ is Br or I. Halo-lactone P is subsequently transformed into azide Q, and this material is then converted into lactone J, where $P_2$ is an appropriate protecting group for nitrogen.

General Method V

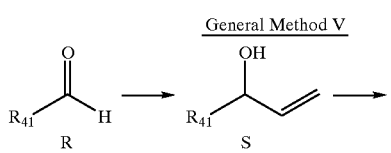

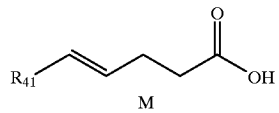

γ,δ-Unsaturated carboxylic acid M may be prepared by General Method V (see: Herold, P.; Duthaler, R.; Rihs, G.; Angst, C., *J. Org. Chem.* 1989, 54, 1178). An aldehyde R, which incorporates $R_{41}$, is coupled with vinylmagnesium bromide to give alcohol S. Alcohol S is then transformed into γ,δ-unsaturated carboxylic acid M by a three step procedure as follows: (i) treatment with diethyl malonate and catalytic Ti(OEt)$_4$ at 160° C. for 1 hour, (ii) heating at 190° C. for 4 hours, and (iii) hydrolysis with ethanolic KOH at reflux.

General Method VI

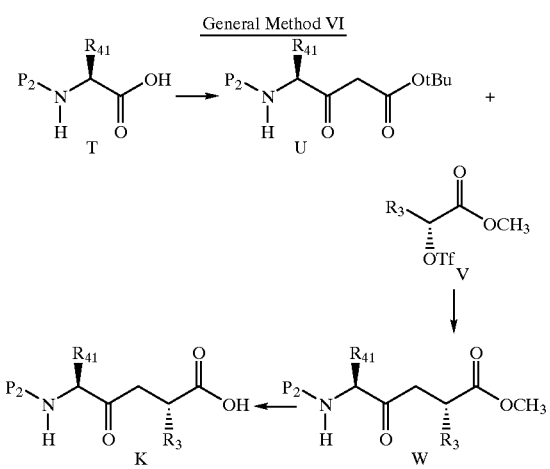

Carboxylic acid K also may be prepared by General Method VI (see: Hoffman, R. V., Tao, J., *Tetrahedron,* 1997, 53, 7119, which document is entirely incorporated herein by reference). An amino acid T, which incorporates $R_{41}$ and where $P_2$ is an appropriate protecting group for nitrogen, is transformed into β-ketoester U. Compound U is deprotonated, and the resulting anion is condensed with triflate V, which incorporates $R_3$. The coupling product thus obtained is treated with trifluoroacetic acid to provide ketoester W, and this material is subsequently hydrolyzed to afford carboxylic acid K. If basic hydrolysis results in epimerization, ketoester W can be transesterified [allyl alcohol, Ti(Oi-Pr)$_4$] and subsequently deprotected under neutral conditions [Pd(PPh$_3$)$_4$, morpholine] to give carboxylic acid K. Triflate V, in turn, may be prepared from the corresponding alcohol by treatment with trifluoromethanesulfonic anhydride and 2,6-lutidine.

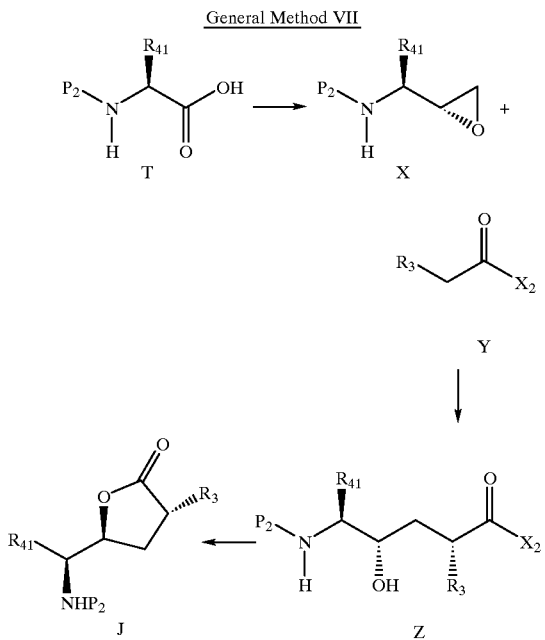

Lactone J also may be prepared by General Method VII (see: (a) Askin, D., Wallace, M. A., Vacca, J. P., Reamer, R. A., Volante, R. P., Shinkai, I. *J. Org. Chem.* 1992, 57, 2771 (b) McWilliams, J. C., Armstrong, J. D., Zheng, N., Bhupathy, M., Volante, R. P., Reider, P. J., *J. Am. Chem. Soc.* 1996, 118, 11970; each of these documents is entirely incorporated herein by reference). An amino acid T, which incorporates R$_{41}$ and where P$_2$ is an appropriate protecting group for nitrogen, is transformed into epoxide X (single diastereomer) by the method described in: Luly, J. R., Dellaria, J. F., Plattner, J. J., Soderquist, J. L., Yi, N., *J. Org. Chem.* 1987, 52, 1487, the disclosure of which is entirely incorporated herein by reference. Alternatively, X may be prepared from T as a mixture of diastereomers as described in the "Examples" section of this document. Epoxide X is condensed with the anion derived from compound Y, which incorporates R$_3$ and in which X$_2$ is a chiral auxiliary [including (1S,2R)-1-aminoindan-2-ol acetonide] to afford coupling product Z. If X was utilized as a mixture of diastereomers, the diastereomer of Z depicted below is purified from other Z isomers (if any) produced in the coupling reaction. This material is subsequently cyclized under acidic conditions to provide lactone J. Compound Y may be prepared from the corresponding carboxylic acid (not shown) by the method outlined in: Askin, D., Wallace, M. A., Vacca, J. P., Reamer, R. A., Volante, R. P., Shinkai, I., *J. Org. Chem.* 1992, 57, 2771.

Suitable protecting groups for nitrogen are recognizable to those skilled in the art and include, but are not limited to benzyloxycarbonyl, t-butoxycarbonyl, 9-fluorenylmethoxycarbonyl, p-methoxybenxyloxycarbonyl, trifluoroacetamide, and p-toluenesulfonyl. Suitable protecting groups for oxygen are recognizable to those skilled in the art and include, but are not limited to —CH$_3$, —CH$_2$CH$_3$, tBu, —CH$_2$Ph, —CH$_2$CH=CH$_2$, —CH$_2$OCH$_2$CH$_2$Si(CH$_3$)$_3$, and —CH$_2$CCl$_3$. Other examples of suitable protecting groups for nitrogen or oxygen can be found in T. Green & P. Wuts, *Protective Groups in Organic Synthesis* (2nd ed. 1991), the disclosure of which is incorporated herein by reference.

Suitable leaving groups also are recognizable to those skilled in the art and include, but are not limited to, Cl, Br, I, sulfonates, O-alkyl groups,

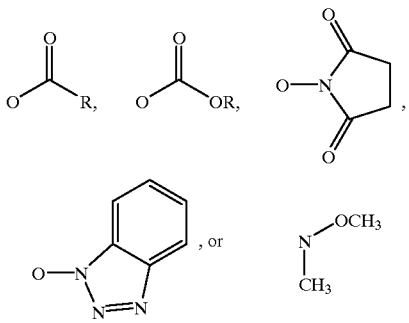

Other examples of suitable leaving groups are described in J. March, *Advanced Organic Chemistry, Reactions, Mechanisms, and Structure* (4th ed. 1992) at pages 205, 351–56, 642– 43, 647, 652–53, 666, 501, 520–21, 569, 579–80, 992–94, 999–1000, 1005, and 1008, the disclosure of which is incorporated herein by reference.

EXAMPLES

Examples of the processes used to make several of the compounds of formula I are set forth below. These Examples are intended to illustrate the present invention without limiting it. The structures of the compounds of the following examples were confirmed by one or more of the following: proton magnetic resonance spectroscopy, infrared spectroscopy, elemental microanalysis, mass spectrometry, thin layer chromatography, melting point, and boiling point.

Proton magnetic resonance ($^1$H NMR) spectra was determined using a Varian UNITYplus 300 spectrometer operating at a field strength of 300 megahertz (MHZ). Chemical shifts are reported in parts per million (ppm, δ) downfield from an internal tetramethylsilane standard. Alternatively, $^1$H NMR spectra were referenced to residual protic solvent signals as follows: CHCl$_3$=7.26 ppm; DMSO=2.49 ppm, C$_6$HD$_5$=7.15 ppm. Peak multiplicities are designated as follows: s, singlet; d, doublet; dd, doublet of doublets; t, triplet; q, quarter; br, broad resonance; m, multiplet. Coupling constants (J) are given in hertz (Hz). Infrared absorption (IR) spectra were obtained using a Perkin-Elmer 1600 series FTIR spectrometer. Elemental microanalyses were performed by Atlantic Microlab Inc., Norcross, Ga. and gave results for the elements stated within ±0.4% of the theoretical values.

Flash column chromatography was performed using Silica gel 60 (Merck Art 9385). Analytical thin layer chromatography (TLC) was performed using precoated sheets of Silica 60 F$_{254}$ (Merck Art 5719). Melting points were determined on a Mel-Temp apparatus and are uncorrected. All reactions were performed in septum-sealed flasks under a slight positive pressure of argon unless otherwise noted. All commercial reagents were used as received from their respective suppliers with the following exceptions. Tetrahydrofuran (THF) was distilled from sodium-benzophenone ketyl prior to use. Dichloromethane ($CH_2Cl_2$) was distilled from calcium hydride prior to use. Anhydrous lithium chloride was prepared by heating at 110° C. under vacuum overnight. $Et_2O$ refers to diethyl ether. DMF refers to N,N-dimethylformamide. DMSO refers to dimethylsulfoxide. Other abbreviations include: $CH_3OH$ (methanol), EtOH (ethanol), EtOAc (ethyl acetate), DME (ethylene glycol dimethyl ether), Ac (acetyl), Me (methyl), Et (ethyl), Ph (phenyl), Bn (benzyl), CyPentyl (cyclopentyl), Tr (triphenylmethyl), CBZ (benzyloxycarbonyl), BOC (tert-butoxycarbonyl), Gln (glutamine), Leu (leucine), Phe (phenylalanine), Val (valine). Additionally, "l" represents naturally occurring amino acids, "d" represents unnatural amino acids, and "dl" represents a racemic mixture of the two.

A simplified naming system employing amino acid abbreviations is used to identify some intermediates and final products. When naming compounds, italicized amino acid abbreviations represent modifications at the C-terminus of that residue where the following apply:

1. acrylic acid esters are reported as "e" (trans) propenoates;
2. acrylamides are reported as "e" (trans) propenamides; and
3. N-acetyl-pyrrolidin-2-ones are reported as "e" (trans) 1-acetyl-3-methylene-pyrrolidin-2-ones.

In addition, the terminology "$AA_1\Psi[COCH_2]$-$AA_2$" indicates that, for any peptide sequence, two amino acids ($AA_1$ and $AA_2$) linked by an amide bond are replaced by a ketomethylene dipeptide isostere moiety.

EXAMPLE 1

Preparation of a Mixture of Compound 1 and Compound 9 (~1:1): Ethyl-3-(CBZ-l-Leu$\Psi$ [$COCH_2$]-d/l-Phe-l-Gln)-e-Propenoate Preparation of Intermediate [BOC-L-(Tr-Gln)]-N(OMe)Me.

Isobutyl chloroformate (4.77 mL, 36.8 mmol, 1.0 equiv) was added to a solution of [BOC-l-(Tr-Gln)]-OH (18.7 g, 36.7 mmol, 1 equiv) and 4-methylmorpholine (8.08 mL, 73.5 mmol, 2.0 equiv) in $CH_2Cl_2$ (250 mL) at 0° C. The reaction mixture was stirred at 0° C. for 20 minutes, then N,O-dimethylhydroxylamine hydrochloride (3.60 g, 36.7 mmol, 1.0 equiv) was added. The resulting solution was stirred at 0° C. for 20 minutes and at 23° C. for 2 hours, and then was partitioned between water (150 mL) and $CH_2Cl_2$ (2×150 mL). The combined organic layers were dried over $Na_2SO_4$, and were concentrated. Purification of the residue by flash column chromatography (gradient elution, 40%→20% hexanes in EtOAc) provided [BOC-l-(Tr-Gln)]-N(OMe)Me (16.1 g, 82%) as a white foam: $R_f$=0.22 (50% EtOAc in hexanes); IR ($cm^{-1}$) 3411, 3329, 3062, 1701, 1659, $^1$H NMR ($CDCl_3$) δ 1.42 (s, 9H), 1.63–1.77 (m, 1H), 2.06–2.17 (m, 1H), 2.29–2.43 (m, 2H), 3.17 (s, 3H), 3.64 (s, 3H), 4.73 (s, br, 1H), 5.38–5.41 (m, 1H), 7.20–7.31 (m, 15H); Anal. ($C_{31}H_{37}N_3O_5$) C, H, N.

Preparation of Intermediate [BOC-l-(Tr-Gln)]-H.

Diisobutylaluminum hydride (50.5 mL of a 1.5 M solution in toluene, 75.8 mmol, 2.5 equiv) was added to a solution of [BOC-l-(Tr-Gln)]-N(OMe)Me (16.1 g, 30.3 mmol, 1 equiv) in THF at −78° C., and the reaction mixture was stirred at −78° C. for 4 hours. Methanol (4 mL) and 1.0 M HCl (10 mL) were added sequentially, and the mixture was warmed to 23° C. The resulting suspension was diluted with $Et_2O$ (150 mL) and was washed with 1.0 M HCl (3×100 mL), half-saturated $NaHCO_3$ (100 mL), and water (100 mL). The organic layer was dried over $MgSO_4$, filtered, and concentrated to give crude [BOC-l-(Tr-Gln)]-H (13.8 g, 97%) as a white solid: mp=114–116° C.; $R_f$=0.42 (50% EtOAc in hexanes); IR ($cm^{-1}$) 3313, 1697, 1494; $^1$H NMR ($CDCl_3$) δ 1.44 (s, 9H), 1.65–1.75 (m, 1H), 2.17–2.23 (m, 1H), 2.31–2.54 (m, 2H), 4.11 (s, br, 1H), 5.38–5.40 (m, 1H), 7.11 (s, 1H), 7.16–7.36 (m, 15H), 9.45 (s, 1H).

Preparation of Intermediate Ethyl-3-[BOC-l-(Tr-Gln)]-e-Propenoate.

Sodium bis(trimethylsilyl)amide (22.9 mL of a 1.0 M solution in THF, 22.9 mmol, 1.0 equiv) was added to a solution of triethyl phosphonoacetate (5.59 g, 22.9 mmol, 1.0 equiv) in THF (200 mL) at −78° C., and the resulting solution was stirred for 20 minutes at that temperature. Crude [BOC-l-(Tr-Gln)]-H (10.8 g, 22.9 mmol, 1 equiv) in THF (50 mL) was added via cannula, and the reaction mixture was stirred for 2 hours at −78° C., warmed to 0° C. for 10 minutes, and partitioned between 0.5 M HCl (150 mL) and a 1:1 mixture of EtOAc and hexanes (2×150 mL). The combined organic layers were dried over $Na_2SO_4$ and concentrated. Purification of the residue by flash column chromatography (40% EtOAc in hexanes) provided ethyl-3-[BOC-l-(Tr-Gln)]-e -propenoate (10.9 g, 88%) as a white foam: $R_f$=0.60 (50% EtOAc in hexanes); IR ($cm^{-1}$) 3321, 1710; $^1$NMR ($CDCl_3$) δ 1.27 (t, 3H, J=7.2), 1.42 (s, 9H), 1.70–1.78 (m, 1H), 1.80–1.96 (m, 1H), 2.35 (t, 2H, J=7.0), 4.18 (q, 2H, J=7.2), 4.29 (s, br, 1H), 4.82–4.84 (m, 1H), 5.88 (dd, 1H, J=15.7, 1.6), 6.79 (dd, 1H, J=15.7, 5.3), 6.92 (s, 1H), 7.19–7.34 (m, 15H); Anal. ($C_{33}H_{38}N_2O_5$) C, H, N.

Preparation of Intermediate Ethyl-3-[CBZ-l-Leu$\Psi$ [$COCH_2$]-d/l-Phe-l-(Tr-Gln)]-e-Propenoate.

HCl (3 mL of a 4.0 M solution in 1,4-dioxane) was added to a solution of ethyl-3-[BOC-l-(Tr-Gln)]-e-propenoate (0.091 g, 0.17 mmol, 1 equiv) in 1,4-dioxane (3 mL) at 23° C. The reaction mixture was stirred at 23° C. for 1.5 hours, then was concentrated under reduced pressure to afford crude ethyl-3-[$H_2$N-l-(Tr-Gln)]-e-propenoate●HCl as a viscous oil. This material was dissolved in $CH_2Cl_2$ (6 mL) and CBZ-l-Leu$\Psi$[$COCH_2$]-d/l-Phe-OH (0.068 g, 0.17 mmol, 1.0 equiv) [prepared as described in: Harbeson, S. L., Rich, D. H., *J. Med. Chem.* 1989, 32, 1378], 1-hydroxybenzotriazole hydrate (0.030 g, 0.22 mmol, 1.3 equiv), 4-methylmorpholine (0.055 mL, 0.50 mmol, 3.0 equiv), and 1-(3-dimethylaminopropyl)-3-ethylcarbodiimide hydrochloride (0.042 g, 0.22 mmol, 1.3 equiv) were added sequentially. The reaction mixture was stirred for 21 hours at 23° C. and then partitioned between water (100 mL) and EtOAc (2×100 mL). The combined organic layers were dried over $Na_2SO_4$ and were concentrated. Purification of the residue by flash column chromatography (50% EtOAc in hexanes) provided ethyl-3-[CBZ-l-Leu$\Psi$[$COCH_2$]-d/l-Phe-l-(Tr-Gln)]-e-propenoate (0.040 g, 28%) as a white foam: $R_f$=0.44 (50% EtOAc in hexanes); IR ($cm^{-1}$) 3317, 1712, 1667; $^1$H NMR ($CDCl_3$, approximately 1:1 mixture of diastereomers) δ 0.84–0.91 (m), 1.20–1.31 (m), 1.51–1.58 (m), 1.73–1.96 (m), 2.29–2.39 (m), 2.51–2.72 (m), 2.94–3.07 (m), 4.11–4.30 (m), 4.47–4.50 (m), 4.84 (d, J=7.8 Hz), 4.94–5.08 (m), 5.09 (s), 5.30 (d, J=7.2 Hz), 5.48 (d, J=14.3 Hz), 5.72–5.95 (m), 6.55–7.01 (m), 7.14–7.61 (m), 8.02–8.05 (m); Anal ($C_{52}H_{57}N_3O_7$●$0.75H_2O$) C, H, N.

Preparation of Product Ethyl-3-(CBZ-l-Leu$\Psi$[$COCH_2$]-d/l-Phe-l-Gln)-e-Propenoate.

Triisopropylsilane (0.10 mL) and trifluoroacetic acid (3 mL) were added sequentially to a solution of ethyl-3-[CBZ-l-Leu$\Psi$[$COCH_2$]-d/l-Phe-l-(Tr-Gln)]-e-propenoate (0.035 g, 0.042 mmol) in $CH_2Cl_2$ (4 mL) producing a bright yellow solution. The reaction mixture was stirred for 30 minutes at 23° C., then carbon tetrachloride (4 mL) was added, and the mixture was concentrated under reduced pressure. The residue was purified by flash column chromatography (5% CH$_3$OH in CH$_2$Cl$_2$) to afford ethyl-3-(CBZ-l-LeuΨ[COCH$_2$]-d/l-Phe-l-Gln)-e-propenoate (0.014 g, 56%) as a white foam: R$_f$=0.39 (10% CH$_3$OH in CH$_2$Cl$_2$); IR (cm$^{-1}$) 3306, 1712, 1661; $^1$H NMR (CDCl$_3$, approximately 1:1 mixture of diastereomers) δ 0.87–0.93 (m), 1.24–1.33 (m), 1.39–1.96 (m), 2.17–2.21 (m), 2.58–2.79 (m), 2.87–3.09 (m), 4.10–4.27 (m), 4.44 (s, br), 4.55 (s, br), 5.01–5.10 (m), 5.14–5.69 (m), 5.79 (s), 5.82–5.91 (m), 6.13 (d, J=7.5 Hz), 6.42 (s, br), 6.59 (dd, J=16.0, 7.5 Hz), 6.74 (dd, J=15.6, 4.7 Hz), 7.16–7.39 (m); Anal. (C$_{33}$H$_{43}$N$_3$O$_7$) C, H, N.

EXAMPLE 2

Preparation of Compound 1: Ethyl-3-(CBZ-l-LeuΨ[COCH$_2$]-l-Phe-l-Gln)-e-Propenoate Preparation of Intermediate trans-7-Methyl-oct-4-enoic Acid.

A solution of isovaleraldehyde (8.61 g, 100 mmol, 1 equiv) in THF (30 mL) was added dropwise via addition funnel to a solution of vinylmagnesium bromide (100 mL of a 1.0 M solution in THF, 100 mmol, 1.0 equiv) in THF (150 mL) at 0° C. After the addition was completed, the reaction mixture was stirred for 30 minutes at 0° C., and then was partitioned between saturated NH$_4$Cl (150 mL) and Et$_2$O (2×150 mL). The combined organic layers were dried over Na$_2$SO$_4$ and concentrated to afford a yellow oil. This material was combined (neat) with diethyl malonate (16.7 mL, 110 mmol, 1.1 equiv) and Ti(OEt)$_4$ (2.10 mL, 10.0 mmol, 0.10 equiv), and the combination was heated to 160° C. for 1 hour (distilling out EtOH as it was formed). The reaction mixture was then maintained at 190° C. for 4 hours and then cooled to 60° C. EtOH (50 mL) and 6.0 M KOH (50 mL) were added sequentially, and the brown reaction mixture was refluxed for 4 hours. After cooling to 23° C., the reaction mixture was filtered through a medium frit, and the filtrate was partitioned between water (150 mL) and Et$_2$O (2×150 mL). The aqueous layer was then acidified to pH=2 (as indicated by pH paper) with concentrated HCl and extracted with a 1:1 mixture of EtOAc and hexanes (2×150 mL). The combined organic layers were dried over Na$_2$SO$_4$, concentrated, and the residue was distilled at reduced pressure to afford trans-7-methyl-oct-4-enoic acid (4.62 g, 30%) as a colorless liquid: bp: 115–120° C. (1 torr); $^1$H NMR (CDCl$_3$) δ 0.86 (d, 6H, J=5.5), 1.51–1.65 (m, 1H), 1.87 (t, 2H, J=6.5), 2.22–2.38 (m, 2H), 2.40–2.45 (m, 2H), 5.34–5.52 (m, 2H); Anal. (C$_9$H$_{16}$O$_2$) C, H.

Preparation of Intermediate trans-7-Methyl-oct-4-enoic Acid (2R-Hydroxy-1R-methyl-2-phenyl-ethyl)-methyl Amide.

Oxalyl chloride (2.71 mL, 31.1 mmol, 1.05 equiv) was added to a solution of trans-7-methyl-oct-4-enoic acid (4.62 g, 29.6 mmol, 1 equiv) and N,N-dimethylformamide (0.03 mL, 0.39 mmol, 0.012 equiv) in benzene (100 mL) at 23° C. The reaction mixture was stirred at 23° C. for 2 hours and then concentrated under reduced pressure. The resulting oil was dissolved in THF (20 mL) and added via cannula to a solution of (1R,2R)-(-)-pseudoephedrine (4.45 g, 26.9 mmol, 0.91 equiv) and triethylamine (4.50 mL, 32.3 mmol, 1.1 equiv) in THF (200 mL) at 0° C. The reaction mixture was stirred at 0° C. for 30 minutes and then partitioned between half-saturated NH$_4$Cl (150 mL) and EtOAc (2×150 mL). The combined organic layers were dried over Na$_2$SO$_4$, concentrated, and the residue purified by flash column chromatography (gradient elution 40→50% EtOAc in hexanes) to afford trans-7-methyl-oct-4-enoic acid (2R-hydroxy-1R-methyl-2-phenyl-ethyl)-methyl amide (7.55 g, 93%) as a viscous oil: R$_f$=0.27 (50% EtOAc in hexanes); IR (cm$^{-1}$) 3382, 1622; $^1$H NMR (CDCl$_3$, mixture of rotamers) δ 0.87 (d, J=6.5), 0.99 (d, J=6.8), 1.11 (d, J=7.2), 1.53–1.66 (m), 1.86 (t, J=6.1), 2.26–2.54 (m), 2.82 (s), 2.92 (s), 3.99–4.04 (m), 4.29 (s, br), 4.42–4.47 (m), 4.56–4.62 (m), 5.37–5.51 (m), 7.26–7.36 (m); Anal. (C$_{19}$H$_{29}$NO$_2$) C, H, N.

Preparation of Intermediate trans-2S-Benzyl-7-methyl-oct-4-enoic Acid (2R-Hydroxy-1R-methyl-2-phenyl-ethyl)-methyl Amide.

n-Butyllithium (52.6 mL of a 1.6 M solution in hexanes, 84.2 mmol, 2.1 equiv) was added to a suspension of anhydrous lithium chloride (11.9 g, 282 mmol, 7.0 equiv) and diisopropylamine (12.7 mL, 90.3 mmol, 2.25 equiv) in THF (300 mL) at -78° C. The reaction mixture was stirred for 20 minutes at -78° C. and then maintained at 0° C. for 5 minutes and subsequently cooled again to -78° C. trans-7-Methyl-oct-enoic acid (2R-hydroxy-1R-methyl-2-phenyl-ethyl)-methyl amide (12.2 g, 40.1 mmol, 1 equiv) in THF (40 mL) was added via cannula, and the resulting solution was stirred at -78° C. for 1 hour, maintained at 0° C. for 15 minutes, stirred at 23° C. for 5 minutes, and then cooled again to 0° C. Benzyl bromide (7.15 mL, 60.1 mmol, 1.5 equiv) was added, and the reaction mixture was stirred at 0° C. for 30 minutes and then partitioned between half-saturated NH$_4$Cl (200 mL) was a 1:1 mixture of EtOAc and hexanes (2×200 mL). The combined organic layers were dried over Na$_2$SO$_4$ and concentrated. Purification of the residue by flash column chromatography (gradient elution 20→40% EtOAc in hexanes) provided trans-2S-benzyl-7-methyl-oct-4-enoic acid (2R-hydroxy-1R-methyl-2-phenyl-ethyl)-methyl amide (12.0 g, 76%) as a viscous oil: R$_f$=0.54 (50% EtOAc in hexanes); IR (cm$^{-1}$) 3382, 1617; $^1$H NMR (CDCl$_3$, mixture of rotamers) δ 0.81–0.90 (m), 1.42–1.61 (m), 1.80–1.95 (m), 2.17–2.25 (m), 2.33–2.54 (m), 2.55 (s), 2.73–2.99 (m), 3.05–3.16 (m), 3.93–4.00 (m), 4.31–4.51 (m), 5.25–5.56 (m), 7.14–7.37 (m); Anal. (C$_{26}$H$_{35}$NO$_2$) C, H, N.

Preparation of Intermediate 3R-Benzyl-5S-(1R-bromo-3-methyl-butyl)-dihydrofuran-2-one.

N-Bromosuccinimide (5.97 g, 33.5 mmol, 1.1 equiv) was added in small portions over 5 minutes to a solution of trans-2S-benzyl-7-methyl-oct-4-enoic acid (2R-hydroxy-1R-methyl-2-phenyl-ethyl)-methyl amide (12.0 g, 30.5 mmol, 1 equiv) and glacial acetic acid (8.73 mL, 152 mmol, 5.0 equiv) in a 4:1 mixture of THF and H$_2$O (250 mL) at 0° C. The resulting yellow solution was stirred for 15 minutes at 0° C., then warmed to 23° C., and subsequently refluxed for 1 hour. After cooling to 23° C., the reaction mixture was partitioned between half-saturated NaHCO$_3$ (300 mL) and a 1:1 mixture of EtOAc and hexanes (2×200 mL). The combined organic layers were dried over Na$_2$SO$_4$ and concentrated. Flash chromatographic purification of the residue (5% EtOAc in hexanes) gave 3R-benzyl-5S-(1R-bromo-3-methyl-butyl)-dihydrofuran-2-one (7.09 g, 65%) as a pale yellow oil: R$_f$=0.79 (30% EtOAc in hexanes); IR (cm$^{-1}$) 1777; $^1$H NMR (CDCl$_3$) δ 0.87 (d, 3H, J=6.5), 0.94 (d, 3H, J=6.9), 1.53–1.72 (m, 2H), 1.82–1.93 (m, 1H), 2.10–2.20 (m, 1H), 2.23–2.33 (m, 1H), 2.83 (dd, 1H, J=13.5, 8.9), 3.04–3.12 (m, 1H), 3.14–3.22 (m, 1H), 4.05–4.12 (m, 1H), 4.23–4.29 (m, 1H), 7.20–7.36 (m, 5H); Anal. (C$_{16}$H$_{21}$BrO$_2$) C, H, N.

Preparation of Intermediate 5S-(1S-Azido-3-methyl-butyl)-3R-benzyl-dihydrofuran-2-one.

A suspension of sodium azide (2.83 g, 43.5 mmol, 2.0 equiv) and 3R-benzyl-5S-(1R-bromo-3-methyl-butyl)-dihydrofuran-2-one (7.09 g, 21.8 mmol, 1 equiv) in N,N-dimethylformamide (50 mL) was heated at 50° C. for 20 hours. The reaction mixture was cooled to 23° C. and partitioned between water (200 mL) and a 1:1 mixture of EtOAc and hexanes (2×200 mL). The combined organic layers were dried over $Na_2SO_4$, concentrated, and the residue purified by flash column chromatography (10% EtOAc in hexanes) to give 5S-(1S-azido-3-methyl-butyl)-3R-benzyl-dihydrofuran-2-one (3.26 g, 52%) as a colorless oil: $R_f$=0.47 (20% EtOAc in hexanes); IR (cm$^{-1}$) 2109, 1775; $^1$H NMR (CDCl$_3$) δ 0.93 (d, 3H, J=6.5), 0.94 (d, 3H, J=6.5), 1.32–1.41 (m, 1H), 1.55–1.65 (m, 1H), 1.70–1.85 (m, 1H), 2.03–2.18 (m, 2H), 2.80 (dd, 1H, J=13.5, 8.9), 3.05–3.22 (m, 2H), 3.27–3.33 (m, 1H), 4.22–4.27 (m, 1H), 7.18–7.36 (m, 5H); Anal. ($C_{16}H_{21}N_3O_2$) C, H, N.

Preparation of Intermediate [1S-(4R-Benzyl-5-oxo-tetrahydrofuran-2S-yl)-3-methyl-butyl]-carbamic Acid tert-Butyl Ester.

A suspension of 5S-(1S-azido-3-methyl-butyl)-3R-benzyl-dihydrofuran-2-one (3.26 g, 11.3 mmol, 1 equiv) and Pd/C (10%, 0.40 g) in CH$_3$OH (60 mL) was stirred under a hydrogen atmosphere (balloon) for 2 hours. The reaction mixture was filtered through celite, concentrated, and the residue dissolved in 1,4-dioxane (80 mL). N,N-diisopropylethylamine (3.94 mL, 22.6 mmol, 2.0 equiv) and di-tert-butyl dicarbonate (3.70 g, 17.0 mmol, 1.5 equiv) were added sequentially, and the resulting solution was stirred at 23° C. for 2 hours. The reaction mixture was then partitioned between water (150 mL) and a 1:1 mixture of EtOAc and hexanes (2×150 mL). The combined organic layers were dried over $Na_2SO_4$ and concentrated. Purification of the residue by flash column chromatography (gradient elution, 10→15% EtOAc in hexanes) provided [1S-(4R-benzyl-5-oxo-tetrahydrofuran-2S-yl)-3-methyl-butyl]-carbamic acid tert-butyl ester (2.53 g, 62%) as a white solid: mp=84–86° C.; $R_f$=0.66 (30% EtOAc in hexanes); IR (cm$^{-1}$) 3338, 1767, 1704; $^1$H NMR (CDCl$_3$) δ 0.89 (d, 3H, J=6.5), 0.90 (d, 3H, J=6.5), 1.18–1.32 (m, 1H), 1.40 (s, 9H), 1.43–1.56 (m, 1H), 1.98–2.07 (m, 1H), 2.20–2.29 (m, 1H), 2.78 (dd, 1H, J=13.7, 9.0), 2.91–3.01 (m, 1H), 3.15 (dd, 1H, J=13.7, 4.4), 3.71–3.81 (m, 1H), 4.23–4.28 (m, 1H), 4.34 (d, 1H, J=9.7), 7.16–7.33 (m, 6H); Anal. ($C_{21}H_{31}NO_4$) C, H, N.

Preparation of Intermediate Ethyl-3-[BOC-L-LeuΨ[COCH$_2$]-L-(Tr-Gln)]-E-Propenoate.

Lithium hydroxide (7.2 mL of a 1 M aqueous solution, 7.2 mmol, 5.0 equiv) was added to a solution of [1S-(4R-benzyl-5-oxo-tetrahydrofuran-2S-yl)-3-methyl-butyl]-carbamic acid tert-butyl ester (0.521 g, 1.44 mmol, 1 equiv) in DME (7 mL) at 23° C. The resulting suspension was stirred at 23° C. for 30 minutes and then partitioned between 0.5 M HCl (100 mL) and EtOAc (2×100 mL). The combined organic layers were dried over $Na_2SO_4$, concentrated, and the residue dissolved in CH$_2$Cl$_2$ (30 mL). 4-Methylmorpholine N-oxide (0.337 g, 2.88 mmol, 2.0 equiv), powdered 4 Å molecular sieves (0.55 g), and tetrapropylammonium perruthenate (0.050 g, 0.142 mmol, 0.10 equiv) were added sequentially. The resulting dark reaction mixture was stirred for 2.5 hours at 23° C., and then it was filtered through celite. The filtrate was concentrated under reduced pressure to provide a brown oil which was dissolved in CH$_2$Cl$_2$ (30 mL). Crude ethyl-3-[H$_2$H-L-(Tr-Gln)]-E-propenoate●HCl (2.87 mmol, 2.0 equiv, prepared as described in Example 1 for the preparation of ethyl-3-[CBZ-L-LeuΨ[COCH$_2$]-D/L-Phe-L-(Tr-Gln)]-E-propenoate), 1-hydroxybenzotriazole hydrate (0.409 g, 3.03 mmol, 2.1 equiv), 4-methylmorpholine (0.633 mL, 5.76 mmol, 4.0 equiv), and 1-(3-dimethylaminopropyl)-3-ethylcarbodiimide hydrochloride (0.58 g, 3.03 mmol, 2.1 equiv) were added sequentially, and the reaction mixture was stirred for 15 hours at 23° C. and then partitioned between water (150 mL) and EtOAc (2×150 mL). The combined organic layers were dried over $Na_2SO_4$ and concentrated. Purification of the residue by flash column chromatography (gradient elution 30→40% EtOAc in hexanes) provided ethyl-3-[BOC-L-LeuΨ[COCH$_2$]-L-Phe-L-(Tr-Gln)]-E-propenoate (0.502 g, 44%) as a white foam: $R_f$0.49 (50% EtOAc in hexanes); IR (cm$^{-1}$) 3314, 1707, 1667; $^1$H NMR (CDCl$_3$) δ 0.84–0.91 (m, 6H), 1.29 (t, 3H, J=7.2); 1.39 (s, 9H), 1.42–1.61 (m, 4H), 1.98–2.05 (m, 1H), 2.35 (t, 2H, J=7.2), 2.54 (d, 1H, J=16.2), 2.70 (dd, 1H, J=11.5, 5.6), 2.78–2.99 (m, 3H), 4.07–4.10 (m, 1H), 4.17 (q, 2H, J=7.2), 4.47 (s, br, 1H), 4.58 (d, 1H, J=7.5), 5.46 (d, 1H, J=15.8), 5.87 (d, 1H, J=8.7), 6.58 (dd, 1H, J=15.8, 5.1), 7.12–7.31 (m, 21H); Anal. ($C_{49}H_{59}N_3O_7$) C, H, N.

Preparation of Intermediate Ethyl-3-[CBZ-L-LeuΨ[COCH$_2$]-L-Phe-L-(Tr-Gln)]-E-Propenoate.

HCl (5 mL of a 4.0 M solution in 1,4-dioxane) was added to a solution of ethyl-3-[BOC-L-LeuΨ[COCH$_2$]-L-Phe-L-(Tr-Gln)]-E-Propenoate (0.096 g, 0.120 mmol, 1 equiv) in 1,4-dioxane (5 mL). The reaction mixture was stirred at 23° C. for 30 minutes and then concentrated. The resulting oil was dissolved in CH$_2$Cl$_2$ (10 mL), and 4-methylmorpholine (0.033 mL, 0.300 mmol, 2.5 equiv) and benzyl chloroformate (0.025 mL, 0.175 mmol, 1.4 equiv) were added sequentially. The reaction mixture was stirred for 30 minutes at 23° C. and then partitioned between water (100 mL) and a 1:1 mixture of EtOAc and hexanes (2×100 mL). The combined organic layers were dried over $Na_2SO_4$, concentrated, and the residue was chromatographed on silica gel (40% EtOAc in hexanes) to afford ethyl-3-[CBZ-L-LeuΨ[COCH$_2$]-L-Phe-L-(Tr-Gln)]-E-propenoate (0.050 g, 50%) as a white foam: $R_f$=0.38 (50% EtOAc in hexanes); IR (cm$^{-1}$) 3318, 1712, 1664; $^1$H NMR (CDCl$_3$) δ 0.85–0.87 (m, 6H), 1.05–1.13 (m, 1H), 1.29 (t, 3H, J=7.2); 1.35–1.42 (m, 2H), 1.97 (s, br, 1H), 2.29–2.31 (m, 2H), 2.54 (d, 1H, J=16.5), 2.69–3.03 (m, 5H), 4.17 (q, 2H, J=7.2), 4.47 (s, br, 1H), 4.81 (d, 1H, J=7.5), 4.94–5.06 (m, 3H), 5.48 (d, 1H, J=15.6), 5.87 (d, 1H, J=8.1), 6.58 (dd, 1H, J=15.6, 5.0), 7.12–7.32 (m, 26H); Anal. ($C_{52}H_{57}N_3O_7$●0.25 H$_2$O) C, H, N.

Preparation of Product Ethyl-3-(CBZ-L-LeuΨ[COCH$_2$]-L-Phe-L-Gln)-E-Propenoate.

Triisopropylsilane (0.10 mL) and trifluoroacetic acid (5 mL) were added sequentially to a solution of ethyl-3-[CBZ-L-LeuΨ[COCH$_2$]-L-Phe-L-(Tr-Gln)]-E-propenoate (0.050 g, 0.060 mmol) in CH$_2$Cl$_2$ (6 mL) producing a bright yellow solution. The reaction mixture was stirred for 30 minutes at 23° C., then carbon tetrachloride (4 mL) was added, and the mixture was concentrated under reduced pressure. The residue was purified by flash column chromatography (5% CH$_3$OH in CH$_2$Cl$_2$) to afford ethyl-3-(CBZ-L-LeuΨ[COCH$_2$]-L-Phe-L-Gln)-E-propenoate (0.026 g, 73%) as a white solid: mp=162–164° C.; $R_f$=0.66 (10% CH$_3$OH in CH$_2$Cl$_2$); IR (cm$^{-1}$) 3412, 3292, 1718, 1689, 1650; $^1$H NMR (CDCl$_3$) δ 0.92 (d, 6H, J=6.5), 1.30 (t, 3H, J=7.2), 1.45–1.59 (m, 3H), 1.97–2.05 (m, 1H), 2.07 (d, 1H, J=15.9), 2.17 (s, br, 2H), 2.70–2.79 (m, 1H), 2.91–3.09 (m, 3H), 4.18 (q, 2H, J=7.2), 4.23–4.27 (m, 1H), 4.54 (s, br, 1H), 5.03 (d, 1H, J=12.1), 5.08 (d, 1H, J=12.1), 5.23 (d, 1H, J=6.9), 5.38 (s, br, 1H), 5.47 (d, 1H, J=15.6), 5.92 (d, 1H, J=8.7), 6.43 (s, br, 1H), 6.60 (dd, 1H, J=15.6, 4.8), 7.16–7.39 (m, 11H); Anal. ($C_{33}H_{43}N_3O_7$) C, H, N.

EXAMPLE 3

Preparation of Compound 2: Ethyl-3-(EtSCO-L-LeuΨ[COCH$_2$]-L-Phe-L-Gln)-E-Propenoate.

Preparation of Intermediate Ethyl-3-[EtSCO-L-LeuΨ[COCH$_2$]-L-Phe-L-(Tr-Gln)]-E-Propenoate.

HCl (4 mL of a 4.0 M solution in 1,4-dioxane) was added to a solution of ethyl-3-[BOC-L-LeuΨ[COCH$_2$]-L-Phe-L-(Tr-Gln)]-E-propenoate (0.216 g, 0.269 mmol, 1 equiv) in 1,4-dioxane (6 mL). The reaction mixture was stirred at 23° C. for 1.5 hours and then concentrated. The resulting oil was dissolved in $CH_2Cl_2$ (6 mL), cooled to 0° C., and N,N-diisopropylethylamine (0.094 mL, 0.540 mmol, 2.0 equiv) and ethyl chlorothiolformate (0.034 mL, 0.326 mmol, 1.2 equiv) were added sequentially. The reaction mixture was stirred for 1 hour at 0° C., and it then was partitioned between water (100 mL) and EtOAc (2×100 mL). The combined organic layers were dried over $Na_2SO_4$, concentrated, and the residue was purified by flash column chromatography (40% EtOAc in hexanes) to afford ethyl-3-[EtSCO-L-LeuΨ[$COCH_2$]-L-Phe-L-(Tr-Gln)]-E-propenoate (0.130 g, 61%) as a white foam: $R_f$=0.45 (50% EtOAc in hexanes); IR ($cm^{-1}$) 3307, 1713, 1656; $^1H$ NMR ($CDCl_3$) δ 0.86 (d, 6H, J=6.5) 1.05–1.19 (m, 1H), 1.21–1.39 (m, 8H), 1.41–1.58 (m, 2H), 1.96–2.05 (m, 1H), 2.28–2.35 (m, 2H), 2.54 (d, 1H, J=14.6), 2.70 (dd, 1H, J=11.7, 5.8), 2.79–3.00 (m, 4H), 4.17 (q, 2H, J=7.2), 4.41–4.45 (m, 2H), 5.40 (d, 1H, J=7.5), 5.49 (dd, 1H, J=15.8, 1.6), 5.93 (d, 1H, J=8.4), 6.59 (dd, 1H, J=15.8, 5.1), 7.10–7.31 (m, 21H); Anal. ($C_{47}H_{55}N_3O_6S$) C, H, N.

Preparation of Product Ethyl-3-(EtSCO-L-LeuΨ[$COCH_2$]-L-Phe-L-Gln)-E-Propenoate Ethyl-3-[EtSCO-L-LeuΨ[$COCH_2$]-L-Phe-L-(Tr-Gln)]-E-propenoate (0.120 g, 0.152 mmol) was dissolved in $CH_2Cl_2$ (5 mL), and triisopropylsilane (0.10 mL) and trifluoroacetic acid (5 mL) were added sequentially producing a bright yellow solution. The reaction mixture was stirred for 30 minutes at 23° C., then carbon tetrachloride (6 mL) was added, and the mixture was concentrated under reduce pressure. The residue was purified by flash column chromatography (5% $CH_3OH$ in $CH_2Cl_2$) to afford ethyl-3-(EtSCO-L-LeuΨ[$COCH_2$]-L-Phe-L-Gln)-E-propenoate (0.056 g, 68%) as a beige foam: $R_f$0.55 (10% $CH_3OH$ in $CH_2Cl_2$); IR ($cm^{-1}$) 3385, 2293, 3199, 1717, 1653; $^1H$ NMR ($CDCl_3$) δ 0.91 (d, 3H, J=6.2), 0.92 (d, 3H, J=6.5), 1.21–1.38 (m, 8H), 1.46–1.65 (m, 2H), 1.83–2.05 (m, 1H), 2.61 (d, 1H, J=14.9), 2.74–3.09 (m, 7H), 4.18 (q, 2H, J=7.2), 4.49–4.56 (m, 2H), 5.49 (d, 1H, J=15.6), 5.59 (s, br, 1H), 6.05 (d, 1H, J=8.7), 6.20 (d, 1H, J=6.9), 6.49 (s, br, 1H), 6.62 (dd, 1H, J=15.6, 4.8), 7.16–7.32 (m, 6H); Anal. ($C_{28}H_{41}N_3O_6S$) C, H, N.

EXAMPLE 4

Preparation of Compound 6; Ethyl-3-(BnSCO-L-LeuΨ[$COCH_2$]-L-Phe-L-Gln)-E-Propenoate.

Preparation of Intermediate Benzyl Chlorothiolformate

Triethylamine (7.12 mL, 51.1 mmol, 1.0 equiv) was added to a 0° C. solution of benzyl mercaptan (6.0 mL, 51.1 mmol, 1 equiv) and triphosgene (5.76 g, 19.4 mmol, 0.38 equiv) in $CH_2Cl_2$ (100 mL). The reaction mixture was warmed to 23° C., stirred for 2 hours, and then concentrated under reduced pressure. The resulting white suspension was slurried with $Et_2O$ (100 mL) and filtered through a medium frit. The filtrate was concentrated under reduced pressure, and the resulting liquid was distilled under vacuum to provide benzyl chlorothiolformate (6.95 g, 73%) as a colorless liquid: bp=95–100° C. (8 torr); IR ($cm^{-1}$) 1755; $^1H$ NMR ($CDCl_3$) δ 4.19 (s, 2H), 7.30–7.34 (m, 5H).

Preparation of Intermediate Ethyl-3-[BnSCO-L-LeuΨ[$COCH_2$]-L-Phe-L-(Tr-Gln)]-E-Propenoate.

HCl (5 mL of a 4.0 M solution in 1,4-dioxane) was added to a solution of ethyl-3-[BOC-L-LeuΨ[$COCH_2$]-L-Phe-L-(Tr-Gln)]-E-propenoate (0.190 g, 0.237 mmol, 1 equiv) in 1,4-dioxane (5 mL). The reaction mixture was stirred at 23° C. for 1.5 hours and then concentrated. The resulting oil was dissolved in $CH_2Cl_2$ (6 mL), and 4-methylmorpholine (0.078 mL, 0.709 mmol, 3.0 equiv) and benzyl chlorothiolformate (0.050 mL, 0.331 mmol, 1.4 equiv) were added sequentially. The reaction mixture was stirred for 1.5 hours at 23° C., and it then was partitioned between water (100 mL) and a 1:1 mixture of EtOAc and hexanes (2×100 mL). The combined organic layers were dried over $Na_2SO_4$, concentrated, and the residue was chromatographed on silica gel (40% EtOAc in hexanes) to afford ethyl-3-[BnSCO-L-LeuΨ[$COCH_2$]-L-Phe-L-(Tr-Gln)]-E-propenoate (0.117 g, 58%) as a white foam: $R_f$=0.44 (50% EtOAc in hexanes); IR ($cm^{-1}$) 3312, 1714, 1656; $^1H$ NMR ($CDCl_3$) δ 0.82–0.89 (m, 6H), 1.28 (t, 3H, J=7.2), 1.43–1.57 (m, 2H), 1.95–2.05 (m, 1H), 2.31–2.36 (m, 2H), 2.53 (d, 1H, J=14.6), 2.56–2.70 (m, 1H), 2.72–3.04 (m, 5H), 4.02–4.21 (m, 4H), 4.44 (s, br, 2H), 5.41 (d, 1H, J=7.5), 5.48 (dd, 1H, J=15.8, 1.6), 5.88 (d, 1H, J=8.1), 6.58 (dd, 1H, J=15.8, 5.1), 7.08–7.31 (m, 26H); Anal. ($C_{52}H_{57}N_3O_6S$) C, H, N.

Preparation of Product Ethyl-3-(BnSCO-L-LeuΨ[$COCH_2$]-L-Phe-L-Gln)-E-Propenoate Ethyl-3-[BnSCO-L-LeuΨ[$COCH_2$]-L-Phe-L-(Tr-Gln)]-E-propenoate (0.117 g, 0.137 mmol) was dissolved in $CH_2Cl_2$ (5 mL), and triisopropylsilane (0.10 mL) and trifluoroacetic acid (5 mL) were added sequentially producing a bright yellow solution. The reaction mixture was stirred for 20 minutes at 23° C., then carbon tetrachloride (5 mL) was added, and the mixture was concentrated under reduced pressure. The residue was purified by flash column chromatography (5% $CH_3OH$ in $CH_2Cl_2$) to afford ethyl-3-(BnSCO-L-LeuΨ[$COCH_2$]-L-Phe-L-Gln)-E-propenoate (0.068 g, 81%) as a white foam: $R_f$32 0.52 (10% $CH_3OH$ in $CH_2Cl_2$); IR ($cm^{-1}$) 3299, 1717, 1650; $^1H$ NMR ($CDCl_3$) δ 0.91 (d, 6H, J=6.2), 1.29 (t, 3H, J=7.2), 1.36–1.63 (m, 3H), 1.80 (s, br, 1H), 1.94–2.05 (m, 1H), 2.16–2.18 (m, 2H), 2.60 (d, 1H, J=16.5), 2.69–2.78 (m, 1H), 2.87–3.13 (m, 3H), 4.05–4.21 (m, 4H), 4.52 (s, br, 2H), 5.47 (d, 1H, J=15.6), 5.57 (s, 1H), 6.06 (d, 1H, J=8.7), 6.32 (d, 1H, J=7.2), 6.40 (s, 1H), 6.60 (dd, 1H, J=15.6, 4.5), 7.15–7.29 (m, 10H); Anal. ($C_{33}H_{43}N_3O_6S$) C, H, N.

EXAMPLE 5

Preparation of Compound 8: Ethyl-3-(CyPentylSCO-L-LeuΨ[$COCH_2$]-L-Phe-L-Gln)-E-Propenoate.

Preparation of Intermediate Cyclopentyl Chlorothiolformate.

Triethylamine (10.4 mL, 74.6 mmol, 1.0 equiv) was added to a 0° C. solution of cyclopentyl mercaptan (8.0 mL, 74.8 mmol, 1 equiv) and triphosgene (8.43 g, 28.4 mmol, 0.38 equiv) in $CH_2Cl_2$. The reaction mixture was warmed to 23° C., stirred for 2 hours, and then concentrated under reduced pressure. The resulting white suspension was slurried with $Et_2O$ (100 mL) and filtered through a medium frit. The filtrate was concentrated under reduced pressure, and the resulting liquid was distilled under vacuum to provide cyclopentyl chlorothiolformate (10.4 g, 85%) as a colorless liquid: bp=70–74° C. (1 torr); IR ($cm^{-1}$) 1756, 830; $^1H$ NMR ($C_6D_6$) δ 1.01–1.23 (m, 6H), 1.49–1.60 (m, 2H), 3.20–3.29 (m, 1H).

Preparation of Intermediate Ethyl-3-[CyPentylSCO-L-LeuΨ[$COCH_2$]-L-Phe-L-(Tr-Gln)]-E-Propenoate HCl (5 mL of a 4.0 M solution in 1,4-dioxane) was added to a solution of ethyl-3-[BOC-L-LeuΨ[$COCH_2$]-L-Phe-L-(Tr-Gln)]-E-propenoate (0.205 g, 0.256 mmol, 1 equiv) in 1,4-dioxane (6 mL). The reaction mixture was stirred at 23° C. for 1.5 hours and then concentrated. The resulting oil was dissolved in $CH_2Cl_2$ (8 mL), cooled to 0° C., and 4-methylmorpholine (0.070 mL, 0.637 mmol, 2.5 equiv) and cyclopentyl chlorothiolformate (0.063 mL, 0.383 mmol, 1.5 equiv) were added sequentially. The reaction mixture was stirred for 30 minutes at 0° C., and then partitioned between water (100 mL) and a 1:1 mixture of EtOAc and hexanes (2×100 mL). The combined organic layers were dried over $Na_2SO_4$, concentrated, and the residue was chromatographed on silica gel (40% EtOAc in hexanes) to provide ethyl-3-[CyPentylSCO-L-LeuΨ[COCH$_2$]-L-Phe-L-(Tr-Gln)]-E-propenoate (0.113 g, 53%) as a white foam: $R_f$=0.44 (50% EtOAc in hexanes); IR (cm$^{-1}$) 3310, 1713, 1654; $^1$H NMR (CDCl$_3$) δ 0.85 (d, 6H, J=6.5), 1.02–1.12 (m, 1H), 1.29 (t, 3H, J=7.2), 1.42–1.68 (m, 7H), 1.98–2.08 (m, 4H), 2.31–2.35 (m, 2H), 2.55 (d, 1H, J=14.3), 2.70 (dd, 1H, J=11.8, 5.9), 2.79–3.09 (m, 4H), 3.55–3.66 (m, 1H), 4.17 (q, 2H, J=7.2), 4.38 (s, br, 1H), 4.48–4.49 (m, 1H), 5.33 (d, 1H, J=7.5), 5.50 (dd, 1H, J=15.9, 1.6), 5.94 (d, 1H, J=8.4), 6.60 (dd, 1H, J=15.9, 5.0), 7.10–7.31 (m, 21H); Anal. ($C_{50}N_{59}N_3O_6S$) C, H, N.

Preparation of Product Ethyl-3-(CyPentylSCO-L-LeuΨ[COCH$_2$]-L-Phe-L-Gln)-E-Propenoate Ethyl-3-[CyPentylSCO-L-LeuΨ[COCH$_2$]-L-Phe-L-(Tr-Gln)]-E-propenoate (0.090 g, 0.108 mmol) was dissolved in CH$_2$Cl$_2$ (6 mL), and triisopropylsilane (0.10 mL) and trifluoroacetic acid (5 mL) were added sequentially producing a bright yellow solution. The reaction mixture was stirred for 20 minutes at 23° C., then carbon tetrachloride (4 mL) was added, and the mixture was concentrated under reduced pressure. The residue was purified by flash column chromatography (5% CH$_3$OH in CH$_2$Cl$_2$) to provide ethyl-3-(CyPentylSCO-L-LeuΨ[COCH$_2$]-L-Phe-L-Gln)-E-propenoate (0.050 g, 79%) as a white foam: $R_f$32 0.58 (10% CH$_3$OH in CH$_2$Cl$_2$); IR (cm$^{-1}$) 3385, 3298, 3199, 1717, 1652; $^1$H NMR (CDCl$_3$) δ 0.89–0.93 (m, 6H), 1.31 (t, 3H, J=7.2), 1.40–1.69 (m, 8H), 1.86 (s, br, 1H), 2.04–2.09 (m, 4H), 2.21 (s, br, 2H), 2.58 (d, 1H, J=9.3), 2.64–2.79 (m, 1H), 2.89–3.07 (m, 3H), 3.07–3.69 (m, 1H), 4.18 (q, 2H, J=7.2), 4.47 (s, br, 1H), 4.56 (s, br, 1H), 5.49 (d, 1H, J=15.2), 5.57 (s, br, 1H), 6.07 (d, 1H, J=8.7), 6.15 (d, 1H, J=6.9), 6.54 (s, br, 1H), 6.62 (dd, 1H, J=15.2, 4.8), 7.16–7.33 (m, 5H); Anal. ($C_{31}H_{45}N_3O_6S$) C, H, N.

EXAMPLE 6

Preparation of Compound 4: Ethyl-3-(EtSCO-L-ValΨ[COCH$_2$]-L-Phe-L-Gln)-E-Propenoate.

Preparation of Intermediate trans-6-Methyl-hept-4-enoic Acid

A solution of isobutyraldehyde (9.59 g, 133 mmol, 1 equiv) in THF (50 mL) was added dropwise via addition funnel to a solution of vinylmagnesium bromide (133 mL of a 1.0 M solution in THF, 133 mmol, 1.0 equiv) in THF (300 mL) at 0° C. Upon completion of the addition, the reaction mixture was stirred for 30 minutes at 0° C., then ethyl malonyl chloride (17.0 mL, 133 mmol, 1.0 equiv) was added. After stirring for 1 hour at 0° C., the reaction mixture was partitioned between saturated NH$_4$Cl (150 mL) and a 1:1 mixture of EtOAc and hexanes (2×200 mL). The combined organic layers were dried over Na$_2$SO$_4$ and concentrated. Purification of the residue by filtration through silica gel (eluting with 5% EtOAc in hexanes) afforded the intermediate malonate ester (11.5 g, 40% yield). This material was not characterized, but was combined (neat) with Ti(OEt)$_4$ (1.13 mL, 5.39 mmol, 0.10 equiv), heated to 190° C. for 4 hours, and then cooled to 60° C. EtOH (50 mL) and 6.0 M KOH (50 mL) were added sequentially, and the brown reaction mixture was refluxed for 4 hours. After cooling to 23° C., the reaction mixture was filtered through a medium frit, and the filtrate was partitioned between water (150 mL) and Et$_2$O (2×150 mL). The aqueous layer was then acidified to pH=2 (as indicated by pH paper) with concentrated HCl and extracted with a 1:1 mixture of EtOAc and hexanes (2×150 mL). The combined organic layers were dried over Na$_2$SO$_4$, concentrated, and the residue was distilled at reduced pressure to afford trans-6-methyl-hept-4-enoic acid (3.58 g, 47%) as a colorless liquid: bp: 107–112° C. (1 torr); IR (cm$^{-1}$) 2960, 1711; $^1$H NMR (CDCl$_3$) δ 0.96 (d, 6H, J=6.5) 2,18–2.45 (m, 5H), 5.31–5.50 (m, 2H); Anal. ($C_8H_{14}O_2$) C, H.

Preparation of Intermediate trans-6-Methyl-hept-4-enoic Acid (2R-Hydroxy-1R-methyl-2-phenyl-ethyl)-methyl Amide.

Oxalyl chloride (2.25 mL, 25.8 mmol, 1.05 equiv) was added to a solution of trans-6-methyl-hept-4-enoic acid (3.50 g, 24.6 mmol, 1 equiv) and N,N-dimethylformamide (0.03 mL, 0.39 mmol, 0.016 equiv) in benzene (60 mL) at 23° C. The reaction mixture was stirred at 23° C. for 2 hours and then concentrated under reduced pressure. The resulting oil was dissolved in THF (20 mL) and added via cannula to a solution of 1R,2R-(-)-pseudoephedrine (3.87 g, 23.4 mmol, 1.0 equiv) and triethylamine (3.92 mL, 28.1 mmol, 1.2 equiv) in THF (150 mL) at 0° C. The reaction mixture was stirred at 0° C. for 30 minutes and then partitioned between half-saturated NH$_4$Cl (150 mL) and EtOAc (2×150 mL). The combined organic layers were dried over Na$_2$SO$_4$, concentrated, and the residue purified by flash column chromatography (gradient elution 40→50% EtOAc in hexanes) to afford trans-6-methyl-hept-4-enoic acid (2R-hydroxy-1R-methyl-2-phenyl-ethyl)-methyl amide (6.31 g, 93%) as a viscous oil: $R_f$=0.35 (50% EtOAc in hexanes); IR (cm$^{-1}$) 3382, 1622; $^1$H NMR (CDCl$_3$, mixture of rotamers) δ 0.96 (d, J=6.8), 0.97 (d, J=6.5), 1.11 (d, J=6.9), 2.18–2.59 (m), 2.82 (s), 2.92 (s), 3.99–4.04 (m), 4.32–4.42 (m), 4.44–4.49 (m), 4.55–4.62 (m), 5.32–5.49 (m), 7.24–7.42 (m); Anal. ($C_{18}H_{27}NO_2$) C, H, N.

Preparation of Intermediate trans-2S-Benzyl-6-methyl-hept-4-enoic Acid (2R-Hydroxy-1R-methyl-2-phenyl-ethyl)-methyl Amide.

n-Butyllithium (28.6 mL of a 1.6 M solution in hexanes, 45.8 mmol, 2.1 equiv) was added to a suspension of anhydrous lithium chloride (6.47 g, 153 mmol, 7.0 equiv) and diisopropylamine (6.88 mL, 49.1 mmol, 2.25 equiv) in THF (250 mL) at -78° C. The reaction mixture was stirred for 20 minutes at -78° C., and it then was maintained at 0° C. for 5 minutes and subsequently cooled again to -78° C. trans-6-Methyl-hept-4-enoic acid (2R-hydroxy-1R-methyl-2-phenyl-ethyl)-methyl amide (6.31 g, 21.8 mmol, 1 equiv) in THF (40 mL) was added via cannula, and the resulting solution was stirred at -78° C. for 1 hour, maintained at 0° C. for 15 minutes, stirred at 23° C. for 5 minutes, and then cooled again to 0° C. Benzyl bromide (3.89 mL, 32.7 mmol, 1.5 equiv) was added, the reaction mixture was stirred at 0° C. for 30 minutes, and it then was partitioned between half-saturated NH$_4$Cl (200 mL) and a 1:1 mixture of EtOAc and hexanes (2×200 mL). The combined organic layers were dried over Na$_2$SO$_4$ and concentrated. Purification of the residue by flash column chromatography (gradient elution 20→40% EtOAc in hexanes) provided trans-2S-benzyl-6-methyl-hept-4-enoic acid (2R-hydroxy-1R-methyl-2-phenyl-ethyl)-methyl amide (7.91 g, 96%) as a viscous oil: $R_f$=0.52 (50% EtOAc in hexanes); IR (cm$^{-1}$) 3383, 1616; $^1$H NMR (CDCl$_3$, mixture of rotamers) δ 0.82–0.91 (m), 0.96 (d, J=6.5), 1.24–1.27 (m), 2.14–2.47 (m), 2.56 (s), 2.72–2.99 (m), 3.04–3.15 (m), 3.93–4.00 (m), 4.31–4.51 (m), 5.21–5.39 (m), 5.42–5.55 (m), 7.14–7.37 (m); Anal. ($C_{25}H_{33}NO_2$) C, H, N.

Preparation of Intermediate 3R-Benzyl-5S-(1R-bromo-2-methyl-propyl)-dihydrofuran-2-one.

N-Bromosuccinimide (3.89 g, 21.9 mmol, 1.05 equiv) was added in small portions over 5 minutes to a solution of trans-2S-benzyl-6methyl-hept-4-enoic acid (2R-hydroxy-1R-methyl-2-phenyl-ethyl)-methyl amide (7.90 g, 20.8 mmol, 1 equiv) and glacial acetic acid (5.96 mL, 104 mmol, 5.0 equiv) in a 4:1 mixture of THF and $H_2O$ (250 mL) at 0° C. The resulting yellow solution was stirred for 15 minutes at 0° C., then was warmed to 23° C., and subsequently was refluxed for 1 hour. After cooling to 23° C., the reaction mixture was partitioned between half-saturated $NaHCO_3$ (300 mL) and a 1:1 mixture of EtOAc and hexanes (2×200 mL). The combined organic layers were dried over $Na_2SO_4$ and concentrated. Flash chromatographic purification of the residue (5% EtOAc in hexanes) gave 3R-benzyl-5S-(1R-bromo-2-methyl-propyl)-dihydrofuran-2-one (5.09 g, 79%) as a white solid. Minor impurities were removed by recrystallization from hexanes (2.51 g recovery): mp=75–76° C.; $R_f$=0.64 (30% EtOAc in hexanes); IR ($cm^{-1}$) 1774; $^1H$ NMR ($CDCl_3$) δ 0.93 (d, 3H, J=6.6), 0.99 (d, 3H, J=6.9), 2.05–2.18 (m, 1H), 2.20–2.33 (m, 2H), 2.83 (dd, 1H, J=13.6, 8.7) 2.95–3.05 (m, 1H), 3.17 (dd, 1H, J=13.6, 4.5), 3.89 (dd, 1H, J=9.0, 3.4), 4.32–4.39 (m, 1H), 7.20–7.36 (m, 5H); Anal. ($C_{15}H_{19}BrO_2$) C, H.

Preparation of Intermediate 5S-(1S-Azido-2-methyl-propyl)-3R-benzyl-dihydrofuran-2-one.

A solution of Aliquat-336 (0.163 g, 0.403 mmol, 0.05 equiv) and 3R-benzyl-5S-(1R-bromo-2-methyl-propyl)-dihydrofuran-2-one (2.51 g, 8.06 mmol, 1 equiv) in toluene (60 mL) was treated with a solution of sodium azide (2.10 g, 32.3 mmol, 4.0 equiv) in $H_2O$ (10 mL). The resulting biphasic mixture was heated to 70° C. and maintained at that temperature for 48 hours. The reaction mixture was cooled to 23° C. and partitioned between water (150 mL) and a 1:1 mixture of EtOAc and hexanes (2×150 mL). The combined organic layers were dried over $Na_2SO_4$, concentrated, and the residue purified by flash column chromatography (gradient elution, 5→10% EtOAc in hexanes) to give 5S-(1S-azido-2-methyl-propyl)-3R-benzyl-dihydrofuran-2-one (1.0 g, 45%) as a viscous oil: $R_f$=0.41 (20% EtOAc in hexanes); IR ($cm^{-1}$) 2105, 1772; $^1H$ NMR ($CDCl_3$) δ 0.86–1.04 (m, 7H), 1.95–2.17 (m, 2H), 2.83 (dd, 1H, J=13.2, 8.3), 2.92 (dd, 1H, J=6.4, 4.5), 3.05–3.21 (m, 2H), 4.33–4.38 (m, 1H), 7.19–7.35 (m, 5H); Anal. ($C_{15}H_{19}N_3O_2$) C, H, N.

Preparation of Intermediate [1S-(4R-Benzyl-5-oxo-tetrahydrofuran-2S-yl)-2-methyl-propyl]-carbamic Acid tert-Butyl Ester.

A suspension of 5S-(1S-azido-2-methyl-propyl)-3R-benzyl-dihydrofuran-2-one (1.00 g, 3.66 mmol, 1 equiv) and Pd/C (10%, 0.090 g) in $CH_3OH$ (60 mL) was stirred under a hydrogen atmosphere (balloon) for 1 hour. The reaction mixture was filtered through celite, concentrated, and the residue dissolved in 1,4-dioxane (50 mL). N,N-diisopropylethylamine (1.28 mL, 7.35 mmol, 2.0 equiv) and di-tert-butyl dicarbonate (1.20 g, 5.50 mmol, 1.5 equiv) were added sequentially, and the resulting solution was stirred at 23° C. for 18 hours. The reaction mixture was then partitioned between water (100 mL) and a 1:1 mixture of EtOAc and hexanes (2×150 mL). The combined organic layers were dried over $Na_2SO_4$ and concentrated. Purification of the residue by flash column chromatography (gradient elution, 10→15% EtOAc in hexanes) provided [1S-(4R-benzyl-5-oxo-tetrahydrofuran-2S-yl)-2-methyl-propyl]-carbamic acid tert-butyl ester (0.496 g, 39%) as a colorless oil: $R_f$=0.44 (20% EtOAc in hexanes); IR ($cm^{-1}$) 3340, 1768, 1708; $^1H$ NMR ($CDCl_3$) δ 0.92 (d, 6H, J=6.9), 1.41 (s, 9H), 1.70–1.80 (m, 1H), 1.98–2.07 (m, 1H), 2.14–2.24 (m, 1H), 2.81 (dd, 1H, J=13.6, 8.9), 2.92–3.01 (m, 1H), 3.13 (dd, 1H, J=13.6, 4.4), 3.31–3.38 (m, 1H), 4.39–4.47 (m, 2H), 7.17–7.33 (m, 5H); Anal. ($C_{20}H_{29}NO_4$) C, H, N.

Preparation of Intermediate Ethyl-3-[BOC-L-ValΨ[$COCH_2$]-L-Phe-L-(Tr-Gln)]-E-Propenoate.

Lithium hydroxide (7.14 mL of a 1 M aqueous solution, 7.14 mmol, 5.0 equiv) was added to a solution of [1S-(4R-benzyl-5-oxo-tetrahydrofuran-2S-yl)-2-methyl-propyl]-carbamic acid tert-butyl ester (0.496 g, 1.43 mmol, 1 equiv) in DME (7 mL) at 23° C. The resulting suspension was stirred at 23° C. for 30 minutes and then partitioned between 0.5 M HCl (100 mL) and EtOAc (2×100 mL). The combined organic layers were dried over $Na_2SO_4$, concentrated, and the residue dissolved in $CH_2Cl_2$ (20 mL). 4-Methylmorpholine N-oxide (0.334 g, 2.85 mmol, 2.0 equiv), powdered 4 Å molecular sieves (0.51 g), and tetrapropylammonium perruthenate (0.050 g, 0.142 mmol, 0.10 equiv) were added sequentially. The resulting dark reaction mixture was stirred for 2.5 hours at 23° C. and then filtered through celite. The filtrate was concentrated under reduced pressure to provide a brown oil which was dissolved in $CH_2Cl_2$ (30 mL). Crude ethyl-3-[$H_2$N-L-(Tr-Gln)]-E-propenoate●HCl, prepared as described in Example 1 for the preparation of ethyl-3-[CBZ-L-LeuΨ[$COCH_2$]-D/L-Phe-L-(Tr-Gln)]-E-propenoate (1.86 mmol, 1.3 equiv), 1-hydroxybenzotriazole hydrate (0.289 g, 2.14 mmol, 1.5 equiv), 4-methylmorpholine (0.629 mL, 5.72 mmol, 4.0 equiv), and 1-(3-dimethylaminopropyl)-3-ethylcarbodiimide hydrochloride (0.411 g, 2.14 mmol, 1.5 equiv) were added sequentially, and the reaction mixture was stirred for 8 hours at 23° C. then partitioned between water (150 mL) and EtOAc (2×150 mL). The combined organic layers were dried over $Na_2SO_4$ and concentrated. Purification of the residue by flash column chromatography (40% EtOAc in hexanes) provided ethyl-3-[BOC-L-ValΨ[$COCH_2$]-L-Phe-L-(Tr-Gln)]-E-propenoate (0.497 g, 44%) as an off-white foam: $R_f$=0.40 (50% EtOAc in hexanes); IR ($cm^{-1}$) 3314, 1709, 1663; $^1H$ NMR ($CDCl_3$) δ 0.65 (d, 3H, J=6.9), 0.91 (d, 1H, J=6.9), 1.29 (t, 3H, J=7.2), 1.40 (s, 9H), 1.94–2.20 (m, 2H), 2.30–2.35 (m, 2H), 2.51 (d, 1H, J=17.1), 2.68 (dd, 1H, J=11.7, 5.8), 2.74–2.90 (m, 3H), 3.04 (dd, 1H, J=17.3, 9.8), 4.05–4.09 (m, 1H), 4.17 (q, 2H, J=7.2), 4.38–4.45 (m, 1H), 4.83 (d, 1H, J=8.1), 5.45 (d, 1H, J=15.7), 5.87 (d, 1H, J=8.1), 6.57 (dd, 1H, J=15.7, 5.0), 7.10–7.31 (m, 21H); Anal. ($C_{48}H_{57}N_3O_7$) C, H, N.

Preparation of Intermediate Ethyl-3-[EtSCO-L-ValΨ[$COCH_2$]-L-Phe-L-(Tr-Gln)]-E-Propenoate.

HCl (5 mL of a 4.0 M solution in 1,4-dioxane) was added to a solution of ethyl-3-[BOC-L-ValΨ[$COCH_2$]-L-Phe-L-(Tr-Gln)]-E-propenoate (0.225 g, 0.286 mmol, 1 equiv) in 1,4-dioxane (6 mL). The reaction mixture was stirred at 23° C. for 1.5 hours and then concentrated. The resulting oil was dissolved in $CH_2Cl_2$ (10 mL), and N,N-diisopropylethylamine (0.125 mL, 0.718 mmol, 2.5 equiv) and ethyl chlorothiolformate (0.040 mL, 0.384 mmol, 1.3 equiv) were added sequentially. The reaction mixture was stirred for 1 hour at 23° C. and then partitioned between water (100 mL) and a 1:1 mixture of EtOAc and hexanes (2×100 mL). The combined organic layers were dried over $Na_2SO_4$, concentrated, and the residue was chromatographed on silica gel (40% EtOAc in hexanes) to afford ethyl-3-[EtSCO-L-ValΨ[$COCH_2$]-L-Phe-L-(Tr-Gln)]-E-propenoate (0.148 g, 66%) as a white foam: $R_f$=0.37 (50% EtOAc in hexanes); IR ($cm^{-1}$) 3314, 1714, 1653; $^1H$ NMR ($CDCl_3$) δ 0.68 (d, 3H, J=6.9), 0.92 (d, 3H, J=6.5), 1.21–1.32 (m, 7H), 1.92–2.03 (m, 2H), 2.32–2.36 (m, 2H), 2.51 (dd, 1H, J=17.4, 2.2), 2.67 (dd, 1H, J=11.8, 5.9), 2.73–2.90 (m, 4H), 3.05 (dd, 1H, J=17.6, 9.8), 4.17 (q, 2H, J=7.2), 4.39–4.44 (m, 2H), 5.46 (dd, 1H, J=15.7, 1.7), 5.62 (d, 1H, J=8.1), 5.96 (d, 1H, J=8.4), 6.57 (dd, 1H, J=15.7, 5.1), 7.10–7.12 (m, 2H), 7.15–7.31 (m, 19H); Anal. ($C_{46}H_{53}N_3O_6S$) C, H, N.

Preparation of Product Ethyl-3-(EtSCO-L-ValΨ[$COCH_2$]-L-Phe-L-Gln)-E-Propenoate.

Ethyl-3-[EtSCO-L-ValΨ[COCH$_2$]-L-Phe-L-(Tr-Gln)]-E-propenoate (0.148 g, 0.191 mmol) was dissolved in CH$_2$Cl$_2$ (5 mL), and triisopropylsilane (0.10 mL) and trifluoroacetic acid (5 mL) were added sequentially producing a bright yellow solution. The reaction mixture was stirred for 20 minutes at 23° C., then carbon tetrachloride (6 mL) was added, and the mixture was concentrated under reduced pressure. The residue was purified by flash column chromatography (5% CH$_3$OH in CH$_2$Cl$_2$) to afford ethyl-3-(EtSCO-L-ValΨ[COCH$_2$]-L-Phe-L-Gln)-E-propenoate (0.078 g, 77%) as a white solid: mp=205° C. (dec); R$_f$=0.45 (10% CH$_3$OH in CH$_2$Cl$_2$); IR (cm$^{-1}$) 3424, 3304, 1715, 1658, 1640, 1624; $^1$H NMR (DMSO-d$_6$) δ 0.75 (d, 3H, J=6.5), 0.82 (d, 3H, J=6.9), 1.14 (t, 3H, J=7.2), 1.21 (t, 3H, J=7.2), 1.56–1.71 (m, 2H), 1.99–2.11 (m, 2H), 2.44–2.59 (m, 4H), 2.70–2.85 (m, 3H), 2.93–2.95 (m, 1H), 4.06–4.18 (m, 3H), 4.31 (s, br, 1H), 5.53 (d, 1H, J=15.6), 6.63 (dd, 1H, J=15.6, 5.1), 6.75 (s, 1H), 7.14–7.26 (m, 6H), 8.06 (d, 1H, J=8.1), 8.33 (d, 1H, J=8.1); Anal. (C$_{27}$H$_{39}$N$_3$O$_6$S) C, H, N.

EXAMPLE 7

Preparation of Compound 5: Ethyl-3-(BnSCO-L-ValΨ[COCH$_2$]-L-Phe-L-Gln)-E-Propenoate Preparation of Intermediate Ethyl-3-[BnSCO-L-ValΨ[COCH$_2$]-L-Phe-L-(Tr-Gln)]-E-Propenoate.

HCl (8 mL of a 4.0 M solution in 1,4-dioxane) was added to a solution of ethyl-3-[BOC-L-ValΨ[COCH$_2$]-L-Phe-L-(Tr-Gln)]-E-propenoate (0.272 g, 0.345 mmol, 1 equiv) in 1,4-dioxane (10 mL). The reaction mixture was stirred at 23° C. for 1.5 hours and then concentrated. The resulting oil was dissolved in CH$_2$Cl$_2$ (10 mL), and 4-methylmorpholine (0.095 mL, 0.864 mmol, 2.5 equiv) and benzyl chlorothiolformate (0.068 mL, 0.450 mmol, 1.3 equiv) were added sequentially. The reaction mixture was stirred for 1 hour at 23° C. and then partitioned between water (100 mL) and a 1:1 mixture of EtOAc and hexanes (2×100 mL). The combined organic layers were dried over Na$_2$SO$_4$, concentrated, and the residue was chromatographed on silica gel (40% EtOAc in hexanes) to afford ethyl-3-[BnSCO-L-ValΨ[COCH$_2$]-L-Phe-L-(Tr-Gln)]-E-propenoate (0.160 g, 55%) as a white foam: R$_f$=0.41 (50% EtOAc in hexanes); IR (cm$^{-1}$) 3316, 1716, 1658; $^1$H NMR (CDCl$_3$) δ 0.66 (d, 3H, J=6.9), 0.92 (d, 3H, J=6.5), 1.29 (t, 3H, J=7.2), 1.93–2.03 (m, 2H), 2.32–2.36 (m, 2H), 2.50 (dd, 1H, J=17.7, 2.5), 2.67 (dd, 1H, J=11.5, 6.2), 2.73–2.89 (m, 3H), 3.07 (dd, 1H, J=17.7, 10.0), 4.09 (s, 2H), 4.16 (q, 2H, J=7.2), 4.38–4.42 (m, 2H), 5.46 (dd, 1H, J=15.8, 1.6), 5.65 (d, 1H, J=8.4), 5.95 (d, 1H, J=8.1), 6.57 (dd, 1H, J=15.8, 5.1), 7.03 (s, 1H), 7.09–7.12 (m, 2H), 7.15–7.31 (m, 23H); Anal. (C$_{51}$H$_{55}$N$_3$O$_6$S) C, H, N.

Preparation of Product Ethyl-3-(BnSCO-L-ValΨ[COCH$_2$]-L-Phe-L-Gln)-E-Propenoate.

Ethyl-3-[BnSCO-L-ValΨ[COCH$_2$]-L-Phe-L-(Tr-Gln)]-E-propenoate (0.160 g, 0.191 mmol) was dissolved in CH$_2$Cl$_2$ (5 mL), and triisopropylsilane (0.10 mL) and trifluoroacetic acid (5 mL) were added sequentially producing a bright yellow solution. The reaction mixture was stirred for 20 minutes at 23° C., then carbon tetrachloride (5 mL) was added, and the mixture was concentrated under reduced pressure. The residue was purified by flash column chromatography (5% CH$_3$OH in CH$_2$Cl$_2$) to provide ethyl-3-(BnSCO-L-ValΨ[COCH$_2$]-L-Phe-L-Gln)-E-propenoate (0.097 g, 85%) as a white solid: mp=185–189° C.; R$_f$=0.55 (10% CH$_3$OH in CH$_2$Cl$_2$); IR (cm$^{-1}$) 3392, 3287, 1710, 1643; $^1$H NMR (DMSO-d$_6$) δ 0.74 (d, 3H, J=6.9), 0.82 (d, 3H, J=6.5), 1.21 (t, 3H, J=7.2), 1.62–1.70 (m, 2H), 1.98–2.12 (m, 3H), 2.44–2.59 (m, 2H), 2.71–2.96 (m, 3H), 4.03 (s, 2H), 4.10 (q, 2H, J=7.2), 4.19–4.23 (m, 1H), 4.32 (s, br, 1H), 5.54 (d, 1H, J=15.6), 6.64 (dd, 1H, J=15.6, 5.3), 6.75 (s, 1H), 7.14–7.28 (m, 11H), 8.06 (d, 1H, J=8.1), 8.42 (d, 1H, J=7.8); Anal. (C$_{32}$H$_{41}$N$_3$O$_6$S) C, H, N.

EXAMPLE 8

Preparation of Compound 7: Ethyl-3-(CyPentylSCO-L-ValΨ[COCH$_2$]-L-Phe-L-Gln)-E-Propenoate.

Preparation of Intermediate Ethyl-3-[CyPentylSCO-L-ValΨ[COCH$_2$]-L-Phe-L-(Tr-Gln)]-E-Propenoate HCl (6 mL of a 4.0 M solution in 1,4-dioxane) was added to a solution of ethyl-3-[BOC-L-ValΨ[COCH$_2$]-L-Phe-L-(Tr-Gln)]-E-propenoate (0.248 g, 0.315 mmol, 1 equiv) in 1,4-dioxane (6 mL). The reaction mixture was stirred at 23° C. for 1.5 hours and then concentrated. The resulting oil was dissolved in CH$_2$Cl$_2$ (15 mL), cooled to 0° C., and 4-methylmorpholine (0.086 mL, 0.782 mmol, 2.5 equiv) and cyclopentyl chlorothiolformate (0.067 mL, 0.407 mmol, 1.3 equiv) were added sequentially. The reaction mixture was stirred for 30 minutes at 0° C. and then partitioned between water (100 mL) and a 1:1 mixture of EtOAc and hexanes (2×100 mL). The combined organic layers were dried over Na$_2$SO$_4$, concentrated, and the residue was chromatographed on silica gel (40% EtOAc in hexanes) to provide ethyl-3-[CyPentylSCO-L-ValΨ[COCH$_2$]-L-Phe-L-(Tr-Gln)]-E-propenoate (0.126 g, 49%) as a white foam: R$_f$=0.42 (50% EtOAc in hexanes); IR (cm$^{-1}$) 3314, 1711, 1654; $^1$H NMR (CDCl$_3$) δ (d, 3H, J=6.9), 0.92 (d, 3H, J=6.9), 1.29 (t, 3H, J=7.2), 1.45–1.68 (m, 6H), 1.91–2.05 (m, 4H), 2.31–2.34 (m, 2H), 2.51 (d, 1H, J=17.4), 2.67 (dd, 1H, J=11.5, 6.2), 2.75–2.90 (m, 3H), 3.03 (dd, 1H, J=17.3, 9.8), 3.60–3.64 (m, 1H), 4.17 (q, 2H, J=7.2), 4.36–4.44 (m, 2H), 5.46 (dd, 1H, J=15.8, 1.7), 5.57 (d, 1H, J=8.1), 5.95 (d, 1H, J=8.4), 6.58 (dd, 1H, J=15.8, 5.0), 7.10–7.12 (m, 2H), 7.19–7.31 (m, 19H); Anal. (C$_{49}$N$_{57}$N$_3$O$_6$S) C, H, N.

Preparation of Product Ethyl-3-(CyPentylSCO-L-ValΨ[COCH$_2$]-L-Phe-L-Gln)-E-Propenoate Ethyl-3-[CyPentylSCO-L-ValΨ[COCH$_2$]-L-Phe-L-(Tr-Gln)]-E-propenoate (0.126 g, 0.154 mmol) was dissolved in CH$_2$Cl$_2$ (6 mL), and triisopropylsilane (0.10 mL) and trifluoroacetic acid (6 mL) were added sequentially producing a bright yellow solution. The reaction mixture was stirred for 20 minutes at 23° C., then carbon tetrachloride (6 mL) was added, and the mixture was concentrated under reduced pressure. The residue was purified by flash column chromatography (5% CH$_3$OH in CH$_2$Cl$_2$) to afford ethyl-3-(CyPentylSCO-L-ValΨ[COCH$_2$]-L-Phe-L-Gln)-E-propenoate (0.046 g, 52%) as a white solid: mp=200–204° C.; R$_f$=0.38 (10% CH$_3$OH in CH$_2$Cl$_2$); IR (cm$^{-1}$) 3431, 3261, 1717, 1642; $^1$H NMR (DMSO-d$_6$) δ 0.75 (d, 3H, J=6.5), 0.82 (d, 3H, J=6.5), 1.22 (t, 3H, J=7.2), 1.40–1.74 (m, 7H), 1.95–2.10 (m, 6H), 2.43–2.59 (m, 2H), 2.71–2.84 (m, 2H), 2.93–2.95 (m, 1H), 3.47–3.56 (m, 1H), 4.06–4.16 (m, 3H), 4.32 (s, br, 1H), 5.54 (d, 1H, J=15.9), 6.64 (dd, 1H, J=15.9, 5.3), 6.75 (s, 1H), 7.15–7.27 (m, 6H), 8.06 (d, 1H, J=7.8), 8.27 (d, 1H, J=8.1); Anal. (C$_{30}$H$_{43}$N$_3$O$_6$S) C, H, N.

EXAMPLE 9

Preparation of Compound 3: (2,3-Dihydroindole)-3-(BnSCO-L-LeuΨ[COCH$_2$]-L-Phe-L-Gln)-E-Propenamide Preparation of Intermediate [2-(2,3-Dihydro-indol-1-yl)-2-oxo-ethyl]-phosphonic Acid Diethyl Ester.

Oxalyl chloride (5.96 mL, 68.3 mmol, 1.05 equiv) was added to a solution of diethylphosphonoacetic acid (12.8 g, 65.0 mmol, 1 equiv) and N,N-dimethylformamide (0.03 mL, 0.39 mmol, 0.006 equiv) in benzene (150 mL) at 23° C. The reaction mixture was stirred at 23° C. for 1 hour and then concentrated under reduced pressure. The resulting oil was dissolved in THF (30 mL) and added via cannula to a solution of indoline (7.38 g, 61.9 mmol, 0.95 equiv) and triethylamine (10.9 mL, 78.0 mmol, 1.2 equiv) in THF (200 mL) at 0° C. The reaction mixture was stirred at 0° C. for 15 minutes, and it then was partitioned between 0.5 M HCl (150 mL) and EtOAc (2×150 mL). The combined organic layers were dried over $Na_2SO_4$ and concentrated to afford a tan solid. Recrystallization from $Et_2O$ provided [2-(2,3-dihydro-indol-1-yl)-2-oxo-ethyl]-phosphonic acid diethyl ester (12.2 g, 63%) as a light brown solid: mp: 97–99° C.; $R_f$=0.06 (50% EtOAc in hexanes); IR ($cm^{-1}$) 3460, 1657, 1597, 1482; $^1H$ NMR ($CDCl_3$) δ 1.35 (t, 6H, J=7.2), 3.14 (d, 2H, J=22.4), 3.22 (d, 2H, J=8.4), 4.15–4.30 (m, 6H), 7.04 (t, 1H, J=7.0), 7.17–7.28 (m, 2H), 8.21 (d, 1H, J=9.0); Anal. ($C_{14}H_{20}NO_4P$) C, H, N.

Preparation of Intermediate (2,3-Dihydroindole)-3-[BOC-L-(Tr-Gln)]-E-Propenamide.

Sodium bis(trimethylsilyl)amide (11.9 mL of a 1.0 M solution in THF, 11.9 mmol, 1.0 equiv) was added to a solution of [2-(2,3-dihydro-indol-1-yl)-2-oxo-ethyl]-phosphonic acid diethyl ester (3.54 g, 11.9 mmol, 1.0 equiv) in THF (150 mL) at −78° C., and the resulting solution was stirred for 20 minutes at that temperature. Crude [BOC-L-(Tr-Gln)]-H (5.63 g, 11.9 mmol, 1 equiv), prepared as described in Example 1, in THF (40 mL) was added via cannula, and the reaction mixture was stirred for 1 hour at −78° C., warmed to 0° C. for 10 minutes, and partitioned between 0.5 M HCl (150 mL) and EtOAc (2×150 mL). The organic layers were dried over $Na_2SO_4$ and concentrated. Purification of the residue by flash column chromatography (50% EtOAc in hexanes) provided (2,3-dihydroindole)-3-[BOC-L-(Tr-Gln)]-E-propenamide (6.35 g, 87%) as an off-white foam: $R_f$=0.28 (50% EtOAc in hexanes); IR ($cm^{-1}$) 3401, 3307, 1690, 1665; $^1H$ NMR ($CDCl_3$) δ 1.44 (s, 9H), 1.76–2.05 (m, 2H), 2.37–4.06 (m, 2H), 2.37–4.06 (m, 2H), 3.11–3.22 (m, 2H), 4.02–4.16 (m, 2H), 4.27–4.40 (m, 1H), 4.91–4.97 (m, 1H), 6.29 (d, 1H, J=14.9), 6.77–6.96 (m, 2H), 6.98–7.05 (m, 1H), 7.14–7.37 (m, 17H), 8.25 (d, 1H, J=7.5); Anal. ($C_{39}H_{41}N_3O_4$) C, H, N.

Preparation of Intermediate (2,3-Dihydroindole)-3-[BOC-L-LeuΨ[$COCH_2$]-L-Phe-L-(Tr-Gln)]-E-Propenamide.

Lithium hydroxide (8.0 mL of a 1 M aqueous solution, 8.0 mmol, 5.0 equiv) was added to a solution of [1S-(4R-benzyl-5-oxo-tetrahydrofuran-2S-yl)-3-methyl-butyl]-carbamic acid tert-butyl ester (0.576 g, 1.59 mmol, 1 equiv), prepared as described in Example 1, in DME (8 mL) at 23° C. The resulting suspension was stirred at 23° C. for 45 minutes, and it then was partitioned between 0.5 M HCl (100 mL) and EtOAc (2×100 mL). The combined organic layers were dried over $Na_2SO_4$, concentrated, and the residue dissolved in $CH_2Cl_2$ (30 mL). 4-Methylmorpholine N-oxide (0.373 g, 3.18 mmol, 2.0 equiv), powdered 4 Å molecular sieves (0.60 g), and tetrapropylammonium perruthenate (0.056 g, 0.159 mmol, 0.10 equiv) were added sequentially. The resulting dark reaction mixture was stirred for 1 hour at 23° C. and then filtered through celite. The filtrate was concentrated under reduced pressure to provide a brown oil which was dissolved in $CH_2Cl_2$ (20 mL). Crude (2,3-dihydroindole)-3-($H_2N$-L-Tr-Gln)-E-propenamide●HCl (prepared from (2,3-dihydroindole)-3-[BOC-L-(Tr-Gln)]-E-propenamide in a manner analogous to the method described in Example 1 for the preparation of ethyl-3-[$H_2N$-L-(Tr-Gln)]-E-propenoate●HCl (2.39 mmol, 1.5 equiv), 1-hydroxybenzotriazole hydrate (0.322 g, 2.38 mmol, 1.5 equiv), 4-methylmorpholine (0.699 mL, 6.36 mmol, 4.0 equiv), and 1-(3-dimethylaminopropyl)-3-ethylcarbodiimide hydrochloride (0.322 g, 2.38 mmol, 1.5 equiv) were added sequentially, and the reaction mixture was stirred for 16 hours at 23° C. and then partitioned between water (100 mL) and EtOAc (2×100 mL). The combined organic layers were dried over $Na_2SO_4$ and concentrated. Purification of the residue by flash column chromatography (40% hexanes in EtOAc) provided (2,3-dihydroindole)-3-[BOC-L-Leu-Ψ[$COCH_2$]-L-(Tr-Gln)]-E-propenamide (0.568 g, 40%) as tan foam; $R_f$=0.64 (10% $CH_3OH$ in $CH_2Cl_2$); IR ($cm^{-1}$) 3304, 1700, 1665; $^1H$ NMR ($CDCl_3$) δ0.86 (d, 6H, J=6.5), 0.97–1.12 (m, 1H), 1.39 (s, 9H), 1.45–1.64 (m, 2H), 2.39–2.43 (m, 2H), 2.51 (d, 1H, J=15.6), 2.67 (dd, 1H, J=12.3, 7.0), 2.79–2.96 (m, 3H), 3.16 (s, br, 2H), 4.01–4.20 (m, 5H), 4.52 (s, br, 1H), 4.63 (d, 1H, J=7.8), 6.09 (d, 1H, J=14.7), 6.17 (d, 1H, J=8.1), 6.65 (dd, 1H, J=14.7, 5.8), 6.99–7.04 (m, 1H), 7.11–7.39 (m, 23H), 8.26 (d, 1H, J=7.5).

Preparation of Product (2,3-Dihydroindole)-3-[BnSCO-L-LeuΨ[$COCH_2$]-L-Phe-L-(Tr-Gln)]-E-Propenamide HCl (6 mL of a 4.0 M solution in 1,4-dioxane) was added to a solution of (2,3-dihydroindole)-3-[BOC-L-LeuΨ[$COCH_2$]-L-Phe-L-(Tr-Gln)]-E-propenamide (0.204 g, 0.233 mmol, 1 equiv) in 1,4-dioxane (8mL). The reaction mixture was stirred at 23° C. for 2.5 hours and then concentrated. The resulting oil was dissolved in $CH_2Cl_2$ (8 mL), and N,N-diisopropylethylamine (0.081 mL, 0.465 mmol, 2.0 equiv) and benzyl chlorothiolformate (0.042 mL, 0.279 mmol, 1.2 equiv) were added sequentially. The reaction mixture was stirred for 2 hours at 23° C. and then partitioned between water (100 mL) and a 1:1 mixture of EtOAc and hexanes (2×100 mL). The combined organic layers were dried over $Na_2SO_4$ and concentrated to provide crude (2,3-dihydroindole)-3-[BnSCO-L-LeuΨ[$COCH_2$]-L-Phe-L-(Tr-Gln)]-E-propenamide as an off-white foam. This material was dissolved in $CH_2Cl_2$ (5 mL), and triisopropylsilane (0.075 mL), and trifluoroacetic acid (5 mL) were added sequentially producing a bright yellow solution. The reaction mixture was stirred for 30 minutes at 23° C., then carbon tetrachloride (4 mL) was added, and the mixture was concentrated under reduced pressure. The residue was purified by flash column chromatography (5% $CH_3OH$ in $CH_2Cl_2$) to afford (2,3-dihydroindole)-3-(BnSCO-L-LeuΨ[$COCH_2$]-L-Phe-L-Gln)-E-propenamide (0.016 g, 10%) as a white foam: $R_f$=0.51 (10% $CH_3OH$ in $CH_2Cl_2$); $^1H$ NMR ($CDCl_3$)δ0.92 (d, 6H, J=6.2), 1.11–1.15 (m, 1H), 1.33–1.36 (m, 1H), 1.49–2.17 (m, 4H), 2.25 (s, br, 2H), 2.58 (d, 1H, J=17.1), 2.70–2.72 (m, 1H), 2.94–3.17 (m, 4H), 4.01–4.04 (m, 2H), 4.11 (s, 2H), 4.52–4.58 (m, 2H), 5.47 (s, br, 1H), 6.13 (d, 1H, J=13.4), 6.29 (s, br, 1H), 6.41 (s, br, 1H), 6.66 (s, br, 1H), 7.00–7.05 (m, 1H), 7.17–7.29 (m, 13H), 8.25 (d, 1H, J=7.2).

EXAMPLE 10

Preparation of Compound 10: Ethyl-3-(EtSCO-L-ValΨ[$COCH_2$]-L-(p-$CH_3$)Phe-L-Gln)-E-Propenoate Preparation of Intermediate trans-6-Methyl-2S-(4-methyl-benzyl)-hept-4-enoic Acid (2R-Hydroxy-1R-methyl-2-phenyl-ethyl)-methyl Amide n-Butyllithium (33.7 mL of a 1.6 M solution in hexanes, 53.9 mmol, 2.15 equiv) was added to a suspension of anhydrous lithium chloride (7.47 g, 176 mmol, 7.0 equiv) and diisopropylamine (8.09 mL, 57.7 mmol, 2.3 equiv) in THF (260 mL) at −78° C. The reaction mixture was stirred for 30 minutes at −78° C., maintained at 0° C. for 5 minutes, and subsequently cooled again to −78° C. trans-6-Methyl-hept-4-enoic acid (2R-hydroxy-1R-methyl-2-phenyl-ethyl)-methyl amide (7.26 g, 25.1 mmol, 1 equiv) in THF (50 mL) was added via cannula, and the resulting solution was stirred at −78° C. for 1.75 hours, maintained at 0° C. for 20 minutes, stirred at 23° C. for 5 minutes, and then cooled again to 0° C. A solution of 4-methylbenzyl bromide (6.96 g, 37.6 mmol, 1.5 equiv) in THF (15 mL ) was added, and the reaction mixture was stirred at 0° C. for 30 minutes and then partitioned between half-saturated NH$_4$Cl (230 mL) and a 1:1 mixture of EtOAc and hxanes (200 mL, 2×150 mL). The combined organic layers were dried over Na$_2$SO$_4$ and concentrated. Purification of the residue by flash column chromatography (gradient elution 20→40% EtOAc in hexanes) provided trans-6-methyl-2S-(4-methyl-benzyl)-hept-4-enoic acid (2R-hydroxy-1R-methyl-2-phenyl-ethyl)-methyl amide (9.33 g, 95%) as a viscous oil; R$_f$=0.44 (40% EtOAc in hexanes); IR (cm$^{-1}$) 3378, 1619; $^1$H NMR (CDCl$_3$, mixture of rotamers) δ0.84–0.97 (m), 2.12–2.27 (m), 2.29 (s), 2.35–2.46 (m), 2.58 (s), 2.66–2.84 (m), 2.86–3.05 (m), 3.91–4.13 (m), 4.30–4.44 (m), 4.45–4.53 (m), 5.17–5.54 (m), 7.04 (s), 7.12–7.33 (m); Anal. (C$_{26}$H$_{35}$NO$_2$) C,H,N.

Preparation of Intermediate 5S-(1R-Bromo-2-methyl-propyl)-3R-(4-methyl-benzyl)-dihydrofuran-2-one N-Bromosuccinimide (4.37 g, 24.6 mmol, 1.05 equiv) was added in small portions over 10 minutes to a solution of trans-6-methyl-2S-(4-methyl-benzyl)-hept-4-enoic acid (2R-hydroxy-1R-methyl-2-phenyl-ethyl)-methyl amide (9.21 g, 23.4 mmol, 1 equiv) and glacial acetic acid (6.70 mL, 117 mmol, 5.0 equiv) in a 4:1 mixture of THF and H$_2$O (250 mL) at 0° C. The resulting yellow solution was stirred for 15 minutes at 0° C., then warmed to 23° C., and subsequently refluxed for 45 minutes. After cooling to 23° C., the reaction mixture was partitioned between half-saturated NaHCO$_3$ (200 mL) and a 1:1 mixture of EtOAc and hexanes (2×200 mL, 100 mL). The combined organic layers were dried over Na$_2$SO$_4$ and concentrated. Flash chromatographic purification of the residue (gradient elution 4→6% EtOAc in hexanes) gave 5S-(1R-bromo-2-methyl-propyl)-3R-(4-methyl-benzyl)-dihydrofuran-2-one (6.45 g, 85%) as a white solid (containing approximately 5–10% unidentified impurities by $^1$H NMR): mp=94–100° C.; R$_f$=0.64 (25% EtOAc in hexanes); IR (cm$^{-1}$) 1772; $^1$H NMR (CDCl$_3$, major isomer) δ0.93 (d, 3H, J=6.5) 0.99 (d, 3H, J=6.5), 2.05–2.18 (m, 1H), 2.21–2.28 (m, 2H), 2.33 (s, 3H), 2.79 (dd, 1H, J=13.5, 9.0), 2.92–3.03 (m, 1H), 3.12 (dd, 1H, J=13.5, 4.5), 3.89 (dd, 1H, J=9.0, 3.4), 4.32–4.41 (m, 1H), 7.06–7.16 (m, 4H); Anal. (C$_{16}$H$_{21}$BrO$_2$) C,H.

Preparation of Intermediate 5S-(1S-Azido-2-methyl-propyl)-3R-(4-methyl-benzyl)-dihydrofuran-2-one A suspension of sodium azide (2.55 g, 39.2 mmol, 2.0 equiv) and 5S-(1R-bromo-2-methyl-propyl)-3R-(4-methyl-benzyl)-dihydrofuran-2-one (6.37 g, 19.6 mmol, 1 equiv) in N,N-dimethylformamide (63 mL) was heated at 50° C. for 48 hours. The reaction mixture was cooled to 23° C. and partitioned between water (370 mL) and a 1:1 mixture of EtOAc and hexanes (2×370 mL, 200 mL). The combined organic layers were dried over Na$_2$SO$_4$, concentrated, and the residue purified by flash column chromatography (gradient elution 8→12% EtOAc in hexanes) to give 5S-(1S-azido-2-methyl-propyl)-3R-(4-methyl-benzyl)-dihydrofuran-2-one (3.33 g, 59%) as a colorless oil (containing approximately 5–10% unidentified impurities by $^1$H NMR): R$_f$=0.52 (25% EtOAc in hexanes); IR (cm$^{-1}$) 2097, 1772; $^1$H NMR (CDCl$_3$, major isomer) δ0.97 (d, 3H, J=6.5) 1.01 (d, 3H, J=6.8), 1.94–2.06 (m, 1H), 2.07–2.13 (m, 2H), 2.33 (s, 3H), 2.79 (dd, 1H, J=13.2, 8.2), 2.92 (dd, 1H, J=6.8, 4.4), 3.02–3.17 (m, 2H), 4.32–4.40 (m, 1H), 7.07–7.15 (m, 4H); Anal. (C$_{16}$H$_{21}$N$_3$O$_2$) C,H,N.

Preparation of Intermediate {2-Methyl-1S-[4R-(4-methyl-benzyl)-5-oxo-tetrahydrofuran-2S-yl]-propyl}-carbamic Acid tert-Butyl Ester A suspension of 5S-(1S-azido-2-methyl-propyl)-3R-(4-methyl-benzyl)-dihydrofuran-2-one (3.24 g, 11.3 mmol, 1 equiv) and Pd/C (10%, 0.25 g) in CH$_3$OH (190 mL) was stirred under a hydrogen atmosphere (balloon) for 1 hour. The reaction mixture was vacuum filtered through Whatman #3 paper, concentrated, and the residue dissolved in 1,4-dioxane (100 mL), N,N-diisopropylethylamine (3.93 mL, 22.6 mmol, 2.0 equiv) and di-tert-butyl dicarbonate (3.69 g, 16.9 mmol, 1.5 equiv) were added sequentially, and the resulting solution was stirred at 23° C. for 16 hours. The raction mixture was then partitioned between water (200 mL) and a 1:1 mixture of EtOAc and hexanes (2×300 mL, 200 mL). The combined organic layers were dried over Na$_2$SO$_4$ and concentrated. Purification of the residue by flash column chromatography (gradient elution, 11→17% EtOAc in hexanes) provided {2-methyl-1S-[4R-(4-methyl-benzyl)-5-oxo-tetrahydrofuran-2S-yl]-propyl}-carbamic acid tert-butyl ester (1.71 g, 42%) as a viscous oil: R$_f$=0.54 (25% EtOAc in hexanes); IR (cm$^{-1}$) 3331, 1766, 1696; $^1$H NMR (CDCl$_3$) δ0.92 (d, 3H, J=6.5), 0.93 (d, 3H, J=6.5), 1.41 (s, 9H), 1.72–1.83 (m, 1H), 1.96–2.06 (m, 1H), 2.11–2.22 (m, 1H), 2.31 (s, 3H), 2.77 (dd, 1H, J=13/5 8/7), 2.88–2.99 (m, 1H), 3.08 (dd, 1H, J=13.5, 4.5), 3.30–3.38 (m, 1H), 4.38–4.44 (m, 1H), 4.49 (d, 1H, J=10.0), 7.04–7.13 (m, 4H); Anal. (C$_{21}$H$_{31}$NO$_4$) C,H,N.

Preparation of Intermediate Ethyl -3-[BOC-L-ValΨ[COCH$_2$]-L-(p-CH$_3$)Phe-L-(Tr-Gln)]-E-Propenoate Lithium hydroxide (7.9 mL of a 1 M aqueous solution, 7.9 mmol, 5.0 equiv) was added to a solution of {2-methyl-1S-[4R-(4-methyl-benzyl)-5-oxo-tetrahydrofuran-2S-yl]-propyl}-carbamic acid tert-butyl ester (0.570 g, 1.58 mmol, 1 equiv) in DME (15 mL) at 23° C. The resulting suspension was stirred at 23° C. for 30 minutes and then partitioned between 10% KHSO$_4$ (35 mL) and CH$_2$Cl$_2$ (100 mL, 2×70 mL). The combined organic layers were dried over Na$_2$SO$_4$, concentrated, and the residue dissolved in CH$_2$Cl$_2$ (25 mL). Powdered 4 Å molecular sieves (0.56 g), 4-methylmorpholine N-oxide (0.369 g, 3.15 mmol, 2.0 equiv), and tetrapropylammonium perruthenate (0.055 g, 0.16 mmol, 0.10 equiv) were added sequentially. The resulting dark reaction mixture was stirred for 1.33 hours at 23° C., and the mixture then was vacuum filtered through Whatman #3 paper and then through Whatman #5 paper. The filtrate was concentrated under reduced pressure to provide a dark residue which was dissolved in CH$_2$Cl$_2$ (25 mL). Crude ethyl-3-[N$_2$N-L-(Tr-Gly)]-E-propenoate.HCl (see preparation of ethyl-3-[CBZ-L-LeuΨ[COCH$_2$]-D/L-Phe-L-(Tr-Gln)]-E-propenoate, 1.90 mmol, 1.2 equiv), 4-methylmorpholine (0.693 mL, 6.30 mmol, 4.0 equiv), 1-hydroxybenzotriazole hydrate (0.320 g, 2.37 mmol, 1.5 equiv), and 1-(3-dimethylaminopropyl)-3-ethylcarbodiimide hydrochloride (0.453 g, 2.36 mmol, 1.5 equiv) were added sequentially, and the reaction mixture was stirred for 20 hours at 23° C. and then partitioned between water (70 mL) and EtOAc (2×100 mL, 50 mL). The combined organic layers were dried over Na$_2$SO$_4$ and were concentrated. Purification of the residue by flash column chromatography (38% EtOAc in hexanes) provided ethyl-3-[BOC-L-ValΨ[COCH$_2$]-L-(p-CH$_3$)Phe-L-(Tr-Gln)]-E-propenoate (0.677 g, 54%) as an off-white foam: R$_f$=0.44 (50% EtOAc in hexanes); IR (cm$^{-1}$) 3307, 1708, 1666; $^1$H NMR (CDCl$_3$) δ0.64 (d, 3H, J=6.8) 0.91 (d, 3H, J=6.5), 1.28 (t, 3H, J=7.2), 1.40 (s, 9H), 1.55–1.67 (m, 1H), 1.92–2.04 (m, 2H), 2.31 (s, 3H), 2.32–2.40 (m, 2H), 2.45–2.54 (m, 1H), 2.63 (dd, 1H, J=11.5, 5.9), 2.68–2.87 (m, 2H), 3.03 (dd, 1H, J=17.4, 10.0), 4.04–4.51 (m, 1H), 4.17 (q, 2H, J=7.2), 4.41–4.52 (m, 1H), 4.83 (d, 1H, J=8.4), 5.49 (d, 1H, J=15.7), 5.86 (d, 1H, J=8.4), 6.60 (dd, 1H, J=15.7, 5.0), 7.00 (d, 2H, J=8.0), 7.09 (d, 2H, J=8.0); Anal. (C$_{49}$H$_{59}$N$_3$O$_7$) C,H,N.

Preparation of Intermediate Ethyl-3[EtSCO-L-ValΨ[COCH$_2$]-L-(p-CH$_3$) Phe-L-(Tr-Gln)]-E-Propenoate HCl (3 mL of a 4.0 M solution in 1,4-dioxane) was added to a solution of ethyl-3-[BOC-L-ValΨ[COCH$_2$]-L-(p-CH$_3$)Phe-L-(Tr-Gln)]-E-propenoate (0.315 g, 0.393 mmol, 1 equiv) in 1,4-dioxane (3 mL). The reaction mixture was stirred at 23° C. for 2 hours and then concentrated. The resulting oil was dissolved in CH$_2$Cl$_2$ (5 mL), and N,N-diisopropylethylamine (0.205 mL, 1.18 mmol, 3.0 equiv) and ethyl chlorothiolformate (0.061 mL, 0.59 mmol, 1.5 equiv) were added sequentially. The reaction mixture was stirred for 2 hours at 23° C. and then partitioned between brine (30 mL) and CH$_2$Cl$_2$ (3×30 mL). The combined organic layers were dried over Na$_2$SO$_4$, concentrated, and the residue was chromatographed on silica gel (40% EtOAc in hexanes) to afford ethyl-3-[EtSCO-L-ValΨ[COCH$_2$]-L-(p-CH$_3$)Phe-L-(Tr-Gln)]-E-propenoate (0.220 g, 71%) as a white foam: R$_f$=0.29 (40% EtOAc in hexanes); IR (cm$^{-1}$) 3307, 1713, 1655; $^1$H NMR (CDCl$_3$) δ0.67 (d, 3H, J=6.8), 0.92 (d, 3H, J=6.8), 1.25 (t, 3H, J=7.4), 1.28 (t, 3H, J=7.4), 1.55–1.67 (m, 1H), 1.91–2.03 (m, 3H), 2.31 (s, 3H), 2.32–2.37 (m, 2H), 2.49 (dd, 1H, J=17.7, 2.2) 2.62 (dd, 1H, J=11.7, 6.1), 2.69–2.83 (m, 2H), 2.84 (q, 2H, J=7.4), 3.04 (dd, 1H, J=17.7, 10.0), 4.17 (q, 2H, J=7.4), 4.35–4.51 (m, 2H), 5.50 (dd, 1H, J=15.6, 1.6) 5.62 (d, 1H, J=8.1), 5.95 (d, 1H, J=8.1), 6.60 (dd, 1H, J=15.6, 5.1), 6.99 (d, 2H, J=8.1), 7.09 (d, 2H, J=8.1), 7.18–7.31 (m, 16H); Anal. (C$_{47}$H$_{55}$N$_3$O$_6$S) C,H,N.

Preparation of Product Ethyl-3-(EtSCO-L-ValΨ[COCH$_2$]-L-(p-CH$_3$)Phe-L-Gln)-E-Propenoate Ethyl-3-[EtSCO-L-VAlΨ[COCH$_2$]-L-(p-CH$_3$)Phe-L-(Tr-Gln)]-E-propenoate (0.169 g, 0.214 mmol) was dissolved in CH$_2$Cl$_2$ (6 mL), and triisopropylsilane (0.13 mL) and trifluoroacetic acid (3 mL) were added sequentially producing a bright yellow solution. The reaction mixture was stirred for 30 minutes at 23° C. and then concentrated under reduced pressure. The residue was purified by flash column chromatography (6% CH$_3$OH in CH$_2$Cl$_2$) to afford ethyl-3-(EtSCO-L-ValΨ[COCH$_2$]-L-(p-CH$_3$)Phe-L-Gln)-E-propenoate (0.072 g, 63%) as a white solid: mp=220° C. (dec); R$_f$=0.11 (5% CH$_3$OH in CH$_2$Cl$_2$); IR (cm$^{-1}$) 3425, 3307, 1713, 1655; $^1$H NMR (DMSO-d$_6$) δ0.74 (d, 3H, J=6.8), 0.82 (d, 3H, J=6.8), 1.14 (t, 3H, J=7.3), 1.20 (t, 3H, J=7.2), 1.54–1.76 (m, 2H), 1.98–2.13 (m, 3H), 2.23 (s, 3H), 2.40–2.54 (m, 2H), 2.65–2.84 (m, 2H), 2.73 (q, 2H, J=7.3), 2.86–2.96 (m, 1H), 4.04–4.19 (m, 3H), 4.26–4.37 (m, 1H), 5.55 (dd, 1H, J=15.7, 1.6), 6.65 (dd, 1H, J=15.7, 5.3), 6.73 (s, 1H), 7.03 (s, 4H), 7.14 (s, 1H), 8.03 (d, 1H, J=8.1) 8.31 (d, 1H, J=7.8); Anal. (C$_{28}$H$_{41}$N$_3$O$_6$S) C,H,N.

EXAMPLE 11

Preparation of Compound 11: Ethyl-3-(CyPentylSCO-L-ValΨ[COCH$_2$]-L-(p-CH$_3$)Phe-L-(Gln)-E-Propeonate Preparation of Intermediate Ethyl-3-[CyPentylSCO-L-ValY[COCH$_2$]-L-(p-CH$_3$)Phe-L-(Tr-Gln)]-E-Propenoate HCl (3 mL of a 4.0 M solution in 1,4-dioxane) was added to a solution of ethyl-3-[BOC-L-ValΨ[COCH$_2$]-L-(p-CH$_3$)Phe-L-(Tr-Gln)]-E-propenoate (0.304 g, 0.379 mmol, 1 equiv) in 1,4-dioxane (3 mL). The reaction mixture was stirred at 23° C. for 2.3 hours and then concentrated. The resulting oil was dissolved in CH$_2$Cl$_2$ (5 mL), and N,N-diisopropylethylamine (0.198 mL, 1.14 mmol, 3.0 equiv) and cyclopentyl chlorothiolformate (0.094 mL, 0.571 mmol, 1.5 equiv) were added sequentially. The reaction mixture was stirred for 3 hours at 23° C. and then partitioned between brine (30 mL) and CH$_2$Cl$_2$ (3×30 mL). The combined organic layers were dried over Na$_2$SO$_4$, concentrated, and the residue was chromatographed on silica gel (40% EtOAc in hexanes) to provide ethyl-3-[CyPentylSCO-L-ValΨ[COCH$_2$]-L-(p-CH$_3$)Phe-L-(Tr-Gln)]-E-propenoate (0.198 g, 63%) as a white foam: R$_f$=0.29 (40% EtOAc in hexanes); IR (cm$^{-1}$) 3307, 1713, 1655, $^1$H NMR (CDCl$_3$) δ0.67 (d, 3H, J=6.8) 0.92 (d, 3H, J=6.8), 1.28 (t, 3H, J=7.2), 1.45–1.74 (m, 7H), 1.90–2.11 (m, 4H), 2.31 (s, 3H), 2.32–2.38 (m, 2H), 2.50 (dd, 1H, J=17.7, 2.5), 2.62 (dd, 1H, J=11.7, 5.8), 2.70–2.87 (m, 2H), 3.02 (dd, 1H, J=17.7, 9.8), 3.57–3.67 (m, 1H), 4.17 (q, 2H, J=7.2), 4.22–4.31 (m, 2H), 5.50 (dd, 1H, J=15.8, 1.6), 5.58 (d, 1H, J=8.4), 5.93 (d, 1H, J=8.1), 6.60 (dd, 1H, J=15.8, 5.1), 6.99 (d, 2H, J=7.9), 7.09 (d, 2H, J=7.9), 7.18–7.31 (m, 16H); Anal. (C$_{50}$H$_{59}$N$_3$O$_6$S) C,H,N.

Preparation of Product Ethyl-3-(CyPentylSCO-L-ValY[COCH$_2$]-L-(p-CH$_3$)Phe-L-Gln)-E-Propenoate Ethyl-3-[CyPentylSCO-L-ValΨ[COCH$_2$]-L-(p-CH$_3$)Phe-L-(tr-gln)]-E-propenoate (0.56 g, 0.188 mmol) was dissolved in CH$_2$Cl$_2$ (6 mL), and triisopropylsilane (0.12 mL) and trifluoroacetic acid (3 mL) were added sequentially producing a bright yellow solution. The reaction mixture was stirred for 30 minutes at 23° C. and then concentrated under reduced pressure. Et$_2$O (5 mL) was added to the residue producing a white precipitate. The precipitate was filtered, washed with Et$_2$O (3×3 mL), and dried to provide ethyl-3-(CyPentylSCO-L-ValΨ[COCH$_2$]-L-(p-CH$_3$)Phe-L-Gln)-E-propenoate (0.096 g, 87%) as a white solid: mp=208–210° C. (dec); R$_f$=0.43 (10% CH$_3$OH in CH$_2$Cl$_2$); IR (cm$^{-1}$) 3425, 3295, 1713, 1649; $^1$H NMR (DMSO-d$_6$) δ0.74 (d, 3H, J=6.5), 0.81 (d, 3H, J=6.5), 1.20 (t, 3H, J=7.2), 1.37–1.76 (m, 8H), 1.91–2.12 (m, 5H), 2.23 (s, 3H), 2.39–2.54 (m, 2H), 2.65–2.83 (m, 2H), 2.86–2.96 (m, 1H), 3.46–3.57 (m, 1H), 4.04–4.17 (m, 3H), 4.26–4.37 (m, 1H), 5.55 (dd, 1H, J=15.7, 1.4), 6.65 (dd, 1H, J=15.7, 5.4), 6.74 (s, 1H), 7.03 (s, 4H), 7.15 (s, 1H), 8.03 (d, 1H, J=8.4), 8.25 (d, 1H, J=8.1); Anal. (C$_{31}$H$_{45}$N$_3$O$_6$S) C, H, N.

EXAMPLE 12

Preparation of Compound 12: Ethyl-3-(CyPentylSCO-L-PheΨ[COCH$_2$]-L-(p-CH$_3$)Phe-L-Gln)-E-Propenoate Preparation of Intermediate (1R/S-Oxiranyl-2S-phenylethyl)-carbamic Acid tert-Butyl Ester (1:1 Mixture of Isomers)

DMSO (30 mL) was added to sodium hydride (0.900 g of a 60% dispersion in mineral oil, 22.5 mmol, 2.1 equiv), and the resulting suspension was heated to 70° C. for 20 min. The clear solution thus obtained was cooled to 23° C., and THF (40 mL) was added. The reaction mixture was then cooled to 0° C., and a solution of trimethylsulfonium iodide (4.59 g, 22.5 mmol, 2.1 equiv) in DMSO (30 mL) was added via cannula over 2 min. After stirring for 1 min at 0° C., a solution of BOC-L-Phe-H (prepared according to Luly, J. R.; Dellaria, J. F.; Plattner, J. J.; Soderquist, J. L.; Yi, N. *J. Org. Chem.* 1987, 52, 1487) (2.5 g, 10.7 mmol, 1 equiv) in THF (20 mL) was added via cannula over 5 min. The reaction mixture was stirred at 0° C. for 2 h and then partitioned between 0.5 M HCl (150 mL) and a 1:1 mixture of EtOAc and hexanes (2×150 mL). The organic layers were dried over Na$_2$SO$_4$ and concentrated. PUrificaton of the residue by flash column chromatography (gradient elution, 15→20% EtOAc in hexanes) afforded (1R/S-oxiranyl-2S-phenylethyl)-carbamic acid tert-butyl ester (1:1 mixture of isomers, 1.71 g, 60%) as a colorless oil: R$_f$=0.29 (isomer #1), 0.35 (isomer #2) (20% EtOAc in hexanes); IR (cm$^{-1}$) 3347, 2977, 1700; $^1$H NMR (CDCl$_3$) δ1.38 (s), 1.43 (s), 2.57–3.03 (m), 3.76 (s, br), 3.98 (s, br), 4.11 (s, br), 4.48 (s, br), 4.88 (s, br), 7.18–7.38 (m); Anal. (C$_{15}$H$_{31}$NO$_3$)C,H,N.

Preparation of Intermediate 3-Tolyl-propionic Acid cis-1S-Amino-2R-indanol-acetonide Amide Oxalyl chloride (3.07 mL, 35.2 mmol, 1.05 equiv) was added to a solution of 3-p-tolyl-propionic acid (5.50 g, 33.5 mmol, 1 equiv) and N,N-dimethylformamide (0.03 mL, 0.39 mmol, 0.012 equiv) in benzene (150 mL) at 23° C. The reaction mixture was stirred at 23° C. for 3 h and then concentrated. The resulting oil was dissolved in THF (30 mL) and added to a 0° C. solution of (1S,2R)-cis-1-amino-2-indanol (5.0 g, 33.5 mmol, 1.0 equiv) and Et$_3$N (5.14mL, 36.9 mmol, 1.1 equiv) in THF (250 mL). After stirring for 30 min at 0° C., the reaction mixture was partitioned between half-saturated NH$_4$Cl (150 mL) and EtOAc (2×150 mL). The organic layers were dried over Na$_2$SO$_4$ and concentrated to afford a white solid. This material was dissolved in a 2:1 mixture of CH$_2$Cl$_2$ and 2-methoxypropene (150 mL), and the resulting solution was treated with methanesulfonic acid (1.0 mL). After stirring 1 h at 23° C., the reaction mixture was partitioned between half-saturated NaHCO$_3$ (150 mL), and CH$_2$Cl$_2$ (2×100 mL). The combined organic layers were washed with H$_2$O (100 mL), dried over MgSO$_4$, and gravity filtered. The filtrate was concentrated, and the residue was purified by flash column chromatography (20% EtOAc in hexanes) to provide 3-p-tolyl-propionic acid cis-1S-amino-2R-indanol-acetonide amide (5.67 g, 51%) as a pale orange oil; R$_f$=0.63 (50% EtOAc in hexanes); IR (cm$^{-1}$) 2931, 1646; $^1$H NMR (CDCl$_3$) δ1.35 (s, 3H), 1.61 (s, 3H), 2.33 (s, 3H), 2.90–2.95 (m, 2H), 3.05–3.09 (m, 4H), 4.66–4.69 (m, 1H), 5.05 (d, 1H, J=4.7), 7.10–7.27 (m, 8H); Anal. (C$_{22}$H$_{25}$NO$_2$) C,H,N.

Preparation of Intermediate {1S-[4R-(4-Methyl-benzyl)-5-oxo-tetrahydro-furan-2S-yl]-2-phenyl-ethyl}-carbamic Acid tert-Butyl Ester n-Butyllithium (8.12 mL of a 1.6 M solution in hexanes, 13.0 mmol, 2.0 equiv) was added to a solution of (1R/S-oxiranyl-2S-phenyl-ethyl)-carbamic acid tert-butyl ester (1:1 mixture of isomers, 1.71 g, 6.49 mmol, 1 equiv) and 3-p-tolyl-propionic acid cis-1S-amino-2R-indanol-acetonide amide (2.18 g, 6.50 mmol, 1 equiv) in THF (100 mL) at −78° C. The reaction mixture was stirred for 10 min at −78° C., maintained at 0° C. for 1.5 h, and then partitioned between 0.5 M HCl (150 mL) and a 1:1 mixture of EtOAc and hexanes (2×150 mL). The organic layers were dried over Na$_2$SO$_4$ and concentrated. Falsh chromatographic purification of the residue (gradient elution, 20→30% EtOAc in hexanes) gave the coupling product (1.02 g, single isomer, 26%) as an orange oil contaminated with several minor impurities. This material was dissolved in a 5:1 mixture of toluene and CH$_2$Cl$_2$ (60 mL) and was treated with p-toluenesulfonic acid monohydrate (0.324 g, 1.70 mmol, 1.0 equiv) at 23° C. After stirring 12 h at 23° C., the reaction mixture was filtered through a medium frit, and the filtrate was partitioned between half-saturated NaHCO$_3$ (150 mL) and a 1:1 mixture of EtOAc and hexanes (2×100 mL). The organic layers were dried over Na$_2$SO$_4$ and concentrated. The residue was purified by flash column chromatography (15% EtOAc in hexanes) to provide {1S-[4R-(4-methyl-benzyl)-5-oxo-tetrahydro-furan-2S-yl]-2-phenyl-ethyl}-carbamic acid tert-butyl ester (0.26 g, 37%) as a white foam: R$_f$=0.60 (30% EtOAc in hexanes); IR (cm$^{-1}$) 3336, 1768, 1703; $^1$H NMR (CDCl$_3$) δ1.36 (s, 9H), 1.90–1.99 (m, 1H), 2.15–2.27 (m, 1H), 2.30 (s, 3H), 2.74 (dd, 1H, J=13.5, 8.6), 2.82–2.88 (m, 2H), 2.91–300 (m, 1H), 3.06 (dd, 1H, J=13.5, 4.5), 3.88–3.97 (m, 1H), 4.18–4.23 (m, 1H), 4.51 (d, 1H, J=9.7) 7.01–7.08 (m, 4H), 7.17–7.31 (m, 5H); Anal. (C$_{25}$H$_{31}$NO$_4$)C,H,N.

Preparation of Intermediate Ethyl-3-[BOC-L-PheΨ[COCH$_2$]-L-(p-CH$_3$)Phe-L-(Tr-Gln)]-E-Propenoate Lithium hydroxide (3.17 mL of a 1 M aqueous solution, 3.17 mmol, 5 equiv) was added to a solution of {1S-[4R-(4-methyl-benzyl)-5-oxo-tetrahydro-furan-2S-yl]-2-phenyl-ethyl}-carbamic acid tert-butyl ester (0.260 g, 0.635 mmol, 1 equiv) in DME (4 mL) at 23° C. The resulting suspension was stirred at 23° C. for 30 min and thenpartitioned between 0.5 M HCl (100 mL) and EtOAc (2×100 mL). The combined organic layers were dried over Na$_2$SO$_4$, concentrated, and the residue dissolved in a 1:1 mixture of CH$_3$CN and CH$_2$Cl$_2$ (60 mL). 4-Methylmorpholine N-oxide (0.149 g, 1.27 mmol, 2 equiv), powdered 4 Å molecular sieves (0.50 g), and tetrapropylammonium perruthenate (0.022 g, 0.063 mmol, 0.1 equiv) were added sequentially. The resulting dark reaction mixture was stirred for 1 h at 23° C. and then filtered through celite. The filtrate was concentrated under reduced pressure to provide a brown oil which was dissolved in CH$_2$Cl$_2$ (20 mL). Crude ethyl-3-[H$_2$-N-L-(Tr-Gln)]-E-propenoate.HCl (see preparation of ethyl-3-[CBZ-L-LeuΨ[COCH$_2$]-D/L-Phe-L-(Tr-Gln)]-E-propenoate, 0.762 mmol, 1.2 equiv), 1-hydroxybenzotriazole hydrate (0.112 g, 0.829 mmol, 1.3 equiv), 4-methylmorpholine (0.280 mL, 2.55 mmol, 4 equiv), and 1-(3-dimethylaminopropyl)-3-ethylcarbodiimide hydrochloride (0.158 g, 0.824 mmol, 1.3 equiv) were added sequentially, and the reaction mixture was stirred for 18 h at 23° C. and then partitioned between water (100 mL) and a 1:1 mixture of EtOAc and hexanes (2×100 mL). The combined organic layers were dried over Na$_2$SO$_4$ and concentrated. Purification of the residue by flash column chromatography (40% EtOAc in hexanes) provided ethyl-3-[BOC-L-PheΨ[COCH$_2$]-L-(p-CH$_3$)Phe-L-(Tr-Gln)]-E-propenoate (0.190 g, 35%) as a white foam: R$_f$=0.43 (50% EtOAc in hexanes); IR (cm$^{-1}$) 3314, 1710, 1665; $^1$H NMR (CDCl$_3$) δ1.28 (t, 3H, J=7.2), 1.35 (s, 9H), 1.63–1.65 (m, 1H), 1.97–2.05 (m, 1H), 2.33 (s, 3H), 2.36–2.38 (m, 2H), 2.48 (d, 1H, J=15.9), 2.57–2.64 (m, 2H), 2.75–3.00 (m, 4H), 4.17 (q, 2H, J=7.2), 4.25–4.32 (m, 1H), 4.52 (s, br, 1H), 4.77 (d, 1H, J=6.9), 5.53 (dd, 1H, J=15.9, 1.6), 5.94 (d, 1H, J=8.4), 6.63 (dd, 1H, J=15.9, 5.0), 6.99–7.09 (m, 5H), 7.11–7.32 (m, 20H); Anal. (C$_{53}$H$_{59}$N$_3$O$_7$)C,H,N.

Preparation of Intermediate Ethyl-3[CyPentylSCO-L-PheΨ[COCH$_2$]-L-(p-CH$_3$)Phe-L-(Tr-Gln)]-E-Propenoate HCl (5 mL of a 4.0 M solution in 1,4-dioxane) was added to a solution of ethyl-3-[BOC-L-PheΨ[COCH$_2$]-L-(p-CH$_3$) Phe-L-(Tr-Gln)]-E-propenoate (0.190 g, 0.224 mmol, 1 equiv) in 1,4-dioxane (6 mL). The reaction mixture was stirred at 23° C. for 1.5 h and then concentrated. The resulting oil was dissolved in CH$_2$Cl$_2$ (10 mL), cooled to 0° C., and 4-methylmorpholine (0.075 mL, 0.682 mmol, 3.0 equiv) and cyclopentyl chlorothiolformate (0.055 mL, 0.334 mmol, 1.5 equiv) were added sequentially. The reaction mixture was stirred for 1 h at 0° C. and then partitioned between water (100 mL) and a 1:1 mixture of EtOAc and hexanes (2×100 mL). The combined organic layers were dried over Na$_2$SO$_4$, concentrated, and the residue was chromatographed on silica gel (40% EtOAc in hexanes) to afford ethyl-3-[CyPentylSCO-L-PheΨ[COCH$_2$]-L-(p-CH$_3$)Phe-L-(Tr-Gln)]-E-propenoate (0.102 g, 50%) as an off-white foam: R$_f$=0.49 (50% EtOAc in hexanes); IR (cm$^{-1}$) 3316, 1718, 1655; $^1$H NMR (CDCl$_3$) δ1.29 (t, 3H, J=7.2), 1.45–1.67 (m, 7H), 1.98–2.05 (m, 2H), 2.33 (s, 3H), 2.42 (d, 1H, J=15.9), 2.55–2.98 (m, 6H), 3.52–3.63 (m, 1H), 4.17 (q, 2H, J=7.2), 4.38–4.54 9m, 2H), 5.52–5.58 (m, 2H), 6.03 (d, 1H, J=8.4), 6.64 (dd, 1H, J=15.9, 5.0), 6.95–7.08; (m, 5H), 7.11–7.32 (m, 21H); Anal. (C$_{54}$H$_{59}$N$_3$O$_6$S) C,H,N.

Preparation of Product Ethyl-3-(CyPentylSCO-L-PheΨ[COCH$_2$]-L-(p-CH$_3$)Phe-L-Gln)-E-Propenoate Triisopropylsilane (0.10 mL) and trifluoroacetic acid (5 mL) were added sequentially to a solution of ethyl-3-[CyPentylSCO-L-PheΨ[COCH$_2$]-L-(p-CH$_3$)Phe-L-(tr-Gln)]-E-propenoate (0.075 g, 0.085 mmol) in CH$_2$Cl$_2$ (6mL) producing a bright yellow solution. The reaction mixture was stirred for 15 min at 23° C., then carbon tetrachloride (5 mL) was added, and the mixture was concentrated under reduced pressure. The residue was purified by flash column chromatography (5% CH$_3$OH in CH$_2$Cl$_2$) to afford ethyl-3-(CyPentylSCO-L-Pheω[COCH$_2$]-L-(p-CH$_3$)Phe-L-Gln)-E-propenoate (0.047 g, 87%) as a white foam: R$_f$=0.62 (10% CH$_3$OH in CH$_2$Cl$_2$); IR (cm$^{-1}$) 3286, 1718, 1637; $^1$HNMR (DMSO-d$_6$) δ1.20 (t,3H, J=6.8), 1.33–1.70 (m, 10H), 1.91–2.07 (m, 4H), 2.24 (s, 3H), 2.38–3.05 (m, 5H), 3.42–3.46 (m, 1H), 4.07–4.11 (m, 2H), 4.34 (s, br, 2H), 5.58 (d, 1H, J=15.7), 6.67 (dd, 1H, J=15.7, 4.4), 6.76 (s, br, 1H), 7.02–7.25 (m,10H), 8.07 (d, 1H, J=7.8), 8.44 (d, 1H, J=7.5); Anal. (C$_{35}$H$_{45}$N$_3$O$_6$S) C,H,N.

EXAMPLE 13

Preparation of Compound 13: Ethyl-3-(EtSCO-L-ValΨ[COCH$_2$]-L-(p-F)Phe-L-Gln)-E-Propenoate Preparation of Intermediate trans-6-Methyl-2S-(4-fluoro benzyl)-hept-4-enoic Acid (2R-Hydroxy-1R-methyl-2-phenyl-ethyl)-methyl Amide n-Butyllithium (32.5 mL of a 1.6 M solution in hexanes, 52.0 mmol, 3.1 equiv) was added to a suspension of anhydrous lithium chloride (7.18 g, 169 mmol, 10 equiv) and diisopropylamine (7.80 mL, 55.7 mmol, 3.3 equiv) in THF (250 mL) at −78° C. The reaction mixture was stirred for 30 min at −78° C., then was maintained at 0° C. for 5 min, and subsequently was cooled again to −78° C. trans-6-Methyl-hept-4-enoic acid (2R-hydroxy-1R-methyl-2-phenyl-ethyl)-methyl amide (4.91 g, 17.0 mmol, 1 equiv) in THF (50 mL) was added via cannula, and the resulting solution was stirred at −78° C. for 1.75 h, maintained at 0° C. for 20 min, stirred at 23° C. for 5 min, and then cooled again to 0° C. A solution of 4-fluorobenzyl bromide (6.34 mL, 50.9 mmol, 3 equiv) in THF (15 mL) was added, and the reaction mixture was stirred at 0° C. for 30 min, and it then was partitioned between half-saturated NH$_4$Cl (230 mL) and a 1:1 mixture of EtOAc and hexanes (200 mL, 2×150 mL). The combined organic layers were dried over Na$_2$SO$_4$ and concentrated. Purification of the residue by flash column chromatography (gradient elution 20→40% EtOAc in hexanes) provided trans-6-methyl-2S-(4-fluoro-benzyl)-hept-4-enoic acid (2R-hydroxy-1R-methyl-2-phenyl-ethyl)-methyl amide (6.33 g, 94%) as a viscous oil: R$_f$=0.38 (40% EtOAc in hexanes); IR (cm$^{-1}$) 3378, 1614; $^1$H NMR (CDCl$_3$, mixture of rotamers) δ0.85–0.95 (m), 0.96 (d, J=6.8), 2.10–2.32 (m), 2.34–2.46 (m), 2.58 (s), 2.67–2.79 (m), 2.82–2.94 (m), 3.00–3.18 (m), 3.94 (br), 4.37–4.52 (m), 5.24–5.42 (m), 5.44–5.56 (m), 6.89–7.01 (m), 7.08–7.14 (m), 7.19–7.38 (m); Anal. (C$_{25}$H$_{32}$FNO$_2$) C,H,N.

Preparation of Intermediate 5S-(1R-Bromo-2-methyl-propyl)-3R-(4-fluoro-benzyl)-dihydrofuran-2one N-Bromosuccinimide (2.93 g, 16.5 mmol, 1.05 equiv) was added in small portions over 10 min to a solution of trans-6-methyl-2S-(4-fluoro-benzyl)-hept-4-enoic acid (2R-hydroxy-1R-methyl-2-phenyl-ethyl)-methyl amide (6.24 g, 15.7 mmol, 1 equiv) and glacial acetic acid (4.49 mL, 78.4 mmol, 5 equiv) in a 4:1 mixture of THF and H$_2$O (165 mL) at 0° C. The resulting yellow solution was stirred for 15 min at 0° C., then was warmed to 23° C., and subsequently was refluxed for 45 min. After cooling to 23° C., the reaction mixture was partitioned between half-saturated NaHCO$_3$ (200 mL) and a 1:1 mixture of EtOAc and hexanes (2×20 mL, 100 mL). The combined organic layers were dried over Na$_2$SO$_4$ and concentrated. Flash chromatographic purification of the residue (gradient elution 4→6→10% EtOAc in hexanes) gave 5S-(1R-bromo-2-methyl-propyl)-3R-(4-fluoro-benzyl)-dihydrofuran-2-one (4.14 g, 80%) as a pale yellow oil (containing approximately 5–10% unidentified impurities by $^1$H NMR): R$_f$=0.56 (25% EtOAc in hexanes); IR (cm$^{-1}$) 1772; $^1$H NMR (CDCl$_3$, major isomer) δ0.94 (d, 3H, J=6.5), 1.00 (d, 3H, J=6.8), 2.05–2.35 (m, 3H), 2.83 (dd, 1H, J=13.6, 8.4), 2.92–3.03 (m, 1H), 3.11 (dd, 1H, J=13.6, 4.7), 3.90 (dd, 1H, J=9.0, 3.7), 4.33–4.40 (m, 1H), 6.98–7.06 (m, 2H), 7.14–7.20 (m, 2H); Anal. (C$_{15}$H$_{18}$BrFO$_2$) C,H.

Preparation of Intermediate 5S-(1S-Azido-2-methyl-propyl)-3R-(4-fluoro-benzyl)-dihydrofuran-2one A suspension of sodium azide (1.90 g, 29.2 mmol, 2.5 equiv) and 5S-(1R-bromo-2-methyl-propyl)-3R-(4-fluoro-benzyl)-dihydrofuran-2-one (3.85 g, 11.7 mmol, 1 equiv) in N,N-dimethylformamide (40 mL) was heated at 50° C. for 67 hours. The reaction mixture was cooled to 23° C. and partitioned betwen half-saturated NaCl (200 mL) and a 1:1:1 mixture of EtOAc, hexanes, and acetone (2×200 mL, 100 mL). The combined organic layers were dried over Na$_2$SO$_4$, concentrated, and the residue purified by flash column chromatography (gradient elution 9→12→17% EtOAc in hexanes) to give 5S-(1S-azido-2-methyl-propyl)-3R-(4-fluoro-benzyl)-dihydrofuran-2-one (2.10 g, 62%) as a white solid (containing approximately 5–10% unidentified impurities by $^1$H NMR): mp 91–96° C.; R$_f$=0.44 (25% EtOAc in hexanes); IR (cm$^{-1}$) 2097, 1772; $^1$H NMR (CDCl$_3$, major isomer) δ0.99 (d, 3H, J=6.5), 1.03 (d, 3H, J=6.8), 1.95–2.20 (m, 3H), 2.78–2.88 (m, 1H), 2.94 (dd, 1H, J=7.0, 4.2), 3.03–3.17 (m, 2H), 4.37–4.43 (m, 1H), 6.97–7.09 (m, 2H), 7.14–7.21 (m, 2H).

Preparation of Intermediate {2-Methyl-1S-[4-R-(4-fluoro-benzyl)-5-oxo-tetrahydrofuran-2S-yl]-propyl}-carbamic Acid tert-Butyl Ester A suspension of 5S-(1S-azido-2-methyl-propyl)-3R-(4-fluoro-benzyl)-dihydrofuran-2-one (2.02 g, 6.93 mmol, 1 equiv), di-tert-butyl dicarbonate (2.12 g, 9.71 mmol, 1.4 equiv) and Pd/C (10%, 0.20 g) in CH$_3$OH (100 mL) was stirred under a hydrogen atmosphere (balloon) for 16 hours. The reaction mixture was vacuum filtered through Whatman #3 paper and concentrated. Purification of the residue by flash column chromatography (15% EtOAc in hexanes) provided {2-methyl-1S-[4R-(4-fluoro-benzyl)-5-oxo-tetrahydrofuran-2S-yl]-propyl}-carbamic acid tert-butyl ester (1.58 g, 62%) as a white foam: R$_f$=0.80 (5% MeOH in CH$_2$Cl$_2$); IR (cm$^{-1}$) 3331, 1766, 1702; $^1$H NMR (CDCl$_3$) δ0.93 (d, 3H, J=6.8), 0.95 (d, 3H, J=6.5), 1.41 (s, 9H), 1.71–1.83 (m, 1H), 1.95–2.06 (m, 1H), 2.16–2.27 (m, 1H), 2.80 (dd, 1H, J=13.5, 8.6), 2.88–2.99 (m, 1H), 3.09 (dd, 1H, J=13.5, 4.4), 3.32–3.40 (m, 1H), 4.42–4.48 (m, 2H), 6.95–7.03 (m, 2H), 7.11–7.18 (m, 2H); Anal. (C$_{20}$H$_{28}$FNO$_4$) C,H,N.

Preparation of Intermediate Ethyl-3-[BOC-L-ValΨ[COCH$_2$]-L-(p-F)Phe-L-(Tr-Gln)]-E-Propenoate Lithium hydroxide (9.62mL of a 1 M aqueous solution, 9.62 mmol, 5 equiv) was added to a solution of {2-methyl-1S-[4R-(4-fluoro-benzyl)-5-oxo-tetrahydrofuran-2S-yl]-propyl}-carbamic acid tert-butyl ester (0.703 g, 1.92 mmol, 1 equiv) in DME (25 mL) at 23° C. The resulting suspension was stirred at 23° C. for 30 min, and it then was partitioned between 10% KHSO$_4$ (50 mL) and CH$_2$Cl$_2$ (3×100 mL). The combined organic layers were dried over Na$_2$SO$_4$, concentrated, and the residue dissolved in CH$_2$Cl$_2$ (30 mL). Powdered 4 Å molecular sieves (0.70 g), 4-methylmorpholine N-oxide (0.451 g, 3.85 mmol, 2 equiv), and tetrapropylammonium perruthenate (0.068 g, 0.19 mmol, 0.10 equiv) were added sequentially. The resulting dark reaction mixture was stirred for 1.33 hours at 23° C., and it then was vacuum filtered through Whatman #3 paper and then through Whatman #5 paper. The filtrate was concentrated under reduced pressure to provide a dark residue which was dissolvd in $CH_2Cl_2$ (30 mL). Crude ethyl-3-[$H_2$N-L-(Tr-Gln)]-E-propenoate.HCl (2.30 mmol, 1.2 equiv, prepared as described in Example 1 for the preparation of ethyl-3-[CBZ-L-LeuΨ[$COCH_2$]-D/L-Phe-L-(Tr-Gln)]-E-propenoate, 4-methylmorpholine (0.846 mL, 7.69 mmol, 4 equiv), 1-hydroxybenzotriazole hydrate (0.390 g, 2.89 mmol, 1.5 equiv), and 1-(3-dimethylaminopropyl)-3-ethylcarbodiimide hydrochloride (0.553 g, 2.88 mmol, 1.5 equiv) were added sequentially, and the reaction mixture was stirred for 19 hours at 23° C. and then partitioned between brine (100 mL) and $CH_2Cl_2$ (3×100 mL). The combined organic layers were dried over $Na_2SO_4$ and concentrated. Purification of the residue by flash column chromatography (gradient elution 35→40% EtOAc in hexanes) provided ethyl-3-[BOC-L-ValΨ[$COCH_2$]-L-(p-F)Phe-L-(Tr-Gln)]-E-propenoate (0.820 g, 53%) as a tan foam: $R_f$=0.50 (50% EtOAc in hexanes); IR (cm$^{-1}$) 3307, 1708, 1666; $^1$H NMR (CDCl$_3$) δ0.67 (d, 3H, J=6.8), 0.92 (d, 3H, J=6.8), 1.28 (t, 3H, J=7.2), 1.40 (s, 9H), 1.53–1.67 (m, 1H), 1.91–2.04 (m, 2H), 2.32–2.41 (m, 2H), 2.46–2.55 (m, 1H), 2.63 (dd, 1H, J=12.1, 5.9), 2.69–2.80 (m, 1H), 2.83 (dd, 1H, J=12.1, 8.2), 3.03 (dd, 1H, J=17.7, 10.0), 4.05–4.11 (m, 1H), 4.17 (q, 2H, J=7.2), 4.40–4.50 (m, 1H), 4.84 (d, 1H, J=8.4), 5.38 (d, 1H, J=15.7), 6.01 (d, 1H, J=8.4), 6.60 (dd, 1H, J=15.7, 5.0) 6.92–6.99 (m, 2H), 7.03–7.12 (m, 3H), 7.17–7.30 (m, 15H); Anal. ($C_{48}H_{56}FN_3O_7$) C,H,N.

Preparation of Intermediate Ethyl-3-[EtSCO-L-ValΨ[$COCH_2$]-L-(p-F)Phe-L-(Tr-Gln)]-E-Propenoate HCl (3 mL of a 4.0 M solution in 1,4-dioxane) was added to a solution of ethyl-3-[BOC-L-ValΨ[$COCH_2$]-L-(p-F)Phe-L-(Tr-Gln)]-E-propenoate (0.271 g, 0.336 mmol) in 1,4-dioxane (3 mL). The reaction solution was stirred at 23° C. for 2 hours and then was concentrated. The residue was dissolved in dry $CH_2Cl_2$ (5 mL). N,N-diisopropylethylamine (0.176 mL, 1.01 mmol, 3 equiv) and ethyl chlorothiolformate (0.060 mL, 0.58 mmol, 1.7 equiv) were added sequentially. The reaction solution was stirred 2 hours at 23° C. and then was partitioned between brine (30 mL) and $CH_2Cl_2$ (3×30 mL). The combined organic phases were dried over $Na_2SO_4$, concentrated, and the residue was chromatographed on silica gel (gradient elution 40→50% EtOAc in hexanes) to afford ethyl-3-[EtSCO-L-ValΨ[$COCH_2$]-L-(p-F)Phe-L-(Tr-Gln)]-E-propenoate (0.183 g, 69%) as a white foam: $R_f$=0.43 (50% EtOAc in hexanes); IR (cm$^{-1}$) 3307, 1708, 1655; $^1$H NMR (CDCl$_3$) δ0.70 (d, 3H, J=6.8), 0.93 (d, 3H, J=6.5), 1.25 (t, 3H, J=7.2), 1.29 (t, 3H, J=7.2), 1.55–1.66 (m, 1H), 1.91–2.05 (m, 2H), 2.30–2.39 (m, 2H), 2.51 (dd, 1H, J=2.5), 2.63 (dd, 1H, J=12.1, 5.9), 2.69–2.90 (m, 4H), 3.02 (dd, 1H, J=17.4, 10.0), 4.17 (q, 2H, J=7.2), 4.35–4.49 (m, 2H), 5.39 (dd, 1H, J=15.6, 1.7), 5.66 (d, 1H, J=8.1), 6.12 (d, 1H, J=8.1), 6.60 (dd, 1H, J=15.6, 5.0), 6.91–6.99 (m, 2H), 7.02–7.10 (m, 2H), 7.17–7.32 (m, 16H); Anal. ($C_{46}H_{52}FN_3O_6S$) C,H,N.

Preparation of Product Ethyl-3-(EtSCO-L-ValΨ[$COCH_2$]-L-(p-F)Phe-L-Gln)-E-Propenoate Ethyl-3-[EtSCO-L-ValΨ[$COCH_2$]-L-(p-F)Phe-L-(Tr-Gln)]-E-propenoate (0.149 g, 0.188 mmol, 1 equiv) was dissolved in dry $CH_2Cl_2$ (6 mL). Triisopropylsilane (0.115 mL, 0.561 mmol, 3 equiv) and trifluoroacetic acid (3 mL) were added sequentially producing a bright yellow solution. This solution was stirred for 30 minutes and then concentrated. The residue was stirred in $Et_2O$ (6 mL), and the solid was collected by filtration, washed with $Et_2O$ (3 mL then 2 mL), and then dried under vacuum to give ethyl-3-(EtSCO-L-ValΨ[$COCH_2$]-L-(p-F)Phe-L-Gln)-E-propenoate (0.090 g, 87%) as a white slid: mp=214° C. (dec); $R_f$=0.49 (10% $CH_3OH$ in $CH_2Cl_2$); IR (cm$^{-1}$) 3425, 3284, 1713, 1643; $^1$H NMR (DMSO-d$_6$) δ0.76 (d, 3H, J=6.5), 0.82 (d, 3H, J=6.8), 1.15 (t, 3H, J=7.2), 1.21 (t, 3H, J=7.2), 1.53–1.75 (m, 2H), 1.99–2.14 (m, 3H), 2.52–2.85 (m, 6H), 2.88–2.99 (m, 1H), 4.09 (q, 2H, J=7.2), 4.13–4.20 (m, 1H), 4.25–4.36 (m, 1H), 5.40 (dd, 1H, J=15.6, 1.4), 6.61 (dd,1H, J=15.6, 5.3), 6.74 (s, 1H), 6.99–7.24 (m, 5H), 8.01 (d, 1H, J=8.1), 8.34 (d, 1H, J=8.1); Anal. ($C_{27}H_{38}FN_3O_6S$) C,H,N.

EXAMPLE 14

Preparation of Compound 14: Ethyl-3-(CyPentylSCO-L-ValΨ[$COCH_2$]-L-(p-F)Phe-L-Gln)-E-Propenoate Preparation of Intermediate Ethyl-3-[CyPentylSCO-L-ValΨ[$COCH_2$]-L-(p-F)Phe-L-(tr-Gln)]-E-Propenoate HCl (3mL of a 4.0 solution in 1,4-dioxane) was added to a solution of ethyl-3-[BOC-L-ValΨ[$COCH_2$]-L-(p-F)Phe-L-(Tr-Gln)]-E-propenoate (0.273 g, 0.339 mmol) in 1,4-dioxane (3 mL). The reaction solution was stirred at 23° C. for 2 hours and then concentrated. The residue was dissolved in dry $CH_2Cl_2$ (5 mL). N,N-diisopropylethylamine (0.177 mL, 1.02 mmol, 3 equiv) and cyclopentyl chlorothiolformate (0.095 mL, 1.7 equiv) were added sequentially. The reaction solution was stirred 2 hours at 23° C. and then partitioned between brine (30 mL) and $CH_2Cl_2$ (3×30 mL). The combined organic phases were dried over $Na_2SO_4$, concentrated, and the residue was chromatographed on silica gel (40% EtOAc in hexanes) to afford ethyl-3-[CyPentylSCO-L-ValΨ[$COCH_2$]-L-(p-F)Phe-L-(Tr-Gln)]-E-propenoate (0.166 g, 59%) as a white foam: $R_f$=0.24 (40% EtOAc in hexanes); IR (cm$^{-1}$) 3307, 1713, 1654; $^1$H NMR (CDCl$_3$) δ0.69 (d, 3H, J=6.8), 0.93 (d, 3H, J=6.8), 1.29 (t, 3H, J=7.2), 1.47–1.75 (m, 7H), 1.91–2.12 (m, 4H), 2.30–2.41 (m, 2H), 2.51 (dd, 1H, J=17.2, 2.3), 2.63 (dd, 1H, J=1.23, 5.9), 2.69–2.80 (m, 1H), 2.84 (dd, 1H, J=12.3, 8.4), 3.01 (dd, 1H, J=17.2, 10.0), 3.57–3.67 (m, 1H), 4.17 (q, 2H, J=7.2), 4.33–4.50 (m, 2H), 5.39 (dd, 1H, J=15.7, 1.7), 5.61 (d, 1H, J=7.8), 6.11 (d, 1H, J=8.1), 6.60 (dd, 1H, J=15.7, 4.8), 6.92–7.00 (m, 2H), 7.03–7.12 (m, 3H), 7.18–7.32 (m, 15H); Anal. ($C_{49}H_{56}FN_3O_6$.0.5$H_2O$) C,H,N.

Preparation of Product Ethyl-3-(CyPentylSCO-L-ValΨ[$COCH_2$]-L-(p-F)Phe-L-Gln)-E-Propenoate Ethyl-3[CyPentylSCO-L-ValΨ[$COCH_2$]-L-(p-F)Phe-L-(Tr-Gln)]-E-propenoate (0.132 g, 0.158 mmol, 1 equiv) was dissolved in dry $CH_2Cl_2$ (6 mL). Triisopropylsilane (0.097 mL, 0.47 mmol, 3 equiv) and trifluoroacetic acid (3 mL) were added sequentially producing a bright yellow solution. This solution was stirred for 30 minutes and then concentrated. The residue was stirred in $Et_2O$ (6 mL), and the solid was collected by filtration, washed with $Et_2O$ (3 mL then 2 mL), and then dried under vacuum to give ethyl-3-(CyPentylSCO-L-ValΨ[$COCH_2$]-L-(p-F)Phe-L-Gln)-E-propenoate (0.077 g, 82%) as a white solid: mp=215° C. (dec); $R_f$=0.45 (10% $CH_3OH$ in $CH_2Cl_2$); IR (cm$^{-1}$) 3413, 3296, 1715, 1649; $^1$H NMR (DMSO-d$_6$) δ0.75 (d, 3H, J=6.5), 0.82 (d, 3H, J=6.5), 1.21 (t, 3H, J=6.9), 1.36–1.75 (m, 8H), 1.92–2.14 (m, 5H), 2.52–2.85 (m, 4H), 2.87–2.99 (m, 1H), 3.47–3.58 (m, 1H), 4.06–4.18 (m, 1H), 4.09 (q, 2H, J=6.9), 4.25–4.36 (m, 1H), 5.41 (d, 1H, J=15.6), 6.61 (dd, 1H, J=15.6, 5.1), 6.74 (s, 1H), 6.98–7.23 (m, 5H), 8.01 (d, 1H, J=8.4), 8.28 (d, 1H, J=8.1); Anal. ($C_{3.}H_{42}FN_3O_6S$.0.25 $H_2O$) C,H,N.

EXAMPLE 15

Preparation of Compound 15: Ethyl-3-(EtSCO-L-ValΨ[COCH$_2$]-L-(p-CF$_3$)Phe-L-Gln)-E-Propenoate Preparation of Intermediate trans-6-Methyl-2S-(4-trifluoromethyl-benzyl)-hept-4-enoic Acid (2R-Hydroxy-1R-methyl-2-phenyl-thyl)-methyl Amide n-Butyllithium (25.5 mL of a 1.6 M solution in hexanes, 40.8 mmol, 2.15 equiv) was added to a suspension of anhydrous lithium chloride (5.64 g, 133 mmol, 7 equiv) and diisopropylamine (6.13 mL, 43.7 mmol, 2.3 equiv) in THF (200 mL) at −78° C. The reaction mixture was stirred for 30 min at −78° C., then maintained at 0° C. for 5 min, and subsequently cooled again to −78° C. trans-6-Methyl-hept-4-enoic acid (2R-hydroxy-1R-methyl-2-phenyl-ethyl)-methyl amide (5.5 g, 19.0 mmol, 1 equiv) in THF (40 mL) was added via cannula, and the resulting solution was stirred at −78° C. for 1.75 h, maintained at 0° C. for 20 min, stirred at 23° C. for 5 min, and then cooled again to 0° C. A solution of 4-trifluoromethylbenzyl bromide (6.81 g, 28.5 mmol, 1.5 equiv) in THF (10 mL) was added, and the reaction mixture was stirred at 0° C. for 30 min and then partitioned between half-saturated NH$_4$Cl (230 mL) and a 1:1 mixture of EtOAc and hexanes (200 mL, 2×150 mL). The combined organic layers were dried over Na$_2$SO$_4$ and concentrated. Purification of the residue by flash column chromatography (gradient elution 20→40% EtOAc in hexanes) provided trans-6-methyl-2S-(4-trifluoromethyl-benzyl)-hept-4-enoic acid (2R-hydroxy-1R-methyl-2-phenyl-ethyl)-methyl amide (7.64 g, 90%) as viscous oil: R$_f$=0.47 (40% EtOAc in hexanes); IR (cm$^{-1}$) 3378, 1619; $^1$H NMR (CDCl$_3$, mixture of rotamers) δ0.85 (d, J=6.5), 0.89 (d, J=6.5), 0.91 (d, J=6.5), 0.96 (d, J=6.8), 2.07–2.34 (m), 2.36–2.47 (m), 2.59 (s), 2.76–2.86 (m), 2.88–3.01 (m), 3.07–3.22 (m), 3.96 (br), 3.99–4.09 (m), 4.37–4.52 (m), 5.19–5.57 (m), 7.19–7.40 (m), 7.47–7.57 (m).

Preparation of Intermediate 5S-(1R-Bromo-2-methyl-propyl)-3R-(4-trifluoromethyl-benzyl)-dihydrofuran-2one N-Bromosuccinimide (3.17 g, 17.8 mmol, 1.05 equiv) was added in small portions over 10 min to a solution of trans-6-methyl-2S-(4-trifluoromethyl-benzyl)-hept-4-enoic acid (2R-hydroxy-1R-methyl-2-phenyl-ethyl)-methyl amide (7.58 g, 16.9 mmol, 1 equiv) and glacial acetic acid (4.85 mL, 84.7 mmol, 5 equiv) in a 4:1 mixture of THF and H$_2$O (180 mL) at 0° C. The resulting yellow solution was stirred for 15 min at 0° C., then warmed to 23° C., and subsequently refluxed for 45 min. After cooling to 23° C., the reaction mixture was partitioned between half-saturated NaHCO$_3$ (200 mL) and a 1:1 mixture of EtOAc and hexanes (2×200 mL, 100 mL). The combined organic layers were dried over Na$_2$SO$_4$ and concentrated. Flash chromatographic purification of the residue (gradient elution 5→9→12% EtOAc in hexanes) gave 5S-(1R-bromo-2-methyl-propyl)-3R-(4-trifluoromethyl-benzyl)-dihydrofuran-2-one (5.28 g, 82%) as a white solid (containing approximately 5–10% unidentified impurities by $^1$H NMR): mp=83–85° C.; R$_f$=0.60 (25% EtOAc in hexanes); IR (cm$^{-1}$) 1778; $^1$HNMR (CDCl$_3$, major isomer) δ0.95 (d, 3H, J=6.5), 1.01 (d, 3H, J=6.8), 2.05–2.25 (m, 2H), 2.28–2.38 (m, 1H), 2.89 (dd, 1H, J=13.5, 8.9), 2.98–3.09 (m, 1H), 3.22 (dd, 1H, J=13.5, 4.5), 3.91 (dd, 1H, J=8.9, 3.6), 4.40–4.49 (m, 1H), 7.34 (d, 2H, J=8.1), 7.59 (d, 2H, J=8.1); Anal. (C$_{16}$H$_{18}$BrF$_3$O$_2$) C,H.

Preparation of Intermediate 5S-(1S-Azido-2-methyl-propyl)-3R-(4-trifluoromethyl-benzyl)-dihydrofuran-2one A suspension of sodium azide (2.22 g, 34.1 mmol, 2.5 equiv) and 5S-(1R-bromo-2-methyl-propyl)-3R-(4-trifluoromethyl-benzyl)-dihydrofuran-2-one (5.18 g, 13.7 mmol, 1 equiv) in N,N-dimethylformamide (50 mL) was heated at 50° C. for 66 hours. The reaction mixture was cooled to 23° C. and partitioned between half-saturated NaCl (200 mL) and a 1:1 mixture of EtOAc and hexanes (3×200 mL). The combined organic layers were dried over Na$_2$SO$_4$, concentrated, and the residue purified by flash column chromatography (gradient elution 9→12→20% EtOAc in hexanes) to give 5S-(1S-azido-2-methyl-propyl)-3R-(4-trifluoromethyl-benzyl)-dihydrofuran-2-one (2.77 g, 59%) as a viscous oil (containing approximately 5–10% unidentified impurities by $^1$H NMR):R$_f$=0.42 (25% EtOAc in hexanes); IR (cm$^{-1}$) 2097, 1772; $^1$H NMR (CDCl$_3$, major isomer) δ 1.01 (d, 3H, J=6.5), 1.02 (d, 3H, J=6.8), 1.96–2.23 (m, 3H), 2.84–2.98 (m, 2H), 3.09–3.20 (m, 1H), 3.25 (dd, 1H, J=13.7, 4.7), 4.44–4.52 (m, 1H), 7.34 (d, 2H, J=8.1), 7.59 (d, 2H, J=8.1); Anal (C$_{16}$H$_{18}$F$_3$N$_3$O$_2$) C, H, N.

Preparation of Intermediate {2-Methyl-1S-[4R-(4-trifluoromethyl-benzyl)-5-oxo-tetrahydrofuran-2S-yl]-propyl}-carbamic Acid tert-Butyl Ester.

A suspension of 5S-(1S-azido-2-methyl-propyl)-3R-(4-trifluoromethyl-benzyl)-dihydrofuran-2-one (2.71 g, 7.94 mmol, 1equiv), di-tert-butyl dicarbonate (2.43 g, 11.1 mmol, 1.4 equiv) and Pd/C (10%, 0.225 g) in CH$_3$OH (110 mL) was stirred under a hydrogen atmosphere (balloon) for 5 hours. The reaction mixture was vacuum filtered through Whatman #5 paper and concentrated. Purification of the residue by flash column chromatography (gradient elution 12→20% EtOAc in hexanes) provided {2-methyl-1S-[4R-(4-trifluoromethyl-benzyl)-5-oxo-tetrahydrofuran-2S-yl]-propyl}-carbamic acid tert-butyl ester (1.87 g, 57%) as a white foam: F$_f$=0.84 (5% MeOH in CH$_2$Cl$_2$); IR (cm$^{-1}$) 3331, 1766, 1708, 1690; $^1$H NMR (CDCl$_3$) δ 0.94 (d, 3H, J=6.8), 0.96 (d, 3H, J=6.5), 1.40 (s, 9H), 1.71–1.86 (m, 1H), 1.95–2.06 (m, 1H), 2.20–2.31 (m, 1H), 2.86 (dd, 1H, J=13.5, 8.9), 2.93–3.04 (m, 1H), 3.20 (dd, 1H, J=13.5, 4.2), 3.33–3.42 (m, 1H), 4.41–4.56 (m, 2H), 7.31 (d, 2H, J=8.1), 7.56 (d, 2H, J=8.1); Anal. (C$_{21}$H$_{28}$F$_3$NO$_4$) C, H, N.

Preparation of Intermediate Ethyl-3-[BOC(L-ValΨ[COCH$_2$]-L-(p-CF$_3$)Phe-L-(Tr-Gln)]-E-Propenoate.

Lithium hydroxide (8.8 mL of a 1M aqueous solution, 8.8 mmol, 5 equiv) was added to a solution of {2-methyl-1S-[4R-(4-trifluoromethyl-benzyl)-5-oxo-tetrahydrofuran-2S-yl]-propyl}-carbamic acid tert-butyl ester (0.731 g, 1.76 mmol, 1 equiv) in DME (25 mL) as 23° C. The resulting suspension was stirred at 23° C. for 30 min and then partitioned between 10% KHSO$_4$ (35 mL) and CH$_2$Cl$_2$ (2×100 mL, 70 mL). The combined organic layers were dried over Na$_2$SO$_4$, concentrated, and the residue dissolved in CH$_2$Cl$_2$/CH$_3$CN 10:1 (33 mL). Powdered 4 Å molecular sieves (0.65 g), 4-methylmorpholine N-oxide (0.412 g, 3.52 mmol, 2 equiv), and tetrapropylammonium perruthenate (0.062 g, 0.18 mmol, 0.10 equiv) were added sequentially. The resulting dark reaction mixture was stirred for 2 hours at 23° C., and then vacuum filtered through Whatman #5 paper. The filtrate was then transferred to a flask containing crude ethyl-3-[H$_2$N-L-(Tr-Gln)]-E-propenoate•HCl (2.12 mmol, 1.2 equiv, prepared as described in Example 1 for the preparation of ethyl-3-[CBZ-L-LeuΨ[COCH$_2$]-D/L-Phe-L-(Tr-Gln)]-E-propenoate), 4-methylmorpholine (0.774 mL, 7.04 mmol, 4 equiv), 1-hydroxybenzotriazole hydrate (0.357 g, 2.64 mmol, 1.5 equiv), and 1-(3-dimethylaminopropyl)-3-ethylcarbodiimide hydrochloride (0.506 g, 2.64 mmol, 1.5 equiv) were added sequentially, and the reaction mixture was stirred for 17 hours at 23° C. This mixture then was partitioned between brine (100 mL) and EtOAc (3×100 mL). The combined organic layers were dried over Na$_2$SO$_4$ and concentrated. Purification of the residue by flash column chromatography (40% EtOAc in hexanes) provided ethyl- 3-[BOC-L-ValΨ[COCH$_2$]-L-(p-CF$_3$)Phe-L-(Tr-Gln)]-E-propenoate (0.839 g, 56%) as a tan foam: R$_f$=0.27 (40% EtOAc in hexanes); IR (cm$^{-1}$) 3308, 1711, 1666; $^1$H NMR (CDCl$_3$) δ 0.67 (d, 3H, J=6.5), 0.92 (d, 3H, J=6.5), 1.27 (t, 3H, J=7.2), 1.39 (s, 9H), 1.58–1.71 (m, 1H), 1.90 –2.06 (m, 2H), 2.35–2.50 (m, 3H), 2.65–2.84 (m, 2H), 2.89–3.07 (m, 2H), 4.03–4.22 (m, 3H), 4.38–4.45 (m, 1H), 4.86 (d, 1H, J=8.1), 5.51 (d, 1H, J=15.6), 6.32 (d, 1H, J=8.1), 6.62 (dd, 1H, J=15.6, 5.0 ), 7.10 (s, 1H), 7.17–7.31 (m, 17H), 7.53 (d, 2H, J=7.8); Anal. (C$_{49}$H$_{56}$F$_3$N$_3$O$_7$•0.5H$_2$O) C, H, N.

Preparation of Intermediate Ethyl-3-[EtSCO-L-ValΨ[COCH$_2$]-L-(p-CF$_3$)Phe-L-(Tr-Gln)]-E-propenoate.

HCl (3 mL of a 4.0M solution in 1,4-dioxane) was added to a solution of ethyl-3-[BOC-L-ValΨ[COCH$_2$]-L-(p-CF$_3$)Phe-L-(Tr-Gln)]-E-propenoate (0.271 g, 0.317 mmol) in 1,4-dioxane (3 mL). The reaction solution was stirred at 23° C. for 2 hours and then concentrated. The residue was dissolved in dry CH$_2$Cl$_2$ (5 mL). N,N-diisopropylethylamine (0.165 mL, 0.947 mmol, 3 equiv) and ethyl chlorothiolformate (0.056 mL, 0.54 mmol, 1.7 equiv) were added sequentially. The reaction solution was stirred 2 hours at 23° C. and then partitioned between brine (30 mL) and CH$_2$Cl$_2$ (3×30 mL). The combined organic phases were dried over Na$_2$SO$_4$, concentrated, and the residue was chromatographed on silica gel (40% EtOAc in hexanes) to afford ethyl-3-[EtSCO-L-ValΨ[COCH$_2$]-L-(p-CF$_3$)Phe-L-(Tr-Gln)]-E-propenoate (0.142 g, 53%) as a white foam: R$_f$=0.25 (40% EtOAc in hexanes); IR (cm$^{-1}$) 3304, 1713, 1653; $^1$H NMR (CDCl$_3$) δ 0.70 (d, 3H, J=6.8), 0.94 (d, 3H, J=6.5), 1.24 (t, 3H, J=7.5) 1.27 (t, 3H, J=7.2), 1.59–1.72 (m, 1H), 1.91–2.04 (m, 2H), 2.33–2.51 (m, 3H), 2.65–3.08 (m, 6H), 4.08–4.22 (m, 2H), 4.34–4.48 (m, 2H), 5.52 (dd, 1H, J=15.7, 1.7), 5.66 (d, 1H, J=8.1), 6.39 (d, 1H, J=7.8), 6.62 (dd, 1H, J=15.7, 5.1), 7.04 (s, 1H), 7.17–7.30 (m, 17H), 7.53 (d, 2H, J=7.8).

Preparation of Product Ethyl-3-(EtSCO-L-ValΨ[COCH$_2$]-L-(p-CF$_3$)Phe-L-Gln)-E-Propenoate.

Ethyl-3-[EtSCO-L-ValΨ[COCH$_2$]-L-(p-CF$_3$)Phe-L-(Tr-Gln)]-E-propenoate (0.112 g, 0.133 mmol, 1 equiv) was dissolved in dry CH$_2$Cl$_2$ (6 mL). Triisopropylsilane ) 0.082 mL, 0.40 mmol, 3 equiv) and trifluoroacetic acid (3 mL) were added sequentially producing a bright yellow solution. This solution was stirred for 40 minutes and then concentrated. The residue was stirred in Et$_2$O (6 mL), and the solid was collected by filtration, washed with Et$_2$O (2×3 mL), and then dried under vacuum to give ethyl-3-(EtSCO-L-ValΨ[COCH$_2$]-L-(p-CF$_3$)Phe-L-Gln)-E-propenoate (0.068 g, 85%) as a white solid: mp=216° C. (dec); R$_f$=0.43 (10% CH$_3$OH in CH$_2$Cl$_2$); IR (cm$^{-1}$) 3425, 3308, 1717, 1655; $^1$H NMR (DMSO-d$_6$) δ 0.76 (d, 3H, J=6.5), 0.82 (d, 3H, J=6.5) d, 3H, J=6.5), 1.12–1.23 (m, 6H), 1.53–1.75 (m, 2H), 1.99–2.14 (m, 3H), 2.50–2.60 (m, 1H), 2.64–2.87 (m, 5H), 2.93–3.04 (m, 1H), 3.98–4.21 (m, 3H), 4.26–4.36 (m, 1H), 5.50 (d, 1H, J=15.5), 6.62 (dd, 1H, J=15.5, 5.4), 6.74 (s, 1H), 7.15 (s, 1H), 7.37 (d, 2H, J=8.1), 7.59 (d, 2H, J=8.1), 8.06 (d, 1H, J=8.1), 8.35 (d, 1H, J=8.1); Anal. (C$_{28}$H$_{38}$F$_3$N$_3$O$_6$S) C, H, N.

EXAMPLE 16

Preparation of Compound 16: Ethyl-3-(CyPentylSCO-L-ValΨ[COCH$_2$]- L-(p-CF$_3$)Phe-L-Gln)-E-Propenoate Preparation of Intermediate Ethyl-3-[CyPentylSCO-L-ValΨ[COCH$_2$]-L-(p-CF$_3$)Phe-L-(Tr-Gln)]-E-Propenoate.

HCl (3mL of a 4.0M solution in 1,4-dioxane) was added to a solution of ethyl-3-[BOC-L-ValΨ[COCH$_2$]-L-(p-CF$_3$)Phe-L-(Tr-Gln)]-E-propenoate (0.268 g, 0.313 mmol) in 1,4-dioxane (3 mL). The reaction solution was stirred at 23° C. for 2 hours and then concentrated. The residue was dissolved in dry CH$_2$Cl$_2$ (5 mL). N,N-diisopropylethylamine (0.164 mL, 0.941 mmol, 3 equiv) and cyclopentyl chlorothiolformate (0.088 mL, 1.7 equiv) were added sequentially. The reaction solution was stirred 3 hours at 23° C. and then was partitioned between brine (30 mL) and CH$_2$Cl$_2$ (3×30 mL). The combined organic phases were dried over Na$_2$SO$_4$, concentrated, and the residue was chromatographed on silica gel (40% EtOAc in hexanes) to afford ethyl-3-[CyPentylSCO-L-ValΨ[COCH$_2$]-L-(p-CF$_3$)Phe-L-(Tr-Gln)]-E-propenoate (0.169 g, 61%) as a white foam: R$_f$=0.25 (40% EtOAc in hexanes); IR (cm$^{-1}$) 3324, 1718, 1657; $^1$H NMR (CDCl$_3$) δ 0.70 (d, 3H, J=6.8), 0.93 (d, 3H, J=6.5), 1.27 (t, 3H, J=7.2), 1.46–1.73 (m, 7H), 1.91–2.12 (m, 4H), 2.30–2.52 (m, 3H), 2.65–2.83 (m, 2H), 2.90–3.06 (m, 2H), 3.56–3.66 (m, 1H), 4.08–4.22 (m, 2H), 4.31–4.49 (m, 2H), 5.51 (dd, 1H, J=15.8, 1.6), 5.65 (d, 1H, J=7.8), 6.40 (d, 1H, J=7.8), 6.62 (dd, 1H, J=15.8, 5.1), 7.08 (s, 1H), 7.17–7.30 (m, 17H), 7.53 (d, 2H, J=8.1); Anal. (C$_{50}$H$_{56}$F$_3$N$_3$O$_6$S•0.5H$_2$O) C, H, N.

Preparation of Product Ethyl-3-(CyPentylSCO-L-ValΨ[COCH$_2$]-L-(p-CF$_3$)Phe-L-Gln)-E-Propenoate.

Ethyl-3-[CyPentylSCO-L-ValΨ[COCH$_2$]-L-(p-CF$_3$)Phe-L-(Tr-Gln)]-E-propenoate (0.148 g, 0.167 mmol, 1 equiv) was dissolved in dry CH$_2$Cl$_2$ (6 mL). Triisopropylsilane (0.103 mL, 0.503 mmol, 3 equiv) and trifluoroacetic acid (3 mL) were added sequentially producing a bright yellow solution. This solution was stirred for 40 minutes and then concentrated. The residue was stirred in Et$_2$O (6 mL), and the solid was collected by filtration, washed with Et$_2$O (2×3 mL), and then dried under vacuum to give ethyl-3-(CyPentylSCO-L-ValΨ[COCH$_2$]-L-(p-CF$_3$)Phe-L-Gln)-E-propenoate (0.089 g, 83%) as a white solid: m;=225° C. (dec); R$_f$=0.44 (10% CH$_3$OH in CH$_2$Cl$_2$); IR (cm$^{-1}$) 3425, 3303, 1717, 1654; $^{-1}$H NMR (DMSO-d$_6$) δ 0.76 (d, 3H, J=6.5), 0.82 (d, 3H, J=6.8), 1.21 (t, 3H, J=7.2), 1.37–1.74 (m, 8H), 1.92–2.13 (m, 5H), 2.50–2.59 (m, 1H), 2.64–2.87 (m, 3H), 2.93–3.04 (m, 1H), 3.46–3.57 (m, 1H), 4.02–4.18 (m, 3H), 4.25–4.36 (m, 1H), 5.51 (dd, 1H, J=15.8, 1.2), 6.62 (dd, 1H, J=15.8, 5.4), 6.74 (s, 1H), 7.16 (s, 1H), 7.37 (d, 2H, J=8.1), 7.59 (d, 2H, J=8.1), 8.06 (d, 1H, J=8.4), 8.28 (d, 1H, J=7.8); Anal. (c$_{31}$H$_{42}$F$_3$N$_3$N$_3$O$_6$S) C, H, N.

EXAMPLE 17

Preparation of Compound 17: [CyPentylSCO-L-ValΨ[COCH$_2$]-L-(p-CH$_3$)Phe-L-Gln]-E-1-Acetyl-3-methylene-pyrrolidin-2-one Preparation of Intermediate [1-(1-Acetyl-2-oxo-pyrrolidin-3-ylidenemethyl)-3-(S)-(trityl-carbamoyl)-propyl]-carbamic Acid tert-Butyl Ester.

Triphenylphosphine (0.646 g, 2.46 mmol, 1.40 equiv) was added to a solution of 1-acetyl-3-bromo-pyrrolidin-2-one (prepared as described in: Ikuta, H., Shirota, H., Kobayashi, S. Yamagishi, Y., Yamada, K., Yamatsu, I., Katayama, K., *J. Med. Chem.* 1987, 30, 1995, which document is entirely incorporated herein by reference) (0.378 g, 1.76 mmol, 1.0 equiv) in THF (10 mL). The reaction mixture was refluxed for 5 h, and then the solvent was evaporated to give the crude salt. This material was dissolved in EtOH (10 mL), and Et$_3$N (0.613 mL, 4.4 mmol, 2.5 equiv) and [BOC-L-(Tr-Gln)]-H (0.932 g, 1.76 mmol, 1 equiv) were added sequentially. The reaction mixture was stirred at 60° C. for 24 h, then the volatiles were evaporated, and the residue was partitioned between CH$_2$Cl$_2$ (50 mL) and brine (50 mL). The organic layer was dried over Na$_2$SO$_4$ and concentrated. The residue was purified by flash chromatography on silica gel (35%

EtOAc in hexanes) to afford [1-(1-acetyl-2-oxo-pyrrolidin-3-(S)-(trityl-carbamoyl)-propyl]-carbamic acid tert-butyl ester as a pale yellow foam (0.381 g, 38%): $R_f$=0.30 (33% EtOAc in hexanes); IR (cm$^{-1}$) 1687, 1510, 1366, 1274; $^1$H NMR (CDCl$_3$) δ 1.42 (s, 9H), 1.80–1.89 (m, 2H), 2.35–2.44 (m, 2H), 2.55 (s, 3H), 2.57–2.64 (m, 1H), 2.77–2.82 (m, 1H), 3.72–3.77 (m, 2H), 4.25 (m, 1H), 4.80 (d, 1H, J=8.1), 6.40–6.44 (m, 1H), 6.82 (s, br, 1H), 7.20–7.33 (m, 15H); Anal. (C$_{35}$H$_{39}$N$_3$O$_5$•1.0H$_2$O) C, H, N.

Preparation of Intermediate [BOC-L-ValΨ[COCH$_2$]-L-(p-CH$_3$)Phe-L-(Tr-Gln)]-E-1-Acetyl-3-methylene-pyrrolidin-2-one.

HCl (5 mL of a 4.0M solution in 1,4-dioxane) was added to a solution of [1-(1-acetyl-2-oxo-pyrrolidin-3-ylidenemethyl)-3-S-(trityl-carbamoyl)-propyl]-carbamic acid tert-butyl ester (0.442 g, 0.760 mmol) in 1,4-dioxane (5 mL). The reaction solution was stirred at 23° C. for 2 hours. It then was concentrated and set aside.

Lithium hydroxide (3.46 mL of a 1M aqueous solution, 3.46 mmol, 5 equiv) was added to a solution of {2-methyl-1S-[4R-(4-methyl-benzyl)-5-oxo-tetrahydrofuran-2S-yl]-propyl}-carbamic acid tert-butyl ester (0.250 g, 0.692 mmol, 1 equiv) in DME (10 mL) at 23° C. The resulting suspension was stirred at 23° C. for 30 min and then partitioned between 10% KHSO$_4$ (20 mL) and CH$_2$Cl$_2$ )3×70 mL). The combined organic layers were dried over Na$_2$SO$_4$, concentrated, and the residue dissolved in CH$_2$Cl$_2$ (12 mL). Powdered 4 Å molecular sieves (0.25 g), 4-methylmorpholine N-oxide (0.162 g, 1.38 mmol, 2 equiv), and tetrapropylammonium perruthenate (0.024 g, 0.068 mmol, 0.10 equiv) were added sequentially. The resulting dark reaction mixture was stirred for 1.5 hours at 23° C. and then vacuum filtered through Whatman #5 paper. The filtrate was added directly to the crude amine salt prepared above. 4-Methylmorpholine (0.304 mL, 2.77 mmol, 4 equiv), 1-hydroxybenzotriazole hydrate (0.140 g, 1.04 mmol, 1.5 equiv), and 1-(3-dimethylaminopropyl)-3-ethylcarbodiimide hydrochloride (0.199 g, 1.04 mmol, 1.5 equiv) were added sequentially, and the reaction mixture was stirred for 19 hours at 23° C. and then loaded directly onto a flash column for chromatographic purification (50% EtOAc in hexanes) providing [BOC-L-ValΨ[COCH$_2$]-L-(p-CH$_2$)Phe-L-(Tr-Gln)]-E-1-acetyl-3-methylene-pyrrolidin-2-one (0.233 g, 40%) as a white foam: $R_f$=0.25 (50% EtOAc in hexanes); IR (cm$^{-1}$) 3336, 1687; $^1$H NMR (CDCl$_3$) δ 0.60 (d, 3H, J=6.8), 0.91 (d, 3H, J=6.8), 1.42 (s, 9H), 1.55–1.68 (m, 2H), 1.82–1.96 (m, 2H), 2.30 (s, 3H), 2.34–2.83 (m, 7H), 2.55 (s, 3H), 2.87–2.98 (m, 1H, 3.64–3.72 (m, 2H), 4.03–4.08 (m, 1H), 4.26–4.38 (m, 1H), 4.78 (d, 1H, J=8.1), 5.79 (d, 1H, J=8.1), 6.10–6.16 (m, 1H), 6.96 (d, 2H, J=7.9), 7.96 (d, 2H, J=7.9), 7.17–7.33 (m, 16H).

Preparation of Intermediate [CyPentylSCO-L-ValΨ[COCH$_2$]-L-(p-CH$_3$)Phe-L-(Tr-Gln)]-E-1-Acetyl-3-methylene-pyrrolidin-2-one.

HCl (3 mL of a 4.0M solution in 1,4-dioxane) was added to a solution of [BOC-L-ValΨ[COCH$_2$]-L-(p-CH$_3$)Phe-L-(Tr-Gln)]-E-1-acetyl-3-methylene-pyrrolidin-2-one (0.217 g, 0.258 mmol) in 1,4-dioxane (3 mL). The reaction solution was stirred at 23° C. for 2 hours and then concentrated. The residue was dissolved in dry CH$_2$Cl$_2$(5 mL). N,N-diisopropylethylamine (0.135 mL, 0.775 mmol, 3 equiv) and cyclopentyl chlorothiolformate (0.072 mL, 1.7 equiv) were added sequentially. The reaction solution was stirred 3 hours at 23° C. and then partitioned between brine (30 mL) and CH$_2$Cl$_2$ (3×30 mL). The combined organic phases were dried over Na$_2$SO$_4$, concentrated, and the residue was chromatographed on silica gel (50% EtOAc in hexanes) to afford [CyPentylSCO-L-ValΨ[COCH$_2$]-L-(p-CH$_3$)Phe-L-(Tr-Gln)]-E-1-acetyl-3-methylene-pyrrolin-2-one (0.114 g, 51%) as a colorless glass: $R_f$=0.26 (50% EtOAc in hexanes); IR (cm$^{-1}$) 3328, 1719, 1670; $^1$H NMR (CDCl$_3$) δ 0.64 (d, 3H, J=6.8), 0.92 (d, 3H, J=6.5), 1.47–1.78 (m, 8H), 1.80–1.95 (m, 2H), 1.99–2.17 (m, 2H), 2.29–2.84 (m, 7H), 2.30 (s, 3H), 2.55 (s, 3H), 2.94 (dd, 1H, J=17.4, 10.0), 3.59–3.73 (m, 3H), 4.25–4.38 (m, 2H), 5.57 (d, 1H, J=8;1), 5.89 (d, 1H, J=8.1), 6.11–6.17 (m, 1H), 6.96 (d, 2H, J=7.9), 7.06 (d, 2H, J=7.9), 7.18–7.33 (m, 16H; Anal. (C$_{52}$H$_{60}$N$_4$O$_6$S) C, H, N.

Preparation of Product [CyPentylSCO-L-ValΨ[COCH$_2$]-L-(p-CH$_3$)Phe-L-Gln]-E-1-Acetyl-3-methylene-pyrrolidin-2-one.

[CyPentylSCO-L-ValΨ[COCH$_2$]-L-(p-CH$_3$)Phe-L-(Tr-Gln)]-E-1-acetyl-3-methylene-pyrrolidin-2-one (0.093 g, 0.107 mmol, 1 equiv) was dissolved in dry CH$_2$Cl$_2$ (6 mL). Triisopropylsilane (0.066 mL, 0.32 mmol, 3 equiv) and trifluoroacetic acid (3 mL) were added sequentially producing a bright yellow solution. This solution was stirred for 40 minutes and then concentrated. The residue was stirred in Et$_2$O (6 mL), and the solid was collected by filtration, washed with Et$_2$O (2×3 mL), and then dried under vacuum to give [CyPentylSCO-L-ValΨ[COCH$_2$]-L-ValΨ[COCH$_2$]-L-(p-CH$_3$)Phe-L-Gln]-E-1-acetyl-3-methylene-pyrrolidin-2-one (0.049 g, 73%) as a white solid: mp=200° C. (dec); $R_f$=0.47 (10% CH$_3$OH in CH$_2$Cl$_2$); IR (cm$^{-1}$) 3425, 3337, 1719, 1670; $^1$H NMR (DMSO-d$_6$) δ 0.74 (d, 3H, J=6.5), 0.81 (d, 3H, J=6.5), 1.36–1.79 (m, 8H), 1.89–2.13 (m, 5H), 2.20 (s, 3H), 2.39–2.90 (m, 7H), 2.43 (s, 3H), 3.46–3.64 (m, 3H), 4.10–4.16 (m, 1H), 4.24–4.36 (m, 1H), 6.12–6.18 (m, 1H), 6.74 (s, 1H), 6.99 (s, 4H), 7.15 (s, 1H), 8.05 (d, 1H, J=7.8), 8.25 (d, 1H, J=7.8); Anal. (C$_{33}$H$_{46}$N$_4$O$_6$S•0.5H$_2$O) C, H, N.

EXAMPLE 18

Preparation of Compound 18: Ethyl-3-(CyPentylSCO-L-PheΨ[COCH$_2$]-L-(p-F)Phe-L-Gln)-E-Propane Preparation of Intermediate 3-(4-Fluoro-phenyl)-propionic Acid cis-1S-Amino-2R-indanol-acetonide Amide.

Oxalyl chloride (6.14 mL, 70.4 mmol, 1.05 equiv) was added to a solution of 3-(4-fluoro-phenyl)-propionic acid (11.3 g, 67.2 mmol, 1 equiv) and N, N-dimethylformamide (0.03 mL, 0.39 mmol, 0.006 equiv) in benzene (150 mL) at 23° C. The reaction mixture was stirred at 23° C. for 1.5 h and then concentrated. The resulting oil was dissolved in THF (30 mL) and was added to a 0° C. solution of (1S, 2R)-cis-1-amino-2-indanol (10.0 g, 67.0 mmol, 1.0 equiv) and Et$_3$N (10.3 mL, 73.9 mmol, 1.1 equiv) in THF (250 mL). After stirring for 20 min at 0° C., the reaction mixture was partitioned between half-saturated NH$_4$Cl (150 mL) and EtOAc (2×250 mL). The organic layers were dried over Na$_2$SO$_4$ and concentrated to afford a white solid. This material was dissolved in a mixture of CH$_2$Cl$_2$ (400 mL) and 2-methoxypropene (30 mL), and the resulting solution was treated with methanesulfonic acid (0.20 mL). After stirring 15 min at 23° C., the reaction mixture was partitioned between half-saturated NaHCO$_3$ (150 mL) and CH$_2$Cl$_2$ (2×150 mL). The combined organic layers were dried over MgSO$_4$ and gravity filtered. The filtrate was concentrated, and the residue was purified by flash column chromatography (gradient elution, 10–20% EtOAc in hexanes) to provide 3-(4-fluoro-phenyl)-propionic acid cis-1S-amino-2R-indanol-acetonide amide (18.2 g, 83%) as a pale yellow oil: $R_f$=0.52 (50% EtOAc in hexanes); IR (cm$^{-1}$) 2934, 1645; $^1$H NMR (CDCl$_3$) δ 1.34 (s, 3H), 1.60 (s, 3H), 2.91–2.95 (m, 2H), 7.02–7.30 (m, 6H); Anal. (C$_{21}$H$_{22}$FNO$_2$) C, H, N.

Preparation of Intermediate {1S-[4R-(4-Fluoro-benzyl)-5-oxo-tetrahydro-furan-2S-yl]-2-phenyl-ethyl}-carbamic Acid tert-Butyl Ester.

n-Butyllithium (13.5 mL of a 1.6M solution in hexanes, 21.6 mmol, 2.0 equiv) was added to a solution of (1R-oxiranyl-2S-phenyl-ethyl)-carbamic acid tert-butyl ester (prepared according to Luly, J. R., Dellaria, J. F. Plattner, J. J., Soderquist, J, L., Yi, N., *J. Org. Chem.* 1987, 52, 1487) (2.85 g, 10.8 mmol, 1 equiv) and 3-(4-fluoro-phenyl)-propionic acid cis-1S-amino-2R-indanol-acetonide amide (3.67 g, 10.8 mmol, 1.0 equiv) in THF (150 mL) at −78° C. The reaction mixture was stirred for 5 min at −78° C., maintained at 0° C. for 1 h, and then partitioned between 0.5M HCl (150 mL) and a 1:1 mixture of EtOAc and hexanes (2×150 mL). The organic layers were dried over $Na_2SO_4$ and concentrated. Flash chromatographic purification of the residue (gradient elution, 25→40% EtOAc in hexanes) gave the coupling product (3.19 g, 49%) as a yellow oil contaminated with several minor impurities. This material was dissolved in a 5:1 mixture of toluene and $CH_2Cl_2$ (180 mL) and treated with p-toluenesulfonic acid monohydrate (1.01 g, 531 mmol, 1.0 equiv) at 23° C. After stirring for 13 h at 23° C., the reaction mixture was filtered through a medium frit, and the filtrate was partitioned between half-saturated $NaHCO_3$ (150 mL) and a 1:1 mixture of EtOAc and hexanes (2×150 mL). The organic layers were dried over $Na_2SO_4$ and concentrated. The residue was purified by flash column chromatography (20% EtOAc in hexanes) to provide {1S-[4R-(4-fluoro-benzyl)-5-oxo-tetrahydro-furan-2S-yl]-2-phenylethyl}-carbamic acid tert-butyl ester (1.28 g, 59%) as a white foam: $R_f$=0.46 (30% EtOAc in hexanes); IR ($cm^{-1}$) 3332, 2976, 1767, 1702; $^1$H NMR ($CDCl_3$) δ 1.36 (s, 9H), 1.88–1.97 (M, 1H), 2.19–2.29 (m, 1H), 2.75–2.99 (m, 4H), 3.05 (dd, 1H, J=13.5, 4.5), 3.93 (q, 2H, J=8.5), 4.13–4.18 (m, 1H), 4.54 (d, 1H, J=9.7), 6.91–6.98 (m, 2H), 7.08–7.32 (m, 7H); Anal. ($C_{24}H_{28}FNO_4$) C, H, N Preparation of Intermediate Ethyl-3-[BOC-L-PheΨ[$COCH_2$]-L-(p-F)Phe-L-(Tr-Gln)]-E-Propenoate.

Lithium hydroxide (7.6 mL of a 1M aqueous solution, 7.6 mmol, 5 equiv) was added to a solution of {1S-[4R-(4-fluoro-benzyl)-5-oxo-tetrahydro-furan-2S-yl]-2-phenyl-ethyl}-carbamic acid tert-butyl ester (0.630 g, 1.52 mmol, 1 equiv) in DME (8 mL) at 23° C. The resulting suspension was stirred at 23° C. for 20 min and then partitioned between 0.5M HCl (100 mL) and EtOAc (2×100 mL). The combined organic layers were dried over $Na_2SO_4$, concentrated, and the residue dissolved in a 1:1 mixture of $CH_2Cl_2$ and $CH_3CN$ (100 mL). 4-Methylmorpholine N-oxide (0.357 g, 3.05 mmol, 2 equiv), powdered 4 Å molecular sieves (0.70 g), and tetrapropylammonium perruthenate (0.054 g, 0.153 mmol, 0.1 equiv) were added sequentially. The resulting dark reaction mixture was stirred for 3 h at 23° C. and then filtered through celite. The filtrate was concentrated under reduced pressure to provide a brown oil which was dissolved in $CH_2Cl_2$ (40 mL). Crude ethyl-3-[$H_2$N-L-(Tr-Gln)]-E-propenoate, 1.27 mmol, 1.2 equiv), 1-hydroxybenzotriazole hydrate (0.268 g, 1.98 mmol, 1.3 equiv), 4-methylmorpholine (0.670 mL, 6.09 mmol, 4equiv), and 1-(3-dimethylaminopropyl)-3-ethylcarbodiimide hydrochloride (0.380 g, 1.98 mmol, 1.3 equiv) were added sequentially, and the reaction mixture was stirred for 22 h at 23° C. and then partitioned between water (150 mL) and a 1:1 mixture of EtOAc and hexanes (2×150 mL). The combined organic layers were dried over $Na_2SO_4$ and concentrated. Purification of the residue by flash column chromatography (40% EtOAc in hexanes) provided ethyl-3-[BOC-L-PheΨ[$COCH_2$]-L-(p-F)Phe-L-(Tr-Gln)-E-propenoate (0.558 g, 43%) as a white solid: mp=89–100° C.; $R_f$=0.44 (50% EtOAc in hexanes); IR ($cm^{-1}$) 3315, 2972, 1708, 1665; $^1$H NMR ($CDCl_3$) δ 1.29 (t, 3H, J=7.2), 1.35 (s. 9H), 1.95–2.05 (m, 1H), 2.34–2.39 (m, 2H), 2.46 (d, 1H, J=16.8), 2.57–2.99 (m, 7H), 4.17 (q, 2H, J=7.2), 4.27–4.33 (m, 1H), 4.48 (s, br, 1H), 4.58 (d, 1H, J=6.9), 5.42 (d, 1H, J=15.3), 6.08 (d, 1H, J=8.4), 6.62 (dd, 1H, J=15.3, 4.8), 6.93–7.19 (m, 6H), 7.21–7.29 (m, 19H); Anal. ($C_{52}H_{56}FN_3O_7$) C, H, N.

Preparation of Intermediate Ethyl-3-[CyPentylSCO-L-PheΨ[$COCH_2$]-L-(p-F)Phe-L-(Tr-Gln)]-E-Propenoate.

HCl (8 mL of a 4.0M solution in 1,4-dioxane) was added to a solution of ethyl-3-[BOC-L-PheΨ[$COCH_2$]-L-(p-F)Phe-L-(Tr-Gln)]-E-propenoate (0.302 g, 0.354 mmol, 1 equiv) in 1,4-dioxane (10 mL). The reaction mixture was stirred at 23° C. for 1.5 h and then concentrated. The resulting oil was dissolved in $CH_2Cl_2$ (15 mL), cooled to 0° C., and 4-methylmorpholine (0.117 mL, 1.06 mmol, 3.0 equiv) and cyclopentyl chlorothiolformate (0.087 mL, 0.528 mmol, 1.5 equiv) were added sequentially. The reaction mixture was stirred for 30 min at 0° C. and then partitioned between water (100 mL) and a 1:1 mixture of EtOAc and hexanes (2×100 mL). The combined organic layers were dried over $Na_2SO_4$, concentrated, and the residue was chromatographed on silica gel (gradient elution, 30–40% EtOAc in hexanes) to afford ethyl-3-[CyPentylSCO-L-PheΨ[$COCH_2$]-L-(p-F)Phe-L-(Tr-Gln)]-E-propenoate (0.163 g, 52%) as a white solid: mp=75–85° C.; $R_f$=0.48 (50% EtOAc in hexanes); IR ($cm^{-1}$) 3314, 1710, 1655; $^1$H NMR ($CDCl_3$) δ 1.29 (t, 3H, J=7.2), 1.48–1.67 (m, 6H), 1.97–2.03 (m, 2H), 2.29–2.42 (m, 2H), 2.54–2.97 (m, 8H), 3.54–3.63 (m, 1H), J=6.9), 5.90 (d, 1H, J=7.2), 4.51–4.58 (m, 2H), 5.44 (dd, 1H, J=15.6, 5.0), 6.91–7.08 (m, 5H), 7.14–7.29 (m, 20H); Anal. ($C_{53}H_{56}RN_3O_6S$) C, H, N.

Preparation of Product Ethyl-3-(CyPentylSCO-L-PheΨ[$COCH_2$]-L-(p-F)Phe-L-Gln)-E-Propenoate.

Triisopropylsilane (0.10 mL) and trifluoroacetic acid (6 mL) were added sequentially to a solution of ethyl-3-[CyPentylSCO-L-PheΨ[$COCH_2$]-L-(p-F)Phe-L-(Tr-Gln)]-E-propenoate (0.160 g, 0.181 mmol) in $CH_2Cl_2$ (10 mL) producing a bright yellow solution. The reaction mixture was stirred for 30 min at 23° C., then carbon tetrachloride (6 mL) was added, and the mixture was concentrated under reduced pressure. The residue was purified by flash column chromatography (5% $CH_3OH$ in $CH_2Cl_2$) to afford ethyl-3-(CyPentylSCO-L-PheΨ[$COCH_2$]-L-(p-F)Phe-L-Gln)-E-propenoate (0.082 g, 71%) as a white solid: mp=210–212° C.; $R_f$=0.10 (10% $CH_3OH$ in $CH_2Cl_2$); IR ($cm^{-1}$) 3284, 1717, 1637; $^1$H NMR (DMSO-$d_6$) δ 1.21 (t, 3H, J=6.8), 1.33–1.72 (m, 8H), 1.90–2.07 (m, 4H), 2.49–3.07 (m, 7H), 3.43–3.47 (m, 1H), 4.09 (q, 2H, J=6.8), 4.33–4.35 (m, 2H), 5.37–5.46 (m, 1H), 6.59–6.67 (m, 1H), 6.77 (s, br, 1H), 7.00–7.28 (m, 9H), 8.04 (d, 1H, J=7.8), 8.46 (d, 1H, J=7.5), 8.53 (d, 1H, J=7.5 ); Anal. ($C_{32}H_{42}FN_3O_6S$) C, H, N.

EXAMPLE 19

Preparation of Compound 19: Ethyl-3-(CyPentyl-L-LeuΨ[$COCH_2$]-L-(p-F)Phe-L-Gln)-E-Propenoate Preparation of Intermediate BOC-L-Leucinol.

To a solution of BOC-Leu-OH (15.09 g, 65 mmol, 1 equiv) in THF (150 mL) at 0° C. was added $BH_3$•THF (163 mL of a 1.0M solution in THF, 163 mmol, 2.51 equiv). The reaction mixture was stirred at 23° C. for 3 h and then cooled to 0° C. Brine (100 mL) was added carefully, and the aqueous layer was extracted with EtOAc (2×100 mL). The combined organic layers were dried over $Na_2SO_4$ and concentrated. The residue was purified by flash column chromatography (gradient elution, 25→35% EtOac in hexanes) to afford BOC-L-Leucinol as a colorless oil (12.59 g, 89%): IR (cm$^{-1}$): 3434, 1699, 1256, 739; $^1$H NMR (CDCl$_3$) δ 0.93 (dd, 6H, J=6.6, 1.5), 1.29–1.31 (m, 2H), 1.45 (s, 9H), 1.60–2.05 (m, 2H), 3.47–3.53 (m, 1H), 3.65–3.72 (m, 2H), 4.56 (s, br, 1H); Anal. (C$_{11}$H$_{23}$NO$_3$) C, H, N.

Preparation of Intermediate BOC-L-Leucinal.

A solution of sulfur trioxide pyridine complex (7.8 g, 49.1 mmol, 3.0 equiv) in a 1:1 mixture of DMSO and CH$_2$Cl$_2$ (100 mL) was added to a solution of BOC-L-Leucinol (3.56 g, 16.4 mmol. 1 equiv) and Et$_3$N (8 mL) in a 1:1 mixture of DMSO and CH$_2$Cl$_2$ (100 mL) at 0° C. The reaction mixture was stirred at 23° C. for 30 min, then poured into ice water (300 mL), and extracted with Et$_2$O (2×200 mL). The combined organic layers were washed with 0.5M HCl (150 mL), half saturated NaHCO$_3$ (150 mL) and H$_2$O (2×150 mL), then dried over Na$_2$SO$_4$, and concentrated to afford crude BOC-L-Leucinal as pale yellow oil (3.48 g, 99%). This material was used without further purification. $^1$H NMR (CDCl$_3$) δ 0.92–0.94 (m, 6H), 1.44 (s, 9H), 1.59–1.64 (m, 1H), 1.67–1.85 (m, 2H), (4.21 (m, 1H), 5.12 (s, br, 1H), 9.57 (s, 1H).

Preparation of Intermediate [1S-Isobutyl-allyl]-carbamic Acid tert-Butyl Ester.

KN(TMS)$_2$ (67.9 mL of a 0.5M solution in toluene, 33.9 mmol, 2.1 equiv) in a 5:1 mixture of THF and DMSO (600 mL) at 0° C. The reaction mixture was stirred at 0° C. for 1 h, then cooled to –78° C., and a solution of BOC-L-Leucinal (3.48 g, 16.2 mmol, 1 equiv) in THF (60 mL) was added. The reaction mixture was stirred at –78° C. for 10 min and then warmed to 23° C. slowly. The mixture was partitioned between 0.5M HCl (200 mL) and a 1:1 mixture of EtOAc in hexanes (2×150 mL). The combined organic layers were washed with H$_2$O (150 mL), dried over Na$_2$SO$_4$, and concentrated. The residue was purified by flash column chromatography (10% EtOAc in hexanes) to afford (1S-isobutyl-allyl)-carbamic acid tert-butyl ester as a pale yellow solid (2.44 g, 70%): R$_f$=0.78 (20% EtOAC in hexanes); IR (cm$^{-1}$): 3343, 2958, 1594, 1520; $^1$H NMR (CDCl$_3$) δ 0.92 (dd, 6H, J=6.6, 2.1), 1.30–1.38 (m, 2H), 1.45 (s, 9H), 1.61–1.74 (m, 1H), 4.13 (m, 1H), 4.38 (s, br, 1H), 4.38 (s, br, 1H), 5.08 (dd, 1H, J=10.2, 1.5), 5.15 (dd, 1H, J=17.4, 1.5), 5.73 (dd, 1H, J=16.8, 10.2); Anal. (C$_{11}$H$_{23}$NO$_2$•H$_2$O) C, H, N.

Preparation of Intermediate [3S-methyl-1R-oxiranyl-butyl]-carbamic Acid tert-Butyl Ester 3-Chloroperoxybenzoic acid (~60%, 8.40 g, ~29.2 mmol, 1.8 equiv) was added to a solution of (1S-isobutyl-ally)-carbamic acid tert-butyl ester (3.48 g, 16.2 mmol, 1 equiv) in CH$_2$Cl$_2$ (100 mL). The reaction mixture was stirred at 23° C. for 6 h, then poured into a 1:1 mixture of EtOAc and hexanes (150 mL), and washed with 10% Na$_2$S$_2$O$_5$ (150 mL) and half-saturated NaHCO$_3$ (150 mL). The organic layer was dried over Na$_2$SO$_4$ and concentrated. The residue was purified by flash column chromatography (10% EtOAc in hexanes) to afford [3S-methyl-1R-oxiranyl-butyl]-carbamic acid tert-butyl ester as a pale yellow oil (3.15 g, 85%): R$_f$=0.55 (20% EtOAc in hexanes); IR (cm$^{-1}$) 1702, 1501, 1366, 1168; $^1$H NMR (CDCl$_3$) δ 0.96 (d, 6H, J=6.9), 1.43 (s, 9H), 1.64–1.81 (m, 1H), 2.60 (s, br, 1H), 2.72–2.76 (m, 2H), 2.84 (m, 1H), 2.99 (s, br, 1H), 3.60 (s, br, 1H), 3.97–3.99 (m, 1H), 4.29 (m, 1H).

Preparation of Intermediate {1S-[4R'-(4-Fluoro-benzyl)-5-oxo-tetrahydrofuran-2S'-yl]-3-methylbutyl}-carbamic Acid tert-Butyl Ester.

n-Butyllithium (8.79 mL of a 1.6M solution in hexanes, 14.06 mmol, 2.0 equiv) was added to a solution of (3S-methyl-1R-oxiranyl-butyl]-carbamic acid tert-butyl ester (1.61 g, 7.03 mmol, 1.0 equiv) and 3-(4-fluoro-phenyl)-propionic acid cis-1S-amino-2R-indanol-acetonide amide (2.39 g, 7.03 mmol, 1 equiv) in THF (100 mL) at –78° C. The resulting yellow solution was stirred at –78° C. for 5 min and then warmed to 0° C. for 1 h. The reaction was quenched with 0.5M HCl (100 mL) and extracted with a 1:1 mixture of EtOAc in hexanes (2×100 mL). The combined organic layers were washed with brine (150 mL), dried over Na$_2$SO$_4$, and concentrated. The residue was purified by flash chromatography on silica gel (20% EtOAc in hexanes) to afford the coupling product as a white foam (2.28 g, 57%): R$_f$=0.44 (25% EtOAc in hexanes); IR (cm$^{-1}$) 3431, 1637, 1510, 1223; $^1$H NMR (CDCl$_3$) δ (mixture of diastereomers) 0.92 (dd, J=6.6, 2.1), 1.26–1.46 (m), 1.60 (s), 1.65 (s), 1.68–1.89 (m), 2.65–2.69 (m), 2.75–2.81 (m), 2.91–2.96 (m), 3.06–3.13 (m), 3.24 (m), 3.34– 3.48 (m), 3.66 (m), 4.60 (d, J=7.5), 4.68–4.71 (m), 4.76–4.78 (m), 4.83 (s, br), 5.06 (d, J=4.8), 6.22 (d, J=7.2), 6.91 –7.31 (m).

To a solution of this material (2.21 g, 3.89 mmol, 1 equiv) in a 5:1 mixture of toluene and CH$_2$Cl$_2$ (120 mL) was added p-toluenesulfonic acid monohydrate (0.739 g, 3.89 mmol, 1.0 equiv) at 23° C. The reaction mixture was stirred at 23° C. for 14 h and then quenched with half-saturated NaHCO$_3$ (100 mL). The resulting mixture was extracted with a 1:1 mixture of EtOAc in hexanes (2×100 mL), and the organic layers were dried over Na$_2$SO$_4$ and concentrated. The residue was purified by chromatography on silica gel (15% EtOAc in hexanes) to afford {1S-[4R'-(4-fluoro-benzyl)-5-oxo-tetrahydrofuran-2S'-yl]-3-methylbutyl}-carbamic acid tert-butyl ester as a white foam (0.426 g, 31%): R$_f$=0.75 (25% EtOAc in hexanes );IR (cm$^{-1}$) 1765, 1702, 1510, 1186; $^1$H NMR (CDCl$_3$) δ 0.89 (d, 3H, J=6.6), 0.91 (d, 3H, J=6.6), 1.23–133 (m, 2H), 1.40 (s, 9H), 145–1.52 (m, 1H), 1.96–2.05 (m, 1H), 2.22–2.32 (m, 1H), 2.77 (dd, 1H, J=13.5, 8.7), 2.87–2.97 (m, 1H), 3.10 (dd, 1H, J=13.5, 4.2), 3.74–3.82 (m, 1H, J=6.9), 4.34 (d, 1H, J=6.9), 6.95–7.01 (m, 2H), 7.11–7.16 (m, 2H); Anal. (C$_{21}$H$_{30}$FNO$_4$) C, H, N.

Preparation of Intermediate Ethyl-3-[BOC-L-LeuΨ [COCH$_2$]-L-(p-F)-Phe-L-(Tr-Gln)]-E-Propenoate.

To a solution of {1S-[4R'-(4-fluoro-benzyl)-5-oxo-tetrahydrofuran-2S'-yl]-3-methylbutyl}-carbamic acid tert-butyl ester (0.40 g, 1.06 mmol, 1 equiv) in 1,2-dimethoxyethane (8 mL) was added LiOH (1.0M solution in H$_2$O, 5.28 mL, 5.28 mmol, 5.0 equiv). The reaction mixture was stirred at 23° C. for 20 min, then quenched with 0.5M HCl (100 mL), and extracted with a 1:1 mixture of EtOAc in hexanes (2×100 mL). The combined organic layers were dried over Na$_2$SO$_4$ and concentrated. The residue was dissolved in a 1:1 mixture of CH$_2$Cl$_2$ and CH$_3$CN (100 mL), and 4 Å molecular sieves (0.70 g), 4-methylmorpholine N-oxide (0.248 g, 2.12 mmol, 2.0 equiv), and tetrapropylammonium perruthenate (0.037 g, 0.106 mmol, 0.1 equiv) were added sequentially. The reaction mixture was stirred at 23° C. for 1 h and filtered through celite. The filtrate was concentrated to give a brown oil which was dissolved in CH$_2$Cl$_2$ (15 mL). Crude ethyl-3-[H$_2$N-L-(Tr-Gln)]-E-propenate•HCl (see preparation of ethyl-3-[CBZ-L-LeuΨ [COCH$_2$]-D/L-Phe-L-(tr-Gln)]-E-propenoate, 1.27 mmol, 1.2 equiv), hydroxybenzotriazole hydrate (0.186 g, 1.38 mmol, 1.3 equiv), 4-methylmorpholine (0.466 mL, 4.24 mmol, 4.0 equiv), and 1-(3-dimethylaminopropyl)-3-ethylcarbodiimide hydrochloride (0.265 g, 1.38 mmol, 1.3 equiv) were added sequentially. The reaction mixture was stirred overnight, then poured into H$_2$O (50 mL), and extracted with CH$_2$Cl$_2$ (2×50 mL). The combined organic layers were dried over Na$_2$SO$_4$ and concentrated. The residue was purified by flash chromatography (40% EtOAc in hexanes) to provide ethyl-3-[BOC-L-LeuΨ[COCH$_2$]-L-(p-F)-Phe-L-(Tr-Gln)]-E-propenoate as a white foam: mp: 174–176° C.; R$_f$=0.56 (50% EtOAc in hexanes); IR (cm$^{-1}$) 1706, 1662, 1509; $^1$H, NMR (CDCl$_3$) (mixture of rotamers) δ 0.87 (dd, J=6.9, 2.4), 1.02–1.12 (m), 1.27 (t, J=7.2), 1.39 (s), 1.96–2.02 (m), 2.37 (t, J=7.2), 2.53 (d, J=12.3), 2.65 (dd, J=12.3, 5.7), 2.76–2.99 (m), 3.62–3.68 (m), 4.17 (q, J=7.2), 4.47 (m), 4.60 (d, J=7.5), 5.39 (dd, J=15.9, 1.5), 5.97 (d, J=8.7), 6.61 (dd, J=15.3, 5.1), 6.96 (t, J=8.4), 7.06–7.16 (m), 7.19–7.30 (m); Anal. (C$_{49}$H$_{58}$FN$_5$O$_7$) C, H, N.

Preparation of Intermediate Ethyl-3-[CyPentylSCO-L-LeuΨ[COCH$_2$]-L-(p-F)Phe-L-(Tr-Gln)]-E-Propenoate.

Ethyl-3-[BOC-L-LeuΨ[COCH$_2$]-L-(p-F-Phe)-L-(Tr-Gln)]-E-propenoate (0.415 g, 0.50 mmol, 1 equiv) was dissolved in 1,4-dioxane (6 mL). A solution of HCl in 1,4-dioxane (4.0M, 6 mL) was added dropwise. The reaction mixture was stirred for 2 h at 23° C., and then the solvent was evaporated to provide the amine salt as a white foam. The crude amine salt was dissolved in dry CH$_2$Cl$_2$ (10 mL) and cooled to 0° C. 4-Methylmorpholine (0.166 mL, 1.51 mmol, 3.0 equiv) and cyclopentyl chlorothiolformate (0.123 mL, 0.75 mmol, 1.5 equiv) were added sequentially. The reaction mixture was stirred at 0° C. for 30 min, poured into H$_2$O (50 mL), and extracted with a 1:1 mixture of EtOAc and hexanes (3×50 mL). The combined organic layers were dried over Na$_2$SO$_4$ and concentrated. The residue was purified by flash chromatography (50% EtOAc in hexanes) to provide ethyl-3-[CyPentylSCO-L-LeuΨ[COCH$_2$]-L-(p-F)Phe-L-(Tr-Gln)]-E-propenoate as a white foam (0.347 g, 83%): R$_f$=0.43 (50% EtOAc in hexanes); IR (cm$^{-1}$) 1716, 1651, 1510; $^1$H NMR (CDCl$_3$) (mixture of rotamer) δ 0.87 (d, J=6.6), 1.06–1.16 (m), 1.29 (t, J=7.2), 1.53–1.60 (m), 1.67–1.69 (m), 2.02–2.06 (m), 2.35 (t, J=7.2), 2.54 (d, J=15.3), 2.63–2.69 (m), 2.78–2.97 (m), 3.57–3.68 (m), 4.17 (q, J=7.2), 4.38–4.49 (m), 4.42 (dd, J=18.0, 14.1), 6.05 (d, J=8.1), 6.62 (dd, J=15.6, 4.8), 6.94–7.00 (m), 7.05–7.12 (m), 7.23–7.31 (m); Anal. (C$_{50}$H$_{58}$FN$_3$O$_6$S) C, H, N.

Preparation of Product Ethyl-3-[CyPentylSCO-L-LeuΨ[COCH$_2$]-L-(p-F)Phe-L-Gln]-E-Propenoate.

Ethyl-3-[CyPentylSCO-L-LeuΨ[COCH$_2$]-L-(p-F)Phe-L-(Tr-Gln)]-E-propenoate (0.285 g) was dissolved in CH$_2$Cl$_2$ (4 mL). Trifluoroacetic acid (4 mL) and triisopropylsilane (0.077 mL) were added sequentially to give a bright yellow solution. After stirring for 30 min, no yellow color remained. The solvents were evaporated to provide a white solid which was triturated with Et$_2$O (8 mL) and filtered to give ethyl-3-[CyPentylSCO-L-LeΨ[COCH$_2$]-L-(p-F)Phe-L-Gln]-E-propenoate as white solid (0.1334 g, 65%): mp 179–180° C.; IR (cm$^{-1}$): 1718, 1656, 1511; $^1$H NMR (DMSO-d$_6$) δ 0.83 (d, 3H, J=6.0), 0.85 (d, 3H, J=6.0), 1.21 (t, 3H, J=7.2), 1.30–1.44 (m, 4H), 1.53–1.70 (m, 7H), 1.97–2.05 (m, 4H), 2.43–2.60 (m, 2H), 2.67–2.80 (m, 2H), 2.92–2.96 (m, 1H), 3.02–3.56 (m, 2H), 4.09 (q, 2H, J=7.2), 4.17–4.19 (m, 1H), 4.31 (m, 1H), 5.42 (d, 1H, J=15.3), 6.62 (dd, 1H, J=15.3, 5.1), 6.75 (s, br, 1H), 7.00–7.06 (m, 2H), 7.14–7.19 (m, 2H), 8.01 (d, 1H, J=8.1), 8.37 (d, 1H, J=7.8); Anal. (C$_{31}$H$_{44}$FN$_3$O$_6$S) C, H, N.

EXAMPLE 20

Preparation of Compound 20: Ethyl-3-(CyPentylOCO-L-ValΨ[COCH$_2$]-L-(p-CH$_3$)Phe-L-Gln)-E-Propenoate Preparation of Intermediate Ethyl-3-[CyPentylOCO-L-ValΨ[COCH$_2$]-L-(p-CH$_3$)Phe-L-(Tr-Gln)]-E-Propenoate.

HCl (3 mL of a 4.0M solution in 1,4-dioxane) was added to a solution of ethyl-3-[BOC-L-ValΨ[COCH$_2$]-L-(p-CH$_3$)Phe-L-(Tr-Gln)]-E-propenoate (0.311 g, 0.388 mmol) in 1,4-dioxane (3 mL). The reaction solution was stirred at 23° C. for 2 hours and then concentrated. The residue was dissolved in dry CH$_2$Cl$_2$ (6 mL). N,N-diisopropylethylamine (0.203 mL, 1.17 mmol, 3 equiv) and cyclopentyl chloroformate (0.098 mL, 1.7 equiv) were added sequentially. The reaction solution was stirred 3 hours at 23° C. and then partitioned between brine (15 mL) and CH$_2$Cl$_2$ (3×30 mL). The combined organic phases were dried over Na$_2$SO$_4$, concentrated, and the residue was chromatographed on silica gel (40% EtOAc in hexanes) to afford ethyl-3-[CyPentylOCO-L-ValΨ[COCH$_2$]-L-(p-CH$_3$)Phe-L-(Tr-Gln)]-E-propenoate (0.189 g, 60%) as a white foam: R$_f$=0.22 (40% EtOAc in hexanes); IR (cm$^{-1}$) 3316, 1712, 1667; $^1$H NMR (CDCl$_3$) δ 0.65 (d, 3H, J=6.8), 0.92 (d, 3H, J=6.8), 1.28 (t, 3H, J=7.2), 1.50–1.87 (m, 10H, 1.91–2.05 (m, 2H), 2.29–2.38 (m, 1H), 2.31 (s, 3H), 2.51 (d, 1H, J=16.8), 2.60–2.69 (m, 1H), 2.72–2.89 (m, 2H), 3.00 (dd, 1H, J=17.3, 9.8), 4.08–4.22 (m, 3H), 4.42–4.53 (m, 1H), 4.88 (d, 1H, J=8.1), 4.95–5.02 (m, 1H), 5.49 (dd, 1H, J=15.8, 1.6), 5.88 (d, 1H, J=8.4), 6.60 (dd, 1H, J=15.8, 5.1), 7.00 (d, 2H, J=7.6), 7.09 (d, 2H, J=7.9), 7.17–7.31 (m, 16H); Anal. (C$_{50}$H$_{59}$N$_3$O$_7$) C, H, N.

EXAMPLE 21

Preparation of Compound 21: Ethyl-3-(CyPentylSCO-L-LeuΨ[COCH$_2$]-L-(p-CH$_3$)Phe-L-Gln)-E-propenoate Preparation of Intermediate {1S-[4R'-(4-Methyl-benzyl)-5-oxo-tetrahydrofuran-2S'-yl]-3-methylbutyl}-carbamic Acid tert-Butyl Ester.

n-Butyllithium (8.43 mL of a 1.6M solution in hexanes, 13.48 mmol, 2.0 equiv) was added to a solution of (3S-methyl-1R-oxiranyl-butyl)-carbamic acid tert-butyl ester (1.55 g, 6.74 mmol, 1.0 equiv) and 3-p-tolyl-propionic acid cis-1S-amino-2R-indanol-acetonide amide (2.39 g, 7.03 mmol, 1 equiv) in THF (100 mL) at −78° C. The resulting yellow solution was stirred at −78° C. for 5 min and then warmed to 0° C. for 1 h. The reaction was quenched with 0.5M HCl (100 mL) was extracted with a 1:1 mixture of EtOAc and hexanes (2×100 mL). The combined organic layers were washed with brine (150 mL), dried over Na$_2$SO$_4$, and concentrated. The residue was purified by chromatography on silica gel (20% EtOAc in hexanes) to afford the coupling product as a white foam (2.07 g, 54%): R$_f$=0.30 (25% EtOAc in hexanes); IR (cm$^{-1}$) 3415, 2955, 1687, 1612, 1355, 1166; $^1$H NMR (CDCl$_3$) (mixture of diastereomers) δ 0.91 (d, J=6.3)1 0.92 (D, J=6.9), 1.34 (s), 1.40 (s), 1.59 (s), 1.65–1.73 (m), 1.82–1.84 (m), 2.31 (s), 2.36 (s), 2.76 (dd, J=12.9, 6.0), 3.06 (s), 3.20 (m), 3.34–3.47 (m), 3.68 (m), 4.58 (d, J=9.3), 4.83 (s, br), 5.66 (m), 6.26 (d, J=7.5), 6.85–6.90 (m), 7.09–7.24 (m).

This material was dissolved in a 5:1 mixture of toluene and CH$_2$Cl$_2$ (120 mL) and was treated with p-toluenesulfonic acid monohydrate (0.697 g, 3.67 mmol, 1.0 equiv). The reaction mixture was stirred at 23° C. for 14 h and then filtered through a medium frit. The clear filtrate was poured into half-saturated NaHCO$_3$ (100 mL) and extracted with a 1:1 mixture of EtOAc in hexanes (2×100 mL). The organic layers were dried over Na$_2$SO$_4$ and concentrated. The residue was purified by flash chromatography on silica gel (10% EtOAc in hexanes) to afford {1S-[4R'-(4-methyl-benzyl)-5-oxo-tetrahydrofuran-2S'-yl]-3-methylbutyl}-carbamic acid tert-butyl ester as a white foam (0.572 g, 32%): IR (cm$^{-1}$) 1765, 1707, 1167; $^1$H NMR (CDCl$_3$) δ 0.89 (d, 3H, J=6.3), 0.90 (d, 3H, J=6.6) 1.19–1.33 (m, 2H), 1.42 (s, 9H), 1.43–1.54 (m, 1H), 1.96–2.06 (m, 1H), 2.18–2.27 (m, 1H), 2.32 (s, 3H), 2.75 (dd, 1H, J=13.5, 9.0), 2.88–2.98 (m, 1H), 3.10 (dd, 1H, J=13.5, 4.2), 3.72–3.80 (m, 1H), 4.24 (t, 1H, J=6.3), 4.34 (d, 1H, J=9.9), 7.04–7.12 (m, 4H); Anal. ($C_{22}H_{33}NO_4$) C, H, N.

Preparation of Intermediate Ethyl-3-[BOC-L-LeuΨ[$COCH_2$]-L-(p-$CH_3$)Phe-L-(Tr-Gln)]-E-Propenoate.

This material was prepared from {1S-[4R'-(4-methylbenzyl)-5-oxo-tetrahydrofuran-2S'-yl]-3-methylbutyl}-carbamic acid tert-butyl ester (0.572 g, 1.52 mmol) as described previously for the formation of ethyl-3-[BOC-L-LeuΨ[$COCH_2$]-L-(p-F)-Phe-L-(Tr-Gln)]-E-propenoate (Example 19) to give ethyl-3-[BOC-L-LeuΨ[$COCH_2$]-L-(p-$CH_3$)Phe-L-(Tr-Gln)]-E-propenoate as a white foam (0.785 g, 63%): $R_f$=0.70 (50% EtOAc in hexanes); IR ($cm^{-1}$) 1709, 1664, 1170; $^1$H NMR ($CDCl_3$) (mixture of rotamer) δ 0.85 (d, J=6.3), 0.98–1.08 (m), 1.28 (t, J=7.2), 1.39 (s), 1.52–1.62 (m), 1.97–2.05 (m), 2.31 (s), 2.36 (t, J=6.9), 2.52 (d, J=16.5), 2.64–2.67 (m), 2.83-1.97 (m), 4.17 (q, J=7.2), 4.48 (m), 4.58 (d, J=7.2), 5.35 (dd, J=15.9, 1.5), 5.87 (d, J=8.4), 6.61 (dd, J=15.9, 5.1), 7.02–7.11 (m), 7.20–7.30 (m); Anal. ($C_{50}H_{61}N_3O_7$•0.1$H_2O$) C, H, N.

Preparation of Intermediate Ethyl-3-[CyPentylSCO-L-LeuΨ[$COCH_2$]-L-(p-$CH_3$)Phe-L-(Tr-Gln)]-E-Propenoate.

Ethyl-3-[BOC-L-LeuΨ[$COCH_2$]-L-(p-$CH_3$)Phe-L-(Tr-Gln)]-E-propenoate (0.523 g, 0.64 mmol) was deprotected and coupled with cyclopentyl chlorothiolformate (0.158 mL, 0.96 mmol) as described previously for the formation of ethyl-3-[CyPentylSCO-L-LeuΨ[$COCH_2$]-L-(p-F)Phe-L-(Tr-Gln)-E-propenoate (Example 19) to give ethyl-3-[CyPentylSCO-L-LeuΨ[$COCH_2$]-L-(p-$CH_3$)Phe-L-(Tr-Gln)-E-propenoate as a white foam (0.301 g, 56%): IR ($cm^{-1}$) 1716, 1651, 1518; $^1$H NMR ($CDCl_3$) (mixture of rotamers) δ 0.85 (d, J=6.3), 1.02–1.12 (m), 1.29 (t, J=7.2), 1.52–1.62 (m), 1.67–1.68 (m), 1.98–2.10 (m), 2.31–2.36 (m), 2.53 (d, J=15.9), 2.63–2.68 (m), 2.76–2.95 (m), 3.57–3.66 (m), 4.16 (q, J=7.2), 4.38 (m), 4.48–4.52 (m), 5.35 (d, J=7.5), 5.53 (dd, J=15.9, 1.5), 5.94 (d, J=8.2), 6.62 (dd, J=15.9, 4.8), 6.99–7.12 (m), 7.21–7.31 (m); Anal. ($C_{51}H_{61}N_3O_6S$•0.25$H_2O$) C, H, N.

Preparation of Product Ethyl-3-[CyPentylSCO-L-LeuΨ[$COCH_2$]-L-(p-$CH_3$)Phe-L-Gln]-E-Propenoate.

Ethyl-3-[CyPentylSCO-L-LeuΨ[$COCH_2$]-L-(p-$CH_3$)Phe-L-(Tr-Gln)-E-propenoate (0.272 g, 0.32 mmol) was deprotected using the procedure described for the formation of ethyl-3-[CyPentylSCO-L-LeuΨ[$COCH_2$]-L-(p-F)Phe-L-Gln]-E-propenoate (Example 19) to give ethyl-3-[CyPentylSCO-L-LeΨ[$COCH_2$]-L-(p-$CH_3$)Phe-L-Gln]-E-propenoate as white solid (0.106 g, 55%): mp 173–174° C.; IR ($cm^{-1}$) 1719, 1655, 1522, 1198; $^1$H NMR (DMSO-$d_6$) δ 0.83 (d, 3H, J=6.0), 0.85 (d, 3H, J=6.0), 1.21 (t, 3H, J=7.2), 1.30–1.44 (m, 4H), 1.53–1.70 (m, 7H), 1.97–2.05 (m, 4H), 2.43–2.60 (m, 2H), 2.67–2.80 (m, 2H), 2.92–2.96 (m, 1H), 3.02–3.56 (m, 2H), 4.09 (q, 2H, J=7.2), 4.17–4.19 (m, 1H), 4.31 (m, 1H), 5.42 (d, 1H, J=15.3), 6.62 (dd, 1H, J=15.3, 5.1), 6.75 (s, br, 1H), 7.00–7.06 (m, 2H), 7.14–7.19 (m, 2H), 8.01 (d, 1H, J=8.1), 8.37 (d, 1H, J=7.8); Anal. ($C_{31}H_{44}FN_3O_6S$) C, H, N.

EXAMPLE 22

Preparation of Compound 22: Ethyl-3-(CyPentylSCO-L-tert-LeuΨ[$COCH_2$]-L-Gln)-E-Propenoate Preparation of Intermediate CBZ-L-tert-Leucine.

To a solution of L-tert-leucine (5.12 g, 39 mmol, 1 equiv) in 1,4-dioxane (80 mL) and 1M NaOH (39 mL, 39 mmol, 1.0 equiv) at 0° C. was added benzyl chloroformate (6.24 mL, 43.68 mmol, 1.12 equiv). The reaction mixture was stirred at 23° C. overnight, then concentrated, poured into 1M HCl (80 mL), and extracted with $CH_2Cl_2$ (2×100 mL). The organic layers were dried over $Na_2SO_4$ and concentrated to give crude CBZ-L-tert-leucine (20.7 g) as a clear oil: IR ($cm^{-1}$) 3336, 1715, 1521, 1232; $^1$H NMR ($CDCl_3$) δ 1.02 (s, 9H), 4.21 (d, 1H, J=9.9), 5.11 (s, 2H), 5.35 (d, 1H, J=9.0), 7.34–7.37 (m, 5H).

Preparation of Intermediate 4-Benzyloxycarbonylamino-5,5-dimethyl-3-oxo-hexanoic Acid tert-Butyl Ester.

To a solution of CBZ-L-tert-leucine (20.53 g, 77.4 mmol, 1 equiv) in THF (150 mL) was added 1,1'-carbonyldiimidazole (13.81 g, 85.14 mmol, 1.1 equiv) at 23° C. The resulting solution was stirred at 23° C. for 1 h. In a separate flask, n-butyllithium (101.59 mL of a 1.6 M solution in hexanes, 162.54 mmol, 2.1 equiv) was added to a solution of diisopropylamine (22.78 mL, 162.54 mmol, 2.1 equiv) in THF (100 mL) at –78° C. The reaction mixture was stirred for 15 min at –78° C., warmed to 0° C. for 5 min, then cooled back to –78° C. A solution of tert-butyl acetate (21.9 mL, 162.54 mmol, 2.1 equiv) in THF (10 mL) was added via cannula, and the resulting mixture was stirred at –78° C. for 10 min. The above imidazole solution was then added dropwise to the lithium enolate at –78° C. The resulting mixture was stirred at –78° C. for 1 h, quenched with 1 M HCl (100 mL), and extracted with EtOAc (2×100 mL). The combined organic layers were washed with brine (150 mL), fried over $Na_2SO_4$, and concentrated. The residue was purified by flash chromatography on silica gel (10% EtOAc in hexanes) to afford 4-benzyloxycarbonylamino-5,5-dimethyl-3-oxo hexanoic acid tert-butyl ester as a pale yellow oil (12.06 g, 44%): IR ($cm^{-1}$) 1717, 1508, 1265, 739; $^1$H NMR ($CDCl_3$) δ 1.09 (s, 9H), 3.50 (s, 2H), 4.29 (d, 1H, J=9.3), 5.03 (s, 2H), 5.35–5.42 (m, 1H), 7.34 (s, 5H).

Preparation of Intermediate CBZ-L-tert-LeuΨ[$COCH_2$]-L-Phe-OMe.

To a stirred solution of (R)-2-hydroxy-3-phenyl-propionic acid methyl ester (2.53 g, 14.06 mmol, 3.1 equiv) in $CH_2Cl_2$ (30 mL) at 0° C. was added trifluoromethanesulfonic anhydride (2.50 mL, 14.8 mmol, 3.3 equiv) and 2,6-lutidine (1.72 mL, 14.8 mmol, 3.3 equiv) slowly. The resulting pink solution was stirred at 0° C. for 30 min, then poured into 0.5 M HCl (100 mL), and extracted with a 1:1 mixture of EtOAc in hexanes (2×100 mL). The combined organic layers were dried over $Na_2SO_4$, concentrated, and utilized in the next step below.

A solution of 4-benzyloxycarbonylamino-5,5-dimethyl-3-oxo-hexanoic acid tert-butyl ester (1.64 g, 4.51 mmol, 1 equiv) in THF (100 mL) was added dropwise to a stirred suspension of NaH (0.190 g of a 60% dispersion in mineral oil, 4.74 mmol, 1.05 equiv) in THF (100 mL) at 0° C. After stirring for 10 min, a solution of crude (R)-2-triflyoxy-3-phenyl-propionic acid methyl ester (prepared above) in $CH_2Cl_2$ (10 mL) was added dropwise. The resulting mixture was stirred at 23° C. for 24 h, then quenched with 1 M HCl (50 mL), and extracted with EtOAc (3×50 mL). The combined organic layers were washed with brine (100 mL), dried over $Na_2SO_4$, and concentrated to provide a pale yellow oil. Without further purification, the above oil was dissolved in $CH_2Cl_2$ (10 mL), treated with trifluoroacetic acid (2 mL), and then maintained at 23° C. for 24 h. After dilution with $CH_2Cl_2$ (50 mL), the resulting solution was washed with saturated $NaHCO_3$ (50 mL) and brine (50 mL). The organic layer was dried over $Na_2SO_4$ and concentrated. The residue was purified by flash chromatography on silica gel (10% EtOAc in hexanes) to afford CBZ-L-tert-LeuΨ[$COCH_2$]-L-Phe-OMe as a pale yellow oil (1.01 g, 54%): $R_f$=0.41 (25% EtOAc in hexanes); IR ($cm^{-1}$) 1711, 1514, 1233; $^1$H NMR (CDCl$_3$) δ 0.97 (s, 9H), 2.58–2.76 (m, 2H), 2.96–3.17 (m, 3H), 3.62 (s, 3H) 4.17 (d, 1H, J=8.1), 5.06–5.10 (s, 2H), 5.32 (d, 1H, J=8.6), 7.12–7.36 (m, 10H); Anal. (C$_{25}$H$_{31}$NO$_5$●0.25 H$_2$O) C, H, N.

BOC-L-tert-LeuΨ[COCH$_2$]-L-Phe-OMe.

10% Pd on C (0.110 g) was added to a solution of CBZ-L-tert-LeuΨ[COCH$_2$]-L-Phe-OMe (0.513 g, 1.33 mmol, 1 equiv) and di-tert-butyl dicarbonate (0.378 g, 1.73 mmol, 1.3 equiv) in CH$_3$OH at 23° C. The reaction mixture was stirred at 23° C. under an H$_2$ atmosphere (balloon) overnight. The mixture was filtered through celite, and the filtrate was concentrated. The residue was purified by flash chromatography on silica gel (10% EtOAc in hexanes) to afford BOC-L-tert-LeuΨ[COCH$_2$]-L-Phe-OMe as white solid (0.366 g, 70%): mp=98–99° C.; R$_f$=0.54 (25% EtOAc in hexanes); IR (cm$^{-1}$) 1707, 1497, 1367, 1236, 1168; $^1$H NMR (CDCl$_3$) δ 0.97 (s, 9H), 2.60–2.78 (m, 2H), 2.95–3.19 (m, 3H), 3.63 (s, 3H), 4.07–4.11 (m, 2H), 5.07 (d, 1H, J=9.3), 7.13–7.32 (m 5H); Anal. (C$_{25}$H$_{31}$NO$_5$) C, H, N.

Preparation of Intermediate CBZ-L-tert-LeuΨ[COCH$_2$]-L-Phe-OH.

2 M NaOH (3.35 mL, 6.7 mmol, 8.0 equiv) was added to a solution of BOC-L-tert-LeuΨ[COCH$_2$]-L-Phe-OMe (0.328 g, 0.84 mmol, 1 equiv) in CH$_3$OH (6 mL) at 0° C. over 10 min. The reaction mixture was stirred at 0° C. for 2 h, then poured into 10% KHSO$_4$ (80 mL), and extracted with CH$_2$Cl$_2$ (2×100 mL). The organic layers were dried over Na$_2$SO$_4$ and concentrated to give BOC-L-tert-LeuΨ[COCH$_2$]-L-Phe-OH as a white solid (0.315 g, 99%) which was used without further purification: IR (cm$^{-1}$) 2960, 1710, 1498, 1368, 1167; $^1$H NMR (CDCl$_3$) δ 0.94 (s, 9H), 1.39 (s, 9H), 2.60–2.80 (m, 2H), 2.95–3.16 (m, 3H), 4.08 (d, 2H, J=9.3), 5.09 (d, 1H, J=9.6), 7.12–7.31 (m 5H).

Preparation of Intermediate Ethyl-3-[BOC-L-tert-LeuΨ[COCH$_2$]-L-Phe-L-(Tr-Gln)]-E-Propenoate.

Ethyl-3-[BOC-L-(Tr-Gln)]-E-propenoate (0.523 g, 0.64 mmol) was deprotected and coupled with BOC-L-tert-LeuΨ[COCH$_2$]-L-Phe-OH (0.318 g, 0.84 mmol) as described for the formation of ethyl-3-[BOC-L-LeuΨ[COCH$_2$]-L-(p-F)Phe-L-(Tr-Gln)]-E-propenoate (Example 19) to give ethyl-3-[BOC-L-tert-LeuΨ[COCH$_2$]-L-Phe-L-(Tr-Gln)]-E-propenoate as a white foam (0.474 g, 70%): R$_f$=0.58 (50% EtOAc in hexanes); IR (cm$^{-1}$) 1702, 1669, 1494, 1169; $^1$H NMR (CDCl$_3$) (mixture of rotamers) δ 0.85 (s), 1.30 (t, J=7.2), 1.41 (s), 156–165 (m), 1.95–2.02 (m), 2.22–2.42 (m), 2.62–2.88 (m), 3.09–3.18 (m), 4.00 (d, J=8.7), 4.17 (t, J=7.2), 4.46–4.51 (m), 4.93 (d, J=8.7), 5.37 (d, J=15.9), 5.69 (d, J=9.3), 6.54 (dd, J=15.9, 4.8), 7.19-7.15 (m), 7.18–7.31 (m); Anal. (C$_{49}$H$_{59}$N$_3$O$_7$) C, H, N.

Preparation of Intermediate Ethyl-3-[CyPentylSCO-L-tert-LeuΨ[COCH$_2$]-L-Phe-L-(Tr-Gln)]-E-Propenoate.

Ethyl-3-[BOC-L-tert-LeuΨ[COCH$_2$]-L-Phe-L-(Tr-Gln)]-E-propenoate (0.441 g, 0.55 mmol) was deprotected and coupled with cyclopentyl chlorothiolformate (0.135 mL, 0.82 mmol) as described previously for the formation of ethyl-3-[CyPentylSCO-L-LeuΨ[COCH$_2$]-L-(p-F)Phe-L-(Tr-Gln)]-E-propenoate (Example 19) to give ethyl-3-[CyPentylSCO-L-tert-LeuΨ[COCH$_2$]-L-Phe-L-(Tr-Gln)]-E-propenoate as a white foam (0.347 g, 76%): IR (cm$^{-1}$) 1718, 1656, 1493, 1186; $^1$H NMR (CDCl$_3$) (mixture of rotamers) δ 0.86 (s), 1.27 (t, J=7.2), 1.56–1.68 (m), 1.95–2.2 (m), 2.22–2.39 (m), 2.60–2.74 (m), 2.84–2.90 (m), 3.05–3.14 (m), 3.59–3.64 (m), 4.16 (q, J=7.2), 4.31 (d, J=8.4), 4.48 (m), 5.41 (dd, J=15.9, 1.8), 5.67 (d, J=8.7), 5.82 (d, J=9.0), 6.56 (dd, J=15.6, 5.1), 7.19–7.31 (m); Anal. (C$_{50}$H$_{59}$N$_3$O$_6$) C, H, N.

Preparation of Product Ethyl-3-(CyPentylSCO-L-tert-LeuΨ[COCH$_2$]-L-Phe-L-Gln)-E-Propenoate.

Ethyl-3-[CyPentylSCO-L-tert-LeuΨ[COCH$_2$]-L-Phe-L-(Tr-Gln)]-E-propenoate (0.318 g, 0.38 mmol) was deprotected using the procedure described for the formation of ethyl-3-(CyPentylSCO-L-LeuΨ[COCH$_2$]-L-(p-F)Phe-L-Gln)-E-propenoate (Example 19) to give ethyl-3-[CyPentylSCO-L-tert-LeuΨ[COCH$_2$]-L-Phe-L-Gln]-E-propenoate as white solid (0.204 g, 91%): mp 65–68° C.; IR (cm$^{-1}$) 1715, 1652, 1520, 1193; $^1$H NMR (CDCl$_3$) (mixture of rotamers) δ 0.96 (s), 1.31 (t, J=7.2), 1.50–1.73 (m), 1.96–2.13 (m), 2.23 (t, J=7.5), 2.68–2.79 (m), 2.84–2.95 (m), 3.11–3.21 (m), 3.59–3.69 (m), 4.18 (q, J=7.2), 4.36 (d, J=8.1), 4.52–4.59 (m), 5.37 (s, br), 5.42 (dd, 1H, J=15.9, 1.5), 5.80 (d, J=9.0), 5.90 (d, J=8.4), 6.46 (s, br), 6.61 (dd, 1H, J=15.9, 5.1), 7.17–7.30 (m); Anal. (C$_{31}$H$_{45}$N$_3$O$_6$S) C, H, N.

Preparation of Product Ethyl-3-(CyPentylSCO-L-ValΨ[COCH$_2$]-L-(p-CH$_3$)Phe-L-Gln)-E-Propenoate.

Ethyl-3-[CyPentylOCO-L-ValΨ[COCH$_2$]-L-(p-CH$_3$)Phe-L-(Tr-Gln)]-E-propenoate (0.160 g, 0.197 mmol, 1 equiv) was dissolved in dry CH$_2$Cl$_2$ (8 mL). Triisopropylsilane (0.121 mL, 0.591 mmol, 3 equiv) and trifluoroacetic acid (4 mL) were added sequentially producing a bright yellow solution. This solution was stirred for 40 minutes and then concentrated. The residue was stirred in Et$_2$O (8 mL), and the solid was collected by filtration, washed with Et$_2$O (2×4 mL), and then dried under vacuum to give ethyl-3-(CyPentylOCO-L-ValΨ[COCH$_2$]-L-(p-CH$_3$)Phe-L-Gln)-E-propenoate (0.094 g, 84%) as a white solid: mp=206–207° C. (dec); R$_f$=0.38 (10% CH$_3$OH in CH$_2$Cl$_2$); IR (cm$^{-1}$) 3413, 3307, 3213, 1708, 1660; $^1$H NMR (DMSO-d$_6$) δ 0.72 (d, 3H, J=6.8), 0.81 (d, 3H, J=6.5), 120 (t, 3H, J=7.0), 1.46–1.82 (m, 10H), 1.97–2.10 (m, 3H), 2.23 (s, 3H), 2.38–2.54 (m, 1H), 2.65–2.84 (m, 2H), 2.86–2.97 (m, 1H), 3.81–3.88 (m, 1H), 4.03–4.18 (m, 2H), 4.26–4.38 (m, 1H), 4.85–4.94 (m, 1H), 5.55 (d, 1H, J=15.9), 6.65 (dd, 1H, J=15.9, 5.3), 6.73 (s, 1H), 7.03 (s, 4H), 7.14 (s, 1H), 7.27 (d, 1H, J=8.1), 8.02 (d, 1H, J=8.4); Anal. (C$_{31}$H$_{45}$N$_3$O$_7$) C, H, N.

EXAMPLE 23

Preparation of Compound 23: Ethyl-3-(CyPentylCH$_2$CO-L-ValΨ[COCH$_2$]-L-(p-CH$_3$)Phe-L-Gln)-E-Propenoate Preparation of Intermediate Ethyl-3-[CyPentylCH$_2$CO-L-ValΨ[COCH$_2$]-L-(p-CH$_3$)Phe-L-(Tr-Gln)]-E-Propenoate.

HCl (3 mL of a 4.0 M solution in 1,4-dioxane) was added to a solution of ethyl-3-[BOC-L-ValΨ[COCH$_2$]-L-(p-CH$_3$)Phe-L-(Tr-Gln)]-E-propenoate (0.315 g, 0.393 mmol, 1 equiv) in 1,4-dioxane (3 mL). The reaction solution was stirred at 23° C. for 1.67 hours and then was concentrated to provide crude ethyl-3-[H$_2$N-L-ValΨ[COCH$_2$]-L-(p-CH$_3$)Phe-L-(Tr-Gln)]-E-propenoate●HCl which was set aside.

Dicyclohexylcarbodiimide (0.162 g, 0.785 mmol, 2 equiv) was added to a solution of cyclopentyl acetic acid (0.197 mL, 1.57 mmol, 4 equiv) in Et$_2$O (10 mL). The reaction mixture was stirred for 1.5 hours, and then the white precipitate was removed by filtration. The filtrate was concentrated, then dissolved in dry CH$_2$Cl$_2$ (5 mL), and added to a solution of crude ethyl-3-[H$_2$N-L-ValΨ[COCH$_2$]-L-(p-CH$_3$)Phe-L-(Tr-Gln)]-E-propenoate●HCl (from above) and 4-methylmorpholine (0.086 mL, 0.782 mmol, 2 equiv) in dry CH$_2$Cl$_2$ (3 mL). The reaction mixture was stirred for 2.5 hours and concentrated. The residue was chromatographed on silica gel (gradient elution 40–50% EtOAc in hexanes) to afford ethyl-3-[CyPentylCH$_2$CO-L-ValΨ[COCH$_2$]-L-(p-CH$_3$)Phe-L-(Tr-Gln)]-E-propenoate (0.202 g, 63%) as a white foam: R$_f$=0.65 (10% CH$_3$OH in CHCl$_3$); IR (cm$^{-1}$) 3296, 1716, 1650; $^1$H NMR (CDCl$_3$) δ 0.71 (d, 3H, J=6.8), 0.92 (d, 3H, J=6.8), 1.02–1.16 (m, 2H), 1.29 (t, 3H, J=7.2), 1.47–1.82 (m, 8H), 1.89–2.16 (m, 5H), 2.30–2.36 (m, 1H), 2.31 (s, 3H), 2.46–2.69 (m, 2H), 2.74–2.89 (m, 2H), 2.95–3.08 (m, 1H), 4.12–4.22 (m, 2H), 4.41–4.53 (m, 2H), 5.52 (dd, 1H, J=15.6, 1.6) 5.73 (d, 1H, J=8.1), 6.00 (d, 1H, J=8.1), 6.61 (dd, 1H, J=15.6, 5.1), 6.99 (d, 2H, J=7.9), 7.08 (d, 2H, J=7.9), 7.17–7.30 (m, 16H); Anal (C$_{51}$H$_{61}$N$_3$O$_6$●0.5 H$_2$O) C, H, N.

Preparation of Product Ethyl-3-(CyPentylCH$_2$CO-L-ValΨ[COCH$_2$]-L-(p-CH$_3$)Phe-L-Gln)-E-Propenoate.

Ethyl-3-[CyPentylCH$_2$CO-L-ValΨ[COCH$_2$]-L-(p-CH$_3$)Phe-L-(Tr-Gln)]-E-propenoate (0.167 g, 0.206 mmol, 1 equiv) was dissolved in dry CH$_2$Cl$_2$ (8 mL). Triisopropylsilane (0.126 mL, 0.615 mmol, 3 equiv) and trifluoroacetic acid (4 mL) were added sequentially producing a bright yellow solution. This solution was stirred for 40 minutes and then concentrated. The residue was stirred in Et$_2$O (8 mL), and the solid was collected by filtration, washed with Et$_2$O (2×4 mL), and then dried under vacuum to give ethyl-3-(CyPentylCH$_2$CO-L-ValΨ[COCH$_2$]-L-(p-CH$_3$)Phe-L-Gln)-E-propenoate (0.092 g, 79%) as a white solid: mp=253–255° C. (dec); R$_f$=0.42 (10% CH$_3$OH in CHCl$_3$); IR (cm$^{-1}$) 3401, 3284, 1713, 1649; $^1$H NMR (DMSO-d$_6$) δ 0.74 (d, 3H, J=6.8), 0.81 (d, 3H, J=6.5), 1.03–1.19 (m, 2H), 1.20 (t, 3H, J=7.0), 1.40–1.75 (m, 9H), 2.00–2.15 (m, 6H), 2.23 (s, 3H), 2.42 (dd, 1H, J=18.4, 4.7), 2.66–2.84 (m, 2H), 2.86–2.96 (m, 1H), 4.06–4.17 (m, 3H), 4.27–4.37 (m, 1H), 5.57 (dd, 1H, J=15.7, 1.4), 6.66 (dd, 1H, J=15.7, 5.4), 6.73 (s, 1H), 7.03 (s, 4H), 7.16 (s, 1H), 7.92 (d, 1H, J=8.1), 8.01 (d, 1H, J=7.8); Anal (C$_{32}$H$_{47}$N$_3$O$_6$C, H, N.

EXAMPLE 24

Preparation of Compound 24: Ethyl-3-(CyPentylSCO-L-CyhexΨ[COCH$_2$]-L-(p-F)Phe-L-Gln)-E-Propenoate.

Preparation of Intermediate trans-5-Cyclohexyl-pent-4-enoic Acid.

A solution of cyclohexane carboxaldehyde (11.22 g, 100 mmol, 1 equiv) in THF (100 mL) was added dropwise via addition funnel to a solution of vinylmagnesium bromide (100 mL of a 1.0 M solution in THF, 100 mmol, 1.0 equiv) in Et$_2$O (100 mL) at 0° C. After the addition was completed, the reaction mixture was stirred for 1 h at 0° C. and then partitioned between 0.5 M HCl (150 mL) and a 1:1 mixture of EtOAc and hexanes (2×150 mL). The combined organic layers were dried over Na$_2$SO$_4$ and concentrated to afford a yellow oil. This material was combined (neat) with diethyl malonate (16.7 mL, 110 mmol, 1.1 equiv) and Ti(OEt)$_4$ (2.10 mL, 10.0 mmol, 0.10 equiv) and was heated to 160° C. for 1 h (distilling out EtOH as it was formed). The reaction mixture was then maintained at 190° C. for 4 h and then cooled to 60° C. EtOH (50 mL) and 6.0 M KOH (50 mL) were added sequentially, and the brown reaction mixture was refluxed for 3 h. After cooling to 23° C., the reaction mixture was filtered through a medium frit, and the filtrate was partitioned between water (150 mL) and Et$_2$O (2×100 mL). The aqueous layer was then acidified to pH=2 (as indicated by pH paper) with concentrated HCl and extracted with a 1:1 mixture of EtOAc and hexanes (2×150 mL). The combined organic layers were dried over Na$_2$SO$_4$, concentrated, and the residue was distilled at reduced pressure to afford trans-5-cyclohexyl-pent-4-enoic acid (5.68 g, 31%) as a colorless liquid: bp: 150–156° C. (1 torr); IR (cm$^{-1}$) 3001 (br), 2923, 1711; $^1$H NMR (CDCl$_3$) δ 0.96–1.32 (m, 5H), 1.60–1.76 (m, 5H), 1.85–1.94 (m, 1H), 2.27–2.44 (m, 4H), 5.31–5.48 (m, 2H); Anal. (C$_{11}$H$_{18}$O$_2$) C, H.

Preparation of Intermediate trans-5-Cyclohexyl-pent-4-enoic Acid (2R-Hydroxy-1R-methyl-2-phenyl-ethyl)-methyl Amide.

Oxalyl chloride (2.81 mL, 32.2 mmol, 1.05 equiv) was added to a solution of trans-5-cyclohexyl-pent-4-enoic acid (5.60 g, 30.7 mmol, 1 equiv) and N,N-dimethylformamide (0.03 mL, 0.39 mmol, 0.013 equiv) in benzene (100 mL) at 23° C. The reaction mixture was stirred at 23° C. for 2 h and then concentrated under reduced pressure. The resulting oil was dissolved in THF (20 mL) and added via cannula to a solution of (1R,2R)-(−)-pseudoephedrine (4.61 g, 27.9 mmol, 0.91 equiv) and triethylamine (5.06 mL, 36.3 mmol, 1.1 equiv) in THF (300 mL) at 0° C. The reaction mixture was stirred at 0° C. for 30 min and then partitioned between half-saturated NH$_4$Cl (150 mL) and a 1:1 mixture of EtOAc and hexanes (2×150 mL). The combined organic layers were dried over Na$_2$SO$_4$, concentrated, and the residue purified by flash column chromatography (50% EtOAc in hexanes) to afford trans-5-cyclohexyl-pent-4-enoic acid (2R-hydroxy-1R-methyl-2-phenyl-ethyl)-methyl amide (5.21 g, 57%) as a white solid: mp=89–91° C.; R$_f$=0.33 (50% EtOAc in hexanes); IR (cm$^{-1}$) 3380, 1621; $^1$H NMR (CDCl$_3$, mixture of rotamers) δ 0.97–1.32 (m), 1.54–1.74 (m), 1.86–1.93 (m), 2.24–2.58 (m), 2.81 (s), 2.91 (s), 3.98–4.06 (m), 4.35–4.48 (m), 4.55–4.61 (m), 5.32–5.47 (m), 7.24–7.41 (m); Anal. (C$_{21}$H$_{31}$NO$_2$) C, H, N.

Preparation of Intermediate trans-5-Cyclohexyl-2S-(4-fluoro-benzyl)-pent-4-enoic Acid (2R-Hydroxy-1R-methyl-2-phenyl-ethyl)-methyl Amide.

n-Butyllithium (20.7 mL of a 1.6 M solution in hexanes, 33.1 mmol, 2.1 equiv) was added to a suspension of anhydrous lithium chloride (4.68 g, 110 mmol, 7 equiv) and diisopropylamine (4.98 mL, 35.3 mmol, 2.25 equiv) in THF (300 mL) at −78° C. The reaction mixture was stirred for 20 min at −78° C., then maintained at 0° C. for 5 min, and subsequently cooled again to −78° C. A solution of trans-5-cyclohexyl-pent-4-enoic acid (2R-hydroxy-1R-methyl-2-phenyl-ethyl)-methyl amide (5.20 g, 15.8 mmol, 1 equiv) in THF (30 mL) was added via cannula, and the resulting solution was stirred at −78° C. for 1 h, maintained at 0° C. for 15 min, stirred at 23° C. for 5 min and then cooled again to 0° C. 4-Fluorobenzyl bromide (2.95 mL, 23.7 mmol, 1.5 equiv) was added, and the reaction mixture was stirred at 0° C. for 30 min and then partitioned between half-saturated NH$_4$Cl (150 mL) and a 1:1 mixture of EtOAc and hexanes (2×150 mL). The combined organic layers were dried over Na$_2$SO$_4$ and concentrated. Purification of the residue by flash column chromatography (gradient elution 30–40% EtOAc in hexanes) provided trans-5-cyclohexyl-2S-(4-fluoro-benzyl)-pent-4-enoic acid (2R-hydroxy-1R-methyl-2-phenyl-ethyl)-methyl amide (6.29 g, 91%) as a viscous oil: R$_f$=0.57 (50% EtOAc in hexanes); IR (cm$^{-1}$) 3382, 1616; $^1$H NMR (CDCl$_3$, mixture of rotamers) δ 0.83–1.27 (m), 1.51–1.70 (m), 1.86–1.95 (m), 2.12–2.21 (m), 2.28–2.44 (m), 2.58 (s), 2.64–2.77 (m), 2.82 (s), 2.85–2.92 (m), 4.00–4.05 (m), 4.37–4.52 (m), 5.22–5.52 (m), 6.88–7.01 (m), 7.07–7.20 (m), 7.20–7.38 (m); Anal. (C28H36FNO$_2$●0.25 H$_2$O) C, H, N.

Preparation of Intermediate 5S-(R-Bromo-cyclohexyl-methyl)-3R-(4-fluoro-benzyl)-dihydrofuran-2-one.

N-Bromosuccinimide (2.65 g, 14.9 mmol, 1.1 equiv) was added in small portions over 5 min to a solution of trans-5-cyclohexyl-2S-(4-fluoro-benzyl)-pent-4-enoic acid (2R-hydroxy-1R-methyl-2-phenyl-ethyl)-methyl amide (6.20 g, 14.2 mmol, 1 equiv) and glacial acetic acid (3.87 mL, 70.8 mmol, 5 equiv) in 4:1 mixture of THF and H$_2$O (250 mL) at 0° C. The resulting yellow solution was stirred for 15 min at 0° C., then warmed to 23° C., and subsequently refluxed for 1 h. After cooling to 23° C., the reaction mixture was partitioned between half-saturated NaHCO$_3$ (150 mL) and a 1:1 mixture of EtOAc and hexanes (2×150 mL). The combined organic layers were dried over Na$_2$SO$_4$ and concentrated. Flash chromatographic purification of the residue (5% EtOAc in hexanes) gave 5S-(R-bromo-cyclohexyl-methyl)-3R-(4-fluoro-benzyl)-dihydrofuran-2-one (3.70 g, 71%) as a white solid: mp=72–75° C.; R$_f$=0.62 (30% EtOAc in hexanes);IR (cm$^{-1}$) 1774; $^1$H NMR (CDCl$_3$) δ 1.11–1.38 (m, 6H), 1.52–1.77 (m, 5H), 2.13–2.34 (m, 2H), 2.82 (dd, 1H, J=13.7, 8.4), 2.95–3.05 (m, 1H), 3.12 (dd, 1H, J=13.7, 4.7), 3.89 (dd, 1H, J=8.4, 3.7), 4.43–4.51 (m, 1H), 6.98–7.05 (m, 2H), 7.15–7.26 (m, 2H); Anal. (C$_{18}$H$_{22}$BrFO$_2$) C, H, N.

Preparation of Intermediate 5S-(S-Azido-cyclohexyl-methyl)-3R-(4-fluoro-benzyl)-dihydro-furan-2-one.

A suspension of sodium azide (1.30 g, 20.0 mmol, 2 equiv) and 5S-(R-bromo-cyclohexyl-methyl)-3R-(4-fluoro-benzyl)-dihydrofuran-2-one (3.70 g, 10.0 mmol, 1 equiv) in N,N-dimethylformamide (30 mL) was heated at 50° C. for 18 h. The reaction mixture was cooled to 23° C. and then partitioned between water (150 mL) and a 1:1 mixture of EtOAc and hexanes (2×150 mL). The combined organic layers were dried over Na$_2$SO$_4$, concentrated, and the residue purified by flash column chromatography (10% EtOAc in hexanes) to give 5S-(S-azido-cyclohexyl-methyl)-3R-(4-fluoro-benzyl)-dihydro-furan-2-one (1.76 g, 53%) as a colorless oil: R$_f$=0.33 (20% EtOAc in hexanes); IR (cm$^{-1}$) 2109, 1772; $^1$H NMR (CDCl$_3$) δ 1.06–1.29 (m, 6H), 1.67–1.82 (m, 5H), 2.02–2.21 (m, 2H), 2.79–2.86 (m, 1H), 2.92–2.95 (m, 1H), 3.05–3.17 (m, 2H), 4.45–4.50 (m, 1H), 6.97–7.04 (m, 2H), 7.15–7.26 (m, 2H).

Preparation of Intermediate {S-Cyclohexyl-[4R-(4-fluoro-benzyl)-5-oxo-tetrahydrofuran-2S-yl]-methyl}-carbamic Acid tert-Butyl Ester.

A suspension of 5S-(S-azido-cyclohexyl-methyl)-3R-(4-fluoro-benzyl)-dihydro-furan-2-one (1.76 g, 5.31 mmol, 1 equiv) and Pd/C (10%, 0.15 g) in CH$_3$OH (30 mL) was stirred under a hydrogen atmosphere (balloon) for 3 h. The reaction mixture was filtered through celite, concentrated, and the residue dissolved in 1,4-dioxane (30 mL). N,N-diisopropylethylamine (1.85 mL, 10.6 mmol, 2 equiv) and di-tert-butyl dicarbonate (1.74 g, 7.97 mmol, 1.5 equiv) were added sequentially, and the resulting solution was stirred at 23° C. for 1.5 h. The reaction mixture was then partitioned between water (150 mL) and a 1:1 mixture of EtOAc and hexanes (2×150 mL). The combined organic layers were dried over Na$_2$SO$_4$ and concentrated. Purification of the residue by flash column chromatography (15% EtOAc in hexanes) provided {S-cyclohexyl-[4R-(4-fluoro-benzyl)-5-oxo-tetrahydro-furan-2S-yl]-methyl}-carbamic acid tert-butyl ester (1.11 g, 52%) as a white foam: R$_f$=0.55 (30% EtOAc in hexanes); IR (cm$^{-1}$) 3338, 1766, 1699; $^1$H NMR (CDCl$_3$) δ 0.92–1.26 (m, 5H), 1.40 (s, 9H), 1.62–1.80 (m, 6H), 1.95–2.05 (m, 1H), 2.17–2.27 (m, 1H), 2.79 (dd, 1H, J=13.5, 8.6), 2.88–2.98 (m, 1H), 3.09 (dd, 1H, J=13.5, 4.5), 3.37–3.43 (m, 1H), 4.43 (d, 1H, J=10.0), 4.48–4.52 (m, 1H), 6.96–7.01 (m, 2H), 7.12–7.27 (m, 2H); Anal (C$_{21}$H$_{31}$NO$_4$) C, H, N.

Preparation of Intermediate Ethyl-3-[BOC-L-CyhexΨ[COCH$_2$]-L-(p-F)Phe-L-(Tr-Gln)]-E-Propenoate.

Lithium hydroxide (7.0 mL of a 1 M aqueous solution, 7.0 mmol, 5 equiv) was added to a solution of {S-cyclohexyl-[4R-(4-fluoro-benzyl)-5-oxo-tetrahydro-furan-2S-yl]-methyl}-carbamic acid tert-butyl ester (0.567 g, 1.40 mmol, 1 equiv) in DME (10 mL) at 23° C. The resulting suspension was stirred at 23° C. for 30 min and then partitioned between 0.5 M HCl (100 mL) and EtOAc (2×100 mL). The combined organic layers were dried over Na$_2$SO$_4$, concentrated, and the residue dissolved in CH$_2$Cl$_2$ (30 mL). 4-Methylmorpholine N-oxide (0.382 g, 2.80 mmol, 2 equiv), powdered 4 Å molecular sieves (0.60 g), and tetrapropylammonium perruthenate (0.049 g, 0.139 mmol, 0.1 equiv) were added sequentially. The resulting dark reaction mixture was stirred for 2 h at 23° C. and then filtered through celite. The filtrate was concentrated under reduced pressure to provide a brown oil which was dissolved in CH$_2$Cl$_2$ (40 mL). Crude ethyl-3-[H$_2$N-L-(Tr-Gln)]-E-propenoate●HCl (see preparation of ethyl-3-[CBZ-L-LeuΨ[COCH$_2$]-D/L-Phe-L-(Tr-Gln)]-E-propenoate, 1.68 mmol, 1.2 equiv), 1-hydroxybenzotriazole hydrate (0.284 g, 2.10 mmol, 1.5 equiv), 4-methylmorpholine (0.616 mL, 5.60 mmol, 4 equiv), and 1-(3-dimethylaminopropyl)-3-ethylcarbodiimide hydrochloride (0.403 g, 2.10 mmol, 1.5 equiv) were added sequentially, and the reaction mixture was stirred for 20 h at 23° C. and then partitioned between water (150 mL) and a 1:1 mixture of EtOAc and hexanes (2×150 mL). The combined organic layers were dried over Na$_2$SO$_4$ and concentrated. Purification of the residue by flash column chromatography (40% EtOAc in hexanes) provided ethyl-3-[BOC-L-CyhexΨ[COCH$_2$]-L-(p-F)Phe-L-(Tr-Gln)]-E-propenoate (0.379 g, 32%) as a white solid: mp=192–195° C.; R$_f$=0.50 (50% EtOAc in hexanes); IR (cm$^{-1}$) 3316, 1709, 1667; $^1$H NMR (CDCl$_3$) δ 0.98–1.12 (m, 5H), 1.29 (t, 3H, J=7.2), 1.40 (s, 9H), 1.43–1.74 (m, 6H), 1.96–2.02 (m, 1H), 2.30–2.39 (m, 2H), 2.53 (d, 1H, J=17.1), 2.61–2.88 (m, 4H), 3.00 (dd, 1H, J=17.6, 10.1), 4.01–4.06 (m, 1H), 4.17 (q, 2H, J=7.2), 4.45 (s, br, 1H), 4.80 (d, 1H, J=8.1), 5.35 (d, 1H, J=15.7), 5.90 (d, 1H, J=8.4), 6.60 (dd, 1H, J=15.7, 5.0), 6.93–7.10 (m, 4H), 7.17–7.30 (m, 16H); Anal. (C$_{51}$H$_{60}$FN$_3$O$_7$) C, H, N.

Preparation of Intermediate Ethyl-3-[CyPentylSCO-L-CyhexΨ[COCH$_2$]-L-(p-F)Phe-L-(Tr-Gln)]-E-Propenoate.

HCl (10 mL of a 4.0 M solution in 1,4-dioxane) was added to a solution of ethyl-3-[BOC-L-LeuΨ[COCH$_2$]-L-Phe-L-(Tr-Gln)]-E-propenoate (0.379 g, 0.448 mmol, 1 equiv) in 1,4-dioxane (10 mL). The reaction mixture was stirred at 23° C. for 2 h and then concentrated. The resulting oil was dissolved in CH$_2$Cl$_2$ (15 mL), cooled to 0° C., and 4-methylmorpholine (0.123 mL, 1.12 mmol, 2.5 equiv) and cyclopentyl chlorothiolformate (0.096 mL, 0.583 mmol, 1.3 equiv) were added sequentially. The reaction mixture was stirred for 30 min at 0° C. and then partitioned between water (100 mL) and a 1:1 mixture of EtOAc and hexanes (2×100 mL). The combined organic layers were dried over Na$_2$SO$_4$, concentrated, and the residue was chromatographed on silica gel (30% EtOAc in hexanes) to afford ethyl-3-[CyPentylSCO-L-CyhexΨ[COCH$_2$]-L-(p-F)Phe-L-(Tr-Gln)]-E-propenoate (0.161 g, 41%) as a white solid: mp=90–95° C.; R$_f$=0.51 (50% EtAOc in hexanes; IR (cm$^{-1}$) 3312, 1714, 1654; $^1$H NMR (CDCl$_3$) δ 0.98–1.22 (m, 6H), 1.29 (t, 3H, J=7.2), 1.56–1.70 (m, 11H), 1.98–2.08 (m, 3H), 2.29–2.37 (m, 2H), 2.51–3.30 (m, 6H), 3.58–3.65 (m, 1H), 4.17 (q, 2H, J=7.2), 4.33 (s, br, 1H), 4.45 (s, br, 1H), 5.37 (dd, 1H, J=15.7, 1.6), 5.55 (d, 1H, J=8.1), 5.99 (d, 1H, J=8.4), 6.61 (dd, 1H, J=15.7, 4.7), 6.93–7.10 (m, 4H), 7.16–7.31 (m, 16H); Anal (C$_{52}$H$_{60}$FN$_3$O$_6$S) C, H, N.

Preparation of Product Ethyl-3-(CyPentylSCO-L-CyhexΨ[COCH$_2$]-L-(p-F)Phe-L-Gln)-E-Propenoate.

Triisopropylsilane (0.10 mL) and trifluoroacetic acid (6 mL) were added sequentially to a solution of ethyl-3-[CyPentylSCO-L-CyhexΨ[COCH$_2$]-L-(p-F)Phe-L-(Tr-Gln)]-E-propenoate (0.150 g, 0.172 mmol) in CH$_2$Cl$_2$ (8 mL) producing a bright yellow solution. The reaction mixture was stirred for 20 min at 23° C., then carbon tetrachloride (4 mL) was added, and the mixture was concentrated under reduced pressure. The residue was purified by flash column chromatography (3% CH$_3$OH in CH$_2$Cl$_2$) to afford ethyl-3-(CyPentylSCO-L-CyhexΨ[COCH$_2$]-L-(p-F)Phe-L-Gln)-E-propenoate (0.069 g, 63%) as a white foam: R$_f$=0.56 (10% CH$_3$OH in CH$_2$Cl$_2$); IR (cm$^{-1}$) 3281, 1716, 1637; $^1$H NMR (DMSO-d$_6$) δ 0.93–1.14 (m, 6H), 1.21 (t, 3H, J=7.2), 1.41–1.70 (m, 13H), 1.96–2.03 (m, 4H), 2.53–2.93 (m, 5H), 3.46–3.56 (m, 1H), 3.97–4.15 (m, 3H), 4.30 (s, br, 1H), 5.41 (d, 1H, J=15.7), 6.61 (dd, 1H, J=15.7, 5.0), 6.74 (s, 1H), 7.00–7.19 (m, 5H), 8.00 (d, 1H, J=8.4), 8.28 (d, 1H, J=7.8); Anal. (C$_{33}$H$_{46}$FN$_3$O$_6$S) C, H, N.

EXAMPLE 25

Preparation of Compound 25: Ethyl-3-(CyPentylOCO-L-ValΨ[COCH$_2$]-L-(p-F)Phe-L-Gln)-E-Propenoate Preparation of Intermediate Ethyl-3-[CyPentylOCO-L-ValΨ[COCH$_2$]-L-(p-F)Phe-L-(Tr-Gln)]-E-Propenoate.

HCl (3 mL of a 4.0 M solution in 1,4-dioxane) was added to a solution of ethyl-3-[BOC-L-ValΨ[COCH$_2$]-L-(p-F)Phe-L-(Tr-Gln)]-E-propenoate (0.220 g, 0.273 mmol, 1 equiv) in 1,4-dioxane (3 mL). The reaction solution was stirred at 23° C. for 2.25 hours and then concentrated to provide crude ethyl-3-[H$_2$N-L-ValΨ[COCH$_2$]-L-(p-F)Phe-L-(Tr-Gln)]-E-propenoate●HCl which was set aside.

Cyclopentanol (0.431 mL, 4.75 mmol, 17.4 equiv) was dissolved in dry CH$_2$Cl$_2$ (25 mL). Triethylamine (0.662 mL, 4.75 mmol, 17.4 equiv) and triphosgene (0.507 g, 1.71 mmol, 6.26 equiv) were added sequentially. The reaction solution was stirred 2.5 hours to provide a stock solution of cyclopentyl chloroformate (0.19 M). A portion of this solution (2.87 mL, 0.545 mmol, 2 equiv) was added to a solution of crude ethyl-3-[H$_2$N-L-ValΨ[COCH$_2$]-L-(p-F)Phe-L-(Tr-Gln)]-E-propenoate●HCl (from above) and 4-methylmorpholine (0.120 mL, 1.09 mmol, 4 equiv) in dry CH$_2$Cl$_2$ (4 mL). The reaction mixture was stirred for 1.75 hours, then poured into water (30 mL), and extracted with CH$_2$Cl$_2$ (3×30 mL). The combined organic phases were dried over Na$_2$SO$_4$, concentrated, and the residue was chromatographed on silica gel (gradient elution 40→50% EtOAc in hexanes) to afford ethyl-3-[CyPentylOCO-L-ValΨ[COCH$_2$]-L-(p-F)Phe-L-(Tr-Gln)]-E-propenoate (0.077 g, 35%) as a colorless glass: $^1$H NMR (CDCl$_3$) δ 0.68 (d, 3H, J=6.8), 0.93 (d, 3H, J=6.8), 1.29 (t, 3H, J=7.2), 1.50–1.86 (m, 10H), 1.93–2.04 (m, 2H), 2.29–2.38 (m, 2H), 2.52 (d, 1H, J=15.9), 2.64 (dd, 1H, J=12.1, 5.6), 2.73–2.90 (m, 2H), 2.99 (dd, 1H, J=17.0, 9.8), 4.10–4.22 (m, 3H), 4.40–4.51 (m, 1H), 4.92 (d, 1H, J=8.1), 4.95–5.03 (m, 1H), 5.38 (d, 1H, J=15.9), 6.06 (d, 1H, J=8.4), 6.60 (dd, 1H, J=15.9, 4.8), 6.92–7.00 (m, 2H), 7.04–7.11 (m, 2H), 7.16–7.32 (m, 15H).

Preparation of Product Ethyl-3-(CyPentylOCO-L-ValΨ[COCH$_2$]-L-(p-F)Phe-L-Gln)-E-Propenoate.

Ethyl-3-[CyPentylOCO-L-ValΨ[COCH$_2$]-L-(p-F)Phe-L-(Tr-Gln)]-E-propenoate (0.076 g, 0.093 mmol, 1 equiv) was dissolved in dry CH$_2$Cl$_2$ (6 mL). Triisopropylsilane (0.057 mL, 0.278 mmol, 3 equiv) and trifluoroacetic acid (3 mL) were added sequentially producing a bright yellow solution. This solution was stirred for 40 minutes and then concentrated. The residue was stirred in Et$_2$O (6 mL), and the solid was collected by filtration, washed with Et$_2$O (2×3 mL), and then dried under vacuum to give ethyl-3-(CyPentylOCO-L-ValΨ[COCH$_2$]-L-(p-F)Phe-L-Gln)-E-propenoate (0.040 g, 75%) as a white solid: mp=220–222° C. (dec); R$_f$=0.16 (5% CH$_3$OH in CH$_2$Cl$_2$); IR (cm$^{-1}$) 3413, 3317, 1708, 1658; $^1$H NMR (DMSO-d$_6$) δ 0.74 (d, 3H, J=6.5), 0.82 (d, 3H, J=6.5), 1.20 (t, 3H, J=7.2), 1.38–1.84 (m, 10H), 1.96–2.12 (m, 3H), 2.46–2.84 (m, 4H), 2.88–2.97 (m, 1H), 3.82–3.89 (m, 1H), 4.09 (q, 2H, J=7.2), 4.25–4.36 (m, 1H), 4.84–4.94 (m, 1H), 5.40 (d, 1H, J=15.6), 6.61 (dd, 1H, J=15.6, 5.3), 6.73 (s, 1H), 6.98–7.24 (m, 5H), 7.30 (d, 1H, J=8.7), 7.99 (d, 1H, J=8.4); Anal. (C$_{30}$H$_{42}$FN$_3$O$_7$●0.5 H$_2$O) C, H, N.

Compounds 26 through 34, illustrated above, can be produced by the skilled artisan, using routine experimentation, in a manner analogous to the various procedures described above for producing compounds 1 through 25.

Biochemical and Biological Evaluation

Inhibition of Rhinovirus Protease

Stock solutions (50 mM, in DMSO) of various compounds were prepared; dilutions were in the same solvent. Recombinant Rhinovirus 3C proteases from serotypes 14, 16 and 2 were prepared by the following standard chromatographic procedures: (1) ion exchange using Q Sepharose Fast Flow from Pharmacia; (2) affinity chromatography using Affi-Gel Blue from Biorad; and (3) sizing using Sephadex G-100 from Pharmacia. Assays contained 2% DMSO, 50 mM tris pH 7.6, 1 mM EDTA, a compound at the indicated concentrations, approximately 1 μM substrate, and 50–100 nM protease. For K$_i$ determinations, the compound and the enzyme were preincubated for 10 minutes at 30° C. prior to addition of the substrate (substrate start). The k$_{obs/I}$ values were obtained from reactions initiated by addition of enzyme rather than substrate. RVP activity is measured in the fluorescence resonance energy transfer assay. The substrate was (N-terminal) DABCYL-(Gly-Arg-Ala-Val-Phe-Gln-Gly-Pro-Val-Gly)-EDANS. In the uncleaved peptide, the EDANS fluorescence was quenced by the proximal DABCYL moiety. When the peptide was cleaved, the quenching was relieved, and activity was measured as an increase in fluorescence signal. Data was analyzed using standard non-linear fitting programs (Enzfit), and are shown in Table 1.

TABLE 1

| COMPOUND | RVP | INHIB | k$_{obs/I}$ (M$^{-1}$sec$^{-1}$) |
|---|---|---|---|
| 1 |  | ND | 17,380 |
|  | (2) | ND | 2,242 |
|  | (16) | ND | 3,880 |
| 2 |  | ND | 47,000 |
|  | (2) | ND | 4,600 |
|  | (16) | ND | 10,410 |
| 3 |  | >7 μM(K$_i$) | 29,200 |
| 4 |  | ND | 180,000 |
|  | (2) | ND | 17,800 |
|  | (16) | ND | 34,600 |
| 5 |  | ND | 500,000 |
|  | (2) | ND | 26,900 |
|  | (16) | ND | 89,700 |
| 6 |  | ND | 87,600 |
|  | (2) | ND | 13,350 |
|  | (16) | ND | 23,230 |
| 7 |  | ND | 255,000 |
|  | (2) | ND | 25,000 |
|  | (16) | ND | 100,000 |
| 8 |  | ND | 55,700 |
|  | (2) | ND | 7,000 |
|  | (16) | ND | 14,200 |
| 1 + 9 (~1:1) |  | ND | 5,100 |
| 10 |  | ND | 440,000 |
| 11 |  | ND | 850,000 |
| 12 |  | ND | 404,000 |
| 13 |  | 1.6 | 196,000 |

TABLE 1-continued

| COMPOUND | RVP | INHIB | $k_{obs/I\ (M^{-1}sec^{-1})}$ |
|---|---|---|---|
| 14 | | 1.7 | 293,000 |
| 15 | | ND | 127,000 |
| 16 | | 3.4 | 150,000 |
| 17 | | ND | 845,000 |
| 18 | | 0.78 | 127,400 |
| 19 | | ND | 67,200 |
| 20 | | ND | 52,140 |
| 21 | | ND | 243,000 |
| 22 | | ND | 124,000 |
| 23 | | ND | 36,500 |
| 24 | | 0.67 | 240,000 |
| 25 | | ND | 16,000 |
| 26 | | ND | 34,800 |
| 27 | | 0.6 | 167,000 |
| 28 | | 0.46 | 450,000 |
| 29 | | ND | ND |
| 30 | | ND | 292,000 |
| 31 | | ND | 85,300 |
| 32 | | ND | 58,000 |
| 33 | | ND | 281,000 |
| 34 | | 0.65 | 240,000 |

In the above table, all data are for RVP serotype-14 unless otherwise noted in parentheses. All strains of human rhinovirus (HRV) were purchased from American Type Culture Collection (ATCC) except for serotype 14, which was produced from the infectious cDNA clone constructed and supplied to Applicants by Dr. Robert Rueckert at the Institute for Molecular Virology, University of Wisconsin, Madison, Wis. The column designated INHIB represents the percent inhibition at 10 minute preincubation with 50 nM RVP prior to addition of substrate. The data in the column designated $k_{obs/I}$ was measured from progress curves in enzyme start experiments. The designation ND indicates that a value was not determined for that compound.

Antirhinoviral HI-HeLa Cell Culture Assay

In the Cell protection Assay, the ability of compounds to protect cells against HRV infection was measured by the XTT dye reduction method. This method is described in Weislow, O. S., Kiser, R., Fine, D. L., Bader, J., Shoemaker, R. H., Boyd, M. R., *J. Natl. Cancer Inst.* 1989, 81, 577–586, the disclosure of which is incorporated herein by reference.

HI-HeLa cells were infected with HRV-14 at a multiplicity of infection (m.o.i.) of 0.13 (virus particles/cell) or mock-infected with medium only. Infected or mock-infected cells were resuspended at $8 \times 10^5$ cells per mL and incubated with appropriate concentrations of compounds of formula I. Two days later, XTT/PMS was added to test plates, and the amount of formazan produced was quantified spectrophotometrically at 450/650 nm. The $EC_{50}$ was calculated as the concentration of compound that increased the percentage of formazan production in compound-treated, virus infected cells to 50% of that produced by compound-free mock-infected cells. The 50% cytotoxic dose ($CC_{50}$) was calculated as the concentration of compound that decreased the percentage of formazan produced in compound-treated, mock-infected cells to 50% of that produced by compound-free mock-infected cells. The therapeutic index (TI) was calculated by dividing the $CC_{50}$ by the $EC_{50}$.

All strains of human rhinovirus (HRV) for use in this assay were purchased from American Type Culture Collection (ATCC) except for HRV serotype-14, which was produced from the infectious cDNA clone constructed and supplied to Applicants by Dr. Robert Rueckert at the Institute for Molecular Virology, University of Wisconsin, Madison, Wis. HRV stocks were propagated, and viral assays were performed in HI-HeLa cells (ATCC). Cells were grown in Minimal Essential Medium, available from Life Technologies, with 10% fetal bovine serum.

The compounds were tested against control compounds WIN 51711, WIN 52084, and WIN 54954, all obtained from Sterling-Winthrop Pharmaceuticals, and control compound Pirodavir, obtained from Janssen Pharmaceuticals. Antiviral data obtained for the test compounds are shown in Table 2 where all data are for HRV serotype-14 unless otherwise noted in parentheses.

TABLE 2

| # | HRV | $EC_{50}$ ($\mu$M) | $CC_{50}$ ($\mu$M) | TI |
|---|---|---|---|---|
| 1 | | 0.36 | >320 | >889 |
| 2 | | 0.24 | >320 | >1333 |
| | (2) | 1.8 | >320 | >178 |
| 3 | | 1.9 | 50.1 | 26 |
| 4 | | 0.10 | >320 | >3200 |
| | (2) | 0.50 | >320 | >640 |
| 5 | | 0.19 | >320 | >1730 |
| 6 | | 0.68 | >100 | >147 |
| 7 | | 0.022 | >10 | >454 |
| | (2) | 0.10 | >10 | >100 |
| | (10) | 0.035 | >10 | >286 |
| | (89) | 0.004 | >10 | >2500 |
| | (39) | 0.13 | >10 | >75 |
| 8 | | 0.19 | >100 | >526 |
| 1 + 9 (~1:1) | | 1.3 | >320 | >246 |
| | (16) | 2.8 | >320 | >114 |
| | (2) | 2.0 | >320 | >160 |
| | (10) | 4.1 | >320 | >78 |
| | (89) | 5.1 | >320 | >63 |
| 10 | | 0.011 | >1 | >91 |
| | (2) | 0.18 | >1 | >57 |
| 11 | | 0.006 | >3 | >500 |
| | (2) | 0.12 | >3 | >25 |
| | (39) | 0.13 | >3 | >23 |
| | (10) | 0.060 | >3 | >50 |
| | (16) | 0.025 | >3 | >120 |
| | (1A) | 0.16 | >3 | >18 |
| 12 | | 0.14 | >1 | >7 |
| 13 | | 0.060 | >3 | >50 |
| 14 | | 0.020 | >10 | >500 |
| | (2) | 0.13 | >10 | >76 |
| | (89) | 0.080 | >10 | >125 |
| | (16) | 0.10 | >10 | >100 |
| | (10) | 0.16 | >10 | >62 |
| | (1A) | 0.17 | >10 | >58 |
| | (39) | 0.07 | >10 | >143 |
| 15 | | 0.063 | >1 | >15 |
| 16 | | 0.050 | >3 | >60 |
| | (2) | 0.18 | >3 | >16 |
| | (39) | 0.20 | >3 | >15 |
| | (89) | 0.080 | >3 | >37 |
| | (16) | 0.10 | >3 | >30 |
| | (10) | 0.15 | >3 | >20 |
| | (1A) | 0.18 | >3 | >16 |
| 17 | | 0.027 | >10 | >370 |
| | (2) | 0.36 | >10 | >27 |
| | (39) | 0.48 | >10 | >20 |
| 18 | | 0.48 | >3 | >6 |
| 19 | | 0.28 | >3 | >10 |
| | (2) | 0.71 | >3 | >4 |
| | (10) | 1.6 | >3 | >1.8 |
| | (1A) | 0.60 | >3 | >5 |
| 20 | | 0.042 | >3 | >71 |
| | (2) | 0.56 | >3 | >5 |
| | (39) | 1.2 | >3 | >2.5 |
| | (89) | 0.47 | >3 | >6 |
| | (16) | 0.15 | >3 | >20 |
| | (10) | 0.50 | >3 | >6 |
| | (1A) | 0.53 | >3 | >5 |
| 21 | | 0.16 | >10 | >62 |
| | (2) | 1.0 | >10 | >10 |
| | (10) | 1.4 | >10 | >7 |

TABLE 2-continued

| # | HRV | EC$_{50}$ ($\mu$M) | CC$_{50}$ ($\mu$M) | TI |
|---|---|---|---|---|
|  | (1A) | 0.56 | >10 | >17 |
| 22 |  | 0.050 | >32 | >640 |
|  | (2) | 0.36 | >32 | >88 |
|  | (39) | 0.40 | >32 | >80 |
|  | (89) | 0.24 | >32 | >133 |
|  | (16) | 0.40 | >32 | >80 |
|  | (10) | 0.50 | >32 | >64 |
|  | (1A) | 0.43 | >32 | >74 |
| 23 |  | 20.9 | >10 | ND |
| 24 |  | 0.032 | >3 | >93 |
| 25 |  | 0.14 | >3 | >21 |
|  | (2) | 0.68 | >3 | >4 |
|  | (10) | 1.7 | >3 | >1.7 |
|  | (1A) | 0.90 | >3 | >3 |
|  | (16) | 0.71 | >3 | >4 |
|  | (39) | 0.56 | >3 | >5 |
|  | (89) | 0.32 | >3 | >9 |
| 26 |  | 0.050 | >10 | >200 |
|  | (1A) | 0.50 | >10 | >20 |
|  | (10) | 0.55 | >10 | >18 |
| 27 |  | 0.060 | >1 | >16 |
|  | (1A) | 1.8 | >1 | >0.5 |
|  | (10) | 3.3 | >1 | >0.3 |
| 28 |  | 0.025 | >10 | >400 |
|  | (1A) | 0.60 | >10 | >16 |
|  | (10) | 1.0 | >10 | >10 |
| 29 |  | ND | ND | ND |
| 30 |  | 1.5 | >100 | >66 |
| 31 |  | 0.16 | >3 | >18 |
|  | (1A) | 6.3 | >3 | >0.4 |
|  | (10) | 4.7 | >3 | >0.6 |
| 32 |  | 0.4 | >32 | >80 |
|  | (1A) | 2.2 | >32 | >14 |
|  | (10) | 1.9 | >32 | >16 |
| 33 |  | 0.51 | >32 | >62 |
|  | (1A) | 1.7 | >32 | >18 |
|  | (10) | 1.6 | >32 | >20 |
| 34 |  | 0.10 | >3 | >30 |
|  | (1A) | 0.30 | >3 | >10 |
|  | (10) | 0.40 | >3 | >7 |
| WIN 51711 |  | 0.78 | >60 | >77 |
| WIN 52084 |  | 0.07 | >10 | >143 |
| WIN 54954 |  | 2.13 | >63 | >30 |
| Pirodavir |  | 0.03 | >10 | >300 |

Anticoxsackieviral HI-HeLa Cell Culture Assay

The Coxsackie strain A-21 (CVA-21) was purchased from American Type Culture Collection (ATCC). Virus stocks were propagated, and antiviral assays were performed in HI-HeLa Cells (ATCC). Cells were grown in Minimal Essential Medium with 10% fetal bovine serum.

The ability of compounds to protect cells against CVA-21 infection was measured by the XTT dye reduction method. This method is described in Weislow, O. S., Kiser, R., Fine, D. L., Bader, J., Shoemaker, R. H., Boyd, M. R., *J. Natl. Cancer Inst.* 1989, 81, 577–586, the disclosure of which is incorporated herein by reference. HI-HeLa cells were infected with CVA-21 at a multiplicity of infection (m.o.i.) of 0.05 (CVA-21) or mock-infected with medium only. Infected or uninfected cells were resuspended at 4×10$^{-4}$ cells per mL and incubated with appropriate concentrations of drug. One day later, XTT/PMS was added to test plates, and the amount of formazan produced was quantified spectrophotometrically at 450/650 nm. The EC$_{50}$ was calculated as the concentration of drug that increased the percentage of formazan production in drug-treated, virus-infected cells to 50% of that produced by drug-free, uninfected cells. The 50% cytotoxic dose (CC$_{50}$) was calculated as the concentration of drug that decreased the percentage of formazan produced in drug-treated, uninfected cells to 50% of that produced in drug-free, uninfected cells. The therapeutic index (TI) was calculated by dividing the CC$_{50}$ by the EC$_{50}$.

The compounds were tested against control compound WIN 54954, obtained from Sterling-Winthrop Pharmaceuticals, and control compound Pirodavir, obtained from Janssen Pharmaceuticals. Antiviral data obtained for the test compounds against Coxsackie strain A-21 (CVA-21) are shown in Table 3.

TABLE 3

| COMPOUND # | EC$_{50}$ ($\mu$M) | CC$_{50}$ ($\mu$M) | TI |
|---|---|---|---|
| 7 | 0.16 | >10 | >63 |
| WIN 54954 | >100 | >100 |  |
| Pirodavir | >100 | >100 |  |

In describing the invention, the inventors have set forth certain theories and mechanisms in an effort to disclose how or why the invention works in the manner in which it works. These theories and mechanisms are set forth for informational purposes only. Applicants are not to be bound by any specific chemical or physical mechanisms or theories of operation.

While the invention has been described in terms of various preferred embodiments and specific examples, those skilled in the art will recognize that various changes and modifications can be made without departing from the spirit and scope of the invention, as defined in the appended claims.

We claim:

1. A compound of the formula (I):

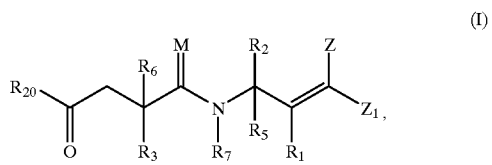

wherein:

M is O or S;

R$_1$ is H, F, an alkyl group, OH, SH, or an O-alkyl group;

R$_2$ and R$_5$ are independently selected from H,

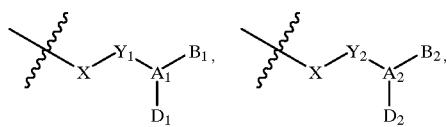

or an alkyl group, wherein said alkyl group is different from

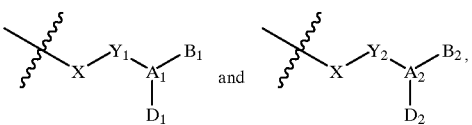

with the proviso that at least one of $R_2$ or $R_5$ must be

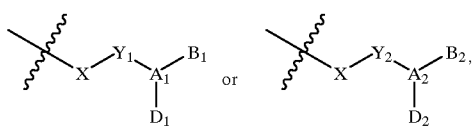

and wherein, when $R_2$ or $R_5$ is

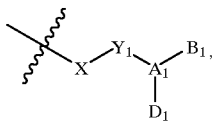

X is =CH or =CF and $Y_1$ is =CH or =CF,
or X and $Y_1$ together with Q' from a three-membered ring in which Q' is —C($R_{10}$)($R_{11}$)—or —O—, X is —CH—or —CF—, and $Y_1$ is —CH—or —CF—, or —C(alkyl)—, where $R_{10}$ and $R_{11}$ independently are H, a halogen, or an alkyl group, or, together with the carbon atom to which they are attached, form a cycloalkyl group or a heterocycloalkyl group, or X is —$CH_2$—, —$CF_2$—, —CHF—, or —S—, and $Y_1$ is —O—, —S—, $NR_{12}$—, —C($R_{13}$)($R_{14}$)—, —C(O)—, —C(S)—, or —C($CR_{13}R_{14}$)—, wherein $R_{12}$ is H or alkyl, and $R_{13}$ and $R_{14}$ independently are H, F, or an alkyl group, or, together with the atoms to which they are bonded, form a cycloalkyl group or a heterocycloalkyl group.

$A_1$ is C, CH, CF, S, P Se, N, $NR_{15}$, S(O), Se(O), P—$OR_{15}$, or P—$NR_{15}R_{16}$, wherein $R_{15}$ and $R_{16}$ independently are an alkyl group, a cycloalkyl group, a heterocycloalkyl group, an aryl group, or a heteroaryl group, or, together with the atom to which they are bonded, form a heterocycloalkyl group;

$D_1$ is a moiety with a lone pair of electrons capable of forming a hydrogen bond; and $B_1$ is H, F, an alkyl group, a cycloalkyl group, a heterocycloalkyl group, an aryl group, a heteroaryl group —$OR_{17}$, —$SR_{17}$, —$NR_{17}R_{18}$, —$NR_{19}NR_{17}R_{18}$, or —$NR_{17}OR_{18}$, wherein $R_{17}$, $R_{18}$, and $R_{19}$ independently are H, an alkyl group, a cycloalkyl group, a heterocycloalkyl group, an aryl group, a heteroaryl group, or an acyl group; and with the provisos that when $D_1$ is the moiety =N with a lone pair of electrons capable of forming a hydrogen bond, $B_1$ does not exist; and when $A_1$ is an $sp^3$ carbon, $B_1$ is not —$NR_{17}R_{18}$ when $D_1$ is the moiety. —$NR_{25}R_{26}$ with a lone pair of electrons capable of forming a hydrogen bond, wherein $R_{25}$ and $R_{26}$ are independently H, an alkyl group, a cycloalkyl group, a heterocycloalkyl group, an aryl group, or a heteroaryl group; and wherein $D_1$–$A_1$–$B_1$ optionally forms a nitro group where $A_1$ is N; and further wherein, when $R_2$ or $R_5$ is

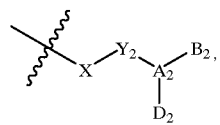

X is =CH or =CF and $Y_2$ is =C, =CH, or =CF,
or X and $Y_2$ together with Q' form a three-membered ring in which Q' is —C($R_{10}$)($R_{11}$)—or —O—, X is —CH—or —CF—, and $Y_1$ is —CH—or —CF—, or —C(alkyl)—, where $R_{10}$ and $R_{11}$ independently are H, a halogen, or an alkyl group, or, together with the carbon atom to which they are attached, form a cycloalkyl group or a heterocycloalkyl group, or X is —$CH_2$—, —$CF_2$—, —CHF—, or —S—, and $Y_2$ is —O—, —S—, N(R'$_{12}$) —, —C(O)—, —C(R'$_{13}$)(R'$_{14}$)—, —C(S)—, or —C($CR'_{13}R'_{14}$)—, wherein R'$_{12}$ is H, an alkyl group, a cycloalkyl group, a heterocycloalkyl group, an aryl group, a heteroaryl group, —OR'$_{13}$—NR'$_{13}$R'$_{14}$, —C(O)—R'$_{13}$, —$SO_2$R'$_{13}$, or —C(S)R'$_{13}$ and R'$_{14}$, independently are H, F, or an alkyl group, a cycloalkyl group, a heterocyclogroup, an aryl group, or a heteroaryl group, or, together with the atom to which they are attached, form a cycloalkyl group or a heterocycloalkyl group;

$A_2$ is C, CH, CH, S, P, Se, N, $NR_{15}$, S(O), Se(O), P—$NR_{15}R_{16}$, wherein $R_{15}$ and $R_{16}$ independently are an alkyl group, a cycloalkyl group, a heterocycloalkyl group, an aryl group, or a heteroaryl group or together with the atom to which they are bonded, form a heterocycloalkyl group;

$D_2$ is a moiety with a lone pair of electrons capable of forming a hydrogen bond; and $B_2$ is H, F, an alkyl group, a cycloalkyl group, a heterocycloalkyl group, an aryl group, a heteroaryl group, —$OR_{17}$, —$SR_{17}$, —$NR_{17}R_{18}$, —$NR_{19}NR_{17}R_{18}$, or —$NR_{17}OR_{18}$, wherein $R_{17}$, $R_{18}$, and $R_{19}$ independently are H, an alkyl group, a cycloalkyl group, a heterocycloalkyl group, an aryl group, a heteroaryl group, a cycloalkyl group; and further wherein any combination of $Y_2$, $A_2$, $B_2$, and $D_2$ optionally can form a cycloalkyl group, a heterocycloalkyl group, an aryl group, or a heteroaryl group;

$R_3$ and $R_6$ are independently H, F, an alkyl group, a cycloalkyl group, a heterocycloalkyl group, an aryl group, a heteroaryl group, —C(O)$R_{17}$, —$OR_{17}$, —$SR_{17}$, —$NR_{17}R_{18}$, —$NR_{19}NR_{17}R_{18}$, or —$NR_{17}OR_{18}$ provided that $R_3$ and $R_6$ cannot both be H, wherein $R_{17}$, and $R_{18}$, and $R_{19}$ independently are H, an alkyl group, a cycloalkyl group, a heterocycloalkyl group, an aryl group, a heteroaryl group, or an acyl group; or, $R_3$ and $R_6$, together with the carbon atom to which they are attached, form a cycloalkyl group or a heterocycloalkyl group;

$R_7$ is H, an alkyl group, a cycloalkyl group, a heterocycloalkyl group, as aryl group, a heteroaryl group, —$OR_{17}$, —$SR_{17}$, —$NR_{17}R_{18}$, —$NR_{19}NR_{17}R_{18}$, or —$NR_{17}OR_{18}$, wherein $R_1$, $R_{18}$, and $R_{19}$ independently are H, an alkyl group, a cycloalkyl group, a heterocycloalkyl group, an aryl group, a heteroaryl group, or an acyl group;

or $R_7$, together with $R_3$ or $R_6$ and the atoms to which they are attached, forms a heterocycloalkyl group;

81

$R_{20}$ is H, OH, or any suitable organic moiety; and

Z is H, F, an alkyl, a cycloalkyl group, a heterocycloalkyl group, an aryl group, a heteroaryl group, $-C(O)R_{21}$, $-CN$, $-C(O)NR_{21}$, $R_{22}$, $-C(O)NR_{21}OR_{22}$, $-C(S)NR_{21}$, $-C(S)NR_{21}R_{22}$, $-NO_2$, $-SOR_2$, $-SO_2R_2$, $-SO_2NR_{21}R_{22}$, $-SO(NR_{21})(OR_{22})$, $-SONR_{21}$, $-SO_3R_{21}$, $-PO(OR_{21})_2$, $-PO(R_{21})(R_{22})$, $-PO(NR_{21}R_{22})(OR_{23})$, $PO(NR_{21}R_{22})(NR_{23}R_{24})$, $-C(O)NR_{21}NR_{22}R_{23}$, or $-C(S)NR_{21}NR_{22}R_{23}$, wherein $R_{21}$, $R_{22}$, $R_{23}$, and $R_{24}$ are independently H, an alkyl group, a cycloalkyl group, a heterocycloalkyl group, an aryl group, a heteroaryl group, an acyl group, or a thioacyl group, or wherein any two of $R_{21}$, $R_{22}$, $R_{23}$, and $R_{24}$, together with the atom(s) to which they are bonded, form a heterocycloalkyl group;

$Z_1$ is $-CO_2R_{21}$, wherein $R_{21}$ is an alkyl group, a cycloalkyl group, a heterocycloalkyl group, an aryl group, a heteroaryl group, an acyl group, or a thioacyl group;

or a pharmaceutically acceptable prodrug, salt, active metabolite, or solvate thereof; and wherein said compound, or pharmaceutically acceptable prodrug, salt, active metabolite, or solvate thereof, has antipicornaviral activity with an $EC_{50}$ less than or equal to 10 μM in the HI—HeLa cell culture assay.

2. A compound of claim 1, wherein $R_1$ is H or F, or a pharmaceutically acceptable prodrug, salt, active metabolite, or solvate thereof.

3. A compound of claim 1, wherein $R_{20}$ is H, an alkyl group, a cycloalkyl group, a heterocycloalkyl group, an aryl group, a heteroaryl group, $-OR_{17}$, $-SR_{17}$, $-NR_{17}R_{18}$, $-NR_{19}NR_{17}R_{18}$, or $-NR_{17}OR_{18}$, wherein $R_{17}$, $R_{18}$, and $R_{19}$ independently are H, an alkyl group, a cycloalkyl group, a heterocycloalkyl group, an aryl group, a heteroaryl group, or an aryl group, or a pharmaceutically acceptable prodrug, salt, active metabolite, or solvent wherein.

4. A compound of claim 3, wherein $R_{20}$ is the alkyl group $-C(R_{41})(R_{42})NR_{43}R_{44}$, wherein:

$R_{41}$ and $R_{42}$ independently are H, an alkyl group, a cycloalkyl group, a heterocycloalkyl group, an aryl group, or a heteroaryl group; and $R_{43}$ is H, an alkyl group, a cycloalkyl group, a heterocycloalkyl group, an aryl group, a heteroaryl group, $-NR_{45}R_{46}$, $-C(O)r_{45}$, $-C(S)r_{45}$, $-C(O)NR_{45}R_{46}$, $-C(S)NR_{45}R_{46}$, $-C(O)NR_{45}OR_{46}$, $-C(S)NR_{45}OR_{46}$, $-C(O)SR_{45}$, $-C(O)NR_{45}$, $-C(S)OR_{45}$, $-C(S)SR_{45}$, $-OR_{45}$, $-SR_{45}$, $-C(O)NR_{45}R_{47}$, $-C(S)NR_{45}NR_{46}R_{47}$, $-SOR_{45}$—$SO_2R_{45}$, $-S(O)NR_{45}R_{46}$, $-S(O)NR_{45}(OR_{46})$, $-SO_2NR_{45}R_{46}$, $-SO_2NR_{45}(OR_{46})$, or $-SO_3R_{45}$, wherein $R_{45}$, $R_{46}$, and $R_{47}$ independently are H, an alkyl group, a cycloalkyl group, a heterocycloalkyl group, an aryl group, or a heteroaryl group, $R_{44}$ is H, an alkyl group, a cycloalkyl group, an aryl group, $-NR_{45}R_{46}$, $-C(O)R_{45}$, $-C(S)R_{45}$, $-C(O)NR_{45}R_{46}$, $-C(S)NR_{45}R_{46}$, $-C(S)NR_{45}OR_{46}$, $-C(O)SR_{45}$, $-C(O)OR_{45}$, $-C(S)OR_{45}$, $-C(S)SR_{45}$, $-OR_{45}$, $-SR_{45}$, $-C(O)NR_{45}NR_{46}R_{47}$, $-C(S)NR_{45}NR_{46}R_{47}$, $-SOR_{45}$, $-SO_2R_{45}$, $-S(O)NR_{45}R_{46}$, $-S(O)NR_{45}(OR_{46})$, $-SO_2NR_{45}R_{46}$, $-SO_2NR_{45}(OR_{46})$, or $-SO_3R_{45}$, wherein $R_{45}$, $R_{46}$, $R_{47}$ independently are H, an alkyl group, a cycloalkyl group, or an aryl group, or wherein any suitable combination of $R_{41}$, $R_{42}$, $R_{43}$, and $R_{44}$ together form a cycloalkyl group;

or a pharmaceutically acceptable prodrug, salt, active metabolite, or solvate thereof.

82

5. A compound of claim 4, wherein $R_{43}$ is $-C(O)SR_{45}$ or $-C(O)OR_{45}$, or a pharmaceutically acceptable prodrug, salt, active metabolite, or solvate thereof.

6. A compound of claim 5, wherein $R_{45}$ is an alkyl group, a cycloalkyl group, an aryl group, a heterocycloalkyl group, or a heteroaryl group, or a pharmaceutically acceptable prodrug, salt, active metabolite, or solvate thereof.

7. A compound of claim 6, wherein $R_{45}$ is a $C_1$–$C_{10}$ alkyl group or a cycloalkyl group, or a pharmaceutically acceptable prodrug, salt, active metabolite, or solvate thereof.

8. A compound of claim 1, wherein at least one of $R_2$ or $R_5$

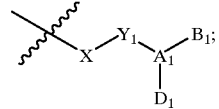

or a pharmaceutically acceptable prodrug, salt, active metabolite, or solvate thereof.

9. A compound according to claim 8, wherein $D_1$ is $-OR_{25}$, $=O$, $=S$, $=N$, $=NR_{25}$, or $-NR_{25}R_{26}$, wherein $R_{25}$ and $R_{26}$ are independently H, an alkyl group, a cycloalkyl group, a heterocycloalkyl group, an aryl group, or a heteroaryl group, or together with the nitrogen atom to which they are bonded, form a heterocycloalkyl group; or a pharmaceutically acceptable prodrug, salt, active metabolite, or solvate thereof.

10. A compound according to claim 9, wherein $D_1$ is $=O$, or a pharmaceutically acceptable prodrug, salt, active metabolite, or solvate thereof.

11. A compound according to claim 8, wherein $A_1$ is C, CH, S, or S(O); or a pharmaceutically acceptable prodrug, salt, active metabolite, or solvate thereof.

12. A compound according to claim 11, wherein $A_1$ is C; or a pharmaceutically acceptable prodrug, salt, active metabolite, or solvate thereof.

13. A compound according to claim 8, wherein $B_1$ is $NR_{17}R_{18}$, wherein $R_{17}$ and $R_{18}$ are independently H, an alkyl group, a cycloalkyl group, a heterocycloalkyl group, an aryl group, a heteroaryl group, or an acyl group; or a pharmaceutically acceptable prodrug, salt, active metabolite, or solvate thereof.

14. A compound according to claim 1, wherein at least one of $R_2$ or $R_5$ is

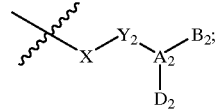

or a pharmaceutically acceptable prodrug, salt, active metabolite, or solvate thereof.

15. A compound according to claim 14, wherein $D_2$ is $-OR_{25}$, $=O$, $=S$, $=N$, $=NR_{25}$, or $-NR_{25}R_{26}$, wherein $R_{25}$ and $R_{26}$ are independently H, an alkyl group, a cycloalkyl group, a heterocycloalkyl group, an aryl group, or a heteroaryl group, or, together with the atom(s) to which they are bonded, form a heterocycloalkyl group; or a pharmaceutically acceptable prodrug, salt, active metabolite, or solvate thereof.

16. A compound according to claim 15, wherein $D_2$ is $=O$; or a pharmaceutically acceptable prodrug, salt, active metabolite, or solvate thereof.

17. A compound according to claim 14, wherein $A_2$ is C, CH, S, or S(O); or a pharmaceutically acceptable prodrug, salt, active metabolite, or solvate thereof.

18. A compound according to claim 17, wherein $A_2$ is C; or a pharmaceutically acceptable prodrug, salt, active metabolite, or solvate thereof.

19. A compound according to claim 14, wherein $B_2$ is —$NR_{17}R_{18}$, wherein $R_{17}$ and $R_{18}$ are independently H, an alkyl group, a cycloalkyl group, a heterocycloalkyl group, an aryl group, a heteroaryl group, or an acyl group; or a pharmaceutically acceptable prodrug, salt, active metabolite, or solvate thereof.

20. A compound according to claim 1, wherein $A_1$ is C, CH, S, or S(O) or wherein $A_2$ is C, CH, S, or S(O); or a pharmaceutically acceptable prodrug, salt, active metabolite, or solvate thereof.

21. A compound according to claim 1, wherein Z is independently H, an aryl group, or a heteroaryl group, —$C(O)R_{21}$, —$CO_2R_{21}$, —CN, $C(O)NR_{21}R_{22}$, —$C(O)NR_{21}OR_{22}$, —$C(S)R_{21}$, —$C(S)NR_{21}R_{22}$, —$NO_2$, —$SOR_{21}$, —$SO_2R_{21}$, —$SO_2NR_{21}R_{22}$, —$SO(NR_{21})(OR_{22})$, —$SONR_{21}$, —$SO_3R_{21}$, —$C(O)NR_{21}NR_{22}R_{23}$;

wherein $R_{21}$, $R_{22}$, $R_{23}$ are independently H, an alkyl group, a cycloalkyl group, a heterocycloalkyl group, an aryl group, a heteroaryl group, an acyl group, or a thioacyl group, or wherein any two of $R_{21}$, $R_{22}$, $R_{23}$, together with the atom(s) to which they are bonded, form a heterocycloalkyl group;

and $Z_1$ is —$CO_2R_{21}$ is an alkyl group, a cycloalkyl group, a heterocycloalkyl grouop, an aryl group, a heteroaryl group, an acyl group, or a thioacyl grouop;

or a pharmaceutically acceptable prodrug, salt, active metabolite, or solvate thereof.

22. A compound according to claim 1, wherein M is O.

23. A compound having the formula X:

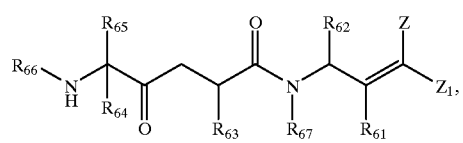
(X)

wherein:

$R_{61}$ is H, F, or an alkyl group;

$R_{62}$ is selected from one of the following moieties:

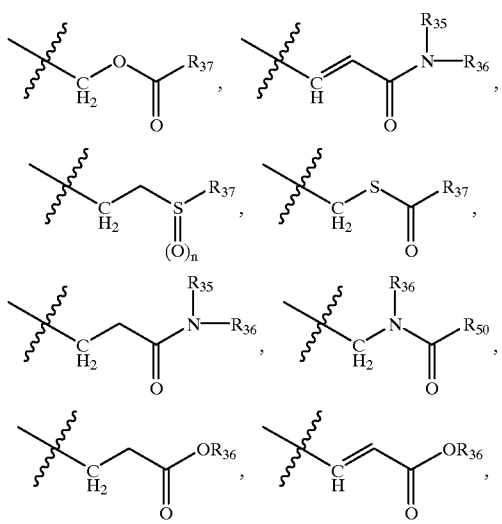

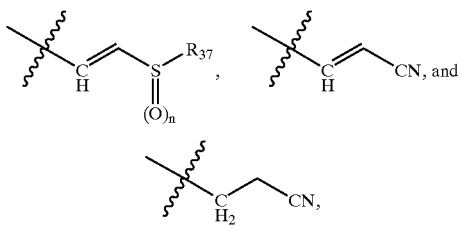

wherein:

$R_{35}$ is H, an alkyl group, an aryl group, —$OR_{38}$, or —$NR_{38}R_{39}$, wherein $R_{38}$ and $R_{39}$ independently are H, an alkyl group, a cycloalkyl group, a heterocycloalkyl group, an aryl group, a heteroaryl group, or an acyl group; and $R_{36}$ is H or an alkyl group, or $R_{35}$ $R_{36}$, together with the nitrogen atom to which they are attached, form a heterocycloalkyl group or a heteroaryl group;

$R_{37}$ is an alkyl group, an aryl group, or —$NR_{38}R_{39}$, wherein $R_{38}$ and $R_{39}$ are as defined above;

$R_{50}$ is H, an alkyl group, an aryl group, —$OR_{38}$, —$SR_{39}$, —$NR_{38}R_{39}$, —$NR_{40}NR_{38}R_{39}$, or —$NR_{38}OR_{39}$, or $R_{50}$ and $R_{36}$, together with the atoms to which they are attached, form a heterocycloalkyl group, wherein $R_{38}$ and $R_{39}$ are as defined above, and $R_{40}$ is H, an alkyl group, a cycloalkyl group, a heterocycloalkyl group, an aryl group, a heteroaryl group, or an acyl grouop; and n is 0, 1, or 2;

$R_{63}$ is an alkyl group;

$R_{64}$ is H, an alkyl group, a cycloalkyl group, a heterocycloalkyl group, an aryl group, or a heteroaryl group;

$R_{65}$ is H or an alkyl group;

$R_{66}$ is H, an acyl group, an alkyl group, a cycloalkyl group, a heterocycloalkyl group, an aryl group, a sulfonyl group, or a heteroaryl group;

$R_{67}$ is H or an alkyl grouop; and

Z is H, F, an alkyl group, a cycloalkyl group, a heterocycloalkyl group, an aryl group, a heteroaryl group, —$C(O)R_{21}$, —$CO_2R_{21}$, —CN, —$C(O)NR_{21}R_{22}$, —$C(O)NR_{21}OR_{22}$, —$C(S)R_{21}$—$C(S)NR_{21}R_{22}$, —$NO_2$, —$SOR_{21}$, —$SO_2R_{21}$, —$SO_2NR_{21}R_{22}$, —SO($NR_{21}$)($OR_{22}$), —$SONR_{21}$, $SO_3r_{21}$, —$PO(OR_{21})_2$, —$PO(R_{21})(R_{22})$, —$PO(NR_{21}R_{22})(OR_{23})$, —PO($NR_{21}R_{24}$), —$C(O)NR_{21}NR_{22}R_{23}$, or —$C(S)NR_{21}NR_{22}R_{23}$, wherein $R_{21}$, $R_{22}$, $R_{23}$, and $R_{24}$ are independently H, an alkyl group, a cycloalkyl group, a heterocycloalkyl group, an aryl group, a heteroaryl group, an acyl group, or a thioacyl group, or wherein any two of $R_{21}$, $R_{22}$, $R_{23}$, $R_{24}$, together with the atom(s) to which they are bonded, form a heterocycloalkyl group, $Z_1$ is —$CO_2R_{21}$, wherein $R_{21}$ is an alkyl group, a cycloalkyl group, a heterocycloalkyl group, an aryl group, a heteroaryl group, an acyl group, or a thioacyl group; or a pharmaceutically acceptable prodrug, salt, active metabolite, or solvate thereof.

24. A compound according to claim 23, wherein $R_{66}$ is the acyl group —$C(O)OR_{68}$ or the acyl group —$C(O)SR_{68}$, wherein $R_{68}$ is an alkyl group, a cycloalkyl group, an aryl group, a heterocycloalkyl group, or a heteroaryl group, or a pharmaceutically acceptable prodrug, salt, active metabolite, or solvate thereof.

25. A compound according to claim 4, having the formula II:

$$\text{(II)}$$

R_{44}-N(R_{43})-C(R_{42})(R_{41})-C(O)-C(R_6)(R_3)-CH_2-C(O)-N(R_7)-C(R_5)(R_2)-C(R_1)=C(Z)(Z_1)

wherein $R_1$, $R_5$, $R_6$, $R_{42}$, $R_{43}$, and $Z$ are H, $R_2$ is $CH_2CH_2C(O)NH_2$, and $R_3$, $R_{41}$, $Z_1$, and $R_{44}$ are selected from one of the following groups:

$R_3$ is $CH_2Ph$, $R_{41}$ is $CH_2CH(CH_3)_2$, $Z_1$ is $CO_2CH_2CH_3$, and $R_{44}$ is $R_{44}$ is benzyl-O-C(O)-;

$R_3$ is $CH_2Ph$, $R_{41}$ is $CH_2CH(CH_3)_2$, $Z_1$ is $CO_2CH_2CH_3$, and $R_{44}$ is $R_{44}$ is $CH_3CH_2S$-C(O)-;

$R_3$ is $CH_2Ph$, $R_{41}$ is $CH_2CH(CH_3)_2$, $Z_1$ is $Z_1$ is C(O)-indoline, and $R_{44}$ is $R_{44}$ is benzyl-S-C(O)-;

$R_3$ is $CH_2Ph$, $R_{41}$ is $CH_2CH(CH_3)_2$, $Z_1$ is $CO_2CH_2CH_3$, and $R_{44}$ is $R_{44}$ is $CH_3CH_2S$-C(O)-;

$R_3$ is $CH_2Ph$, $R_{41}$ is $CH_2CH(CH_3)_2$, $Z_1$ is $CO_2CH_2CH_3$, and $R_{44}$ is $R_{44}$ is benzyl-S-C(O)-;

$R_3$ is $CH_2Ph$, $R_{41}$ is $CH_2CH(CH_3)_2$, $Z_1$ is $CO_2CH_2CH_3$, and $R_{44}$ is $R_{44}$ is benzyl-S-C(O)-;

$R_3$ is $CH_2Ph$, $R_{41}$ is $CH_2CH(CH_3)_2$, $Z_1$ is $CO_2CH_2CH_3$, and $R_{44}$ is $R_{44}$ is cyclopentyl-S-C(O)-;

$R_3$ is $CH_2Ph$, $R_{41}$ is $CH_2CH(CH_3)_2$, $Z_1$ is $CO_2CH_2CH_3$, and $R_{44}$ is $R_{44}$ is cyclopentyl-S-C(O)-;

$R_3$ is $CH_2Ph$, $R_{41}$ is $CH_2CH(CH_3)_2$, $Z_1$ is $CO_2CH_2CH_3$, and $R_{44}$ is $R_{44}$ is $CH_3CH_2S$-C(O)-;

and $R_3$ is $CH_2Ph$, $R_{41}$ is $CH_2CH(CH_3)_2$, $Z_1$ is $CO_2CH_2CH_3$, and $R_{44}$ is $R_{44}$ is cyclopentyl-S-C(O)-;

or a pharmaceutically acceptable prodrug, salt, active metabolite, or solvate thereof.

26. A compound according to claim 4, having the formula III:

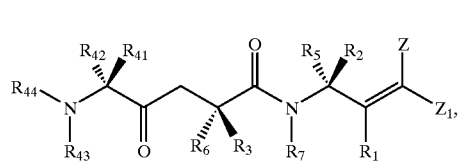

(III)

wherein $R_1$, $R_5$, $R_6$, $R_{42}$, $R_{43}$, and Z are H, $R_2$ is $CH_2CH_2C(O)NH_2$, $R_{41}$ is $CH_2CH(CH_2)_2 Z_1$ is $CO_2CH_2CH_3$, and $R_{44}$ is

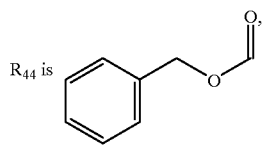

or a pharmaceutically acceptable prodrug, salt, active metabolite, or solvate thereof.

27. A compound of formula (IV):

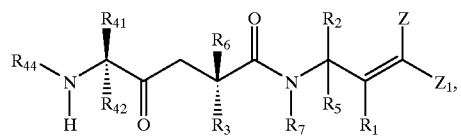

(IV)

wherein
$R_1$, $R_5$, $R_6$, $R_7$, and $R_{42}$ are H, $R_2$ is $CH_2CH_2C(O)NH_2$, and $R_3$, Z, $Z_1$, $R_{41}$, and $R_{44}$ are selected from one of the following groups:

$R_3$ is $CH_2(p-CH_3)Ph$, Z is H, $Z_1$ is $CO_2CH_2CH_3$, $R_{41}$ is $CH_2Ph$, and $R_{44}$ is

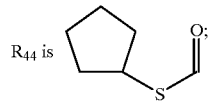

$R_3$ is $CH_2(p-CH_3)Ph$, Z is H, $Z_1$ is $CO_2CH_2CH_3$, $R_{41}$ is $CH_2Ph$, and $R_{44}$ is

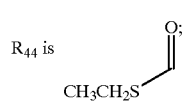

$R_3$ is $CH_2(p-CH_3)Ph$, Z is H, $Z_1$ is $CO_2CH_2CH_3$, $R_{41}$ is $CH_2Ph$, and $R_{44}$ is

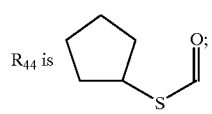

$R_3$ is $CH_2(p-CH_3)Ph$, Z is H, $Z_1$ is $CO_2CH_2CH_3$, $R_{41}$ is $CH_2Ph$, and $R_{44}$ is

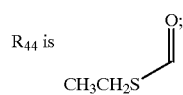

$R_3$ is $CH_2(p-CH_3)Ph$, Z is H, $Z_1$ is $CO_2CH_2CH_3$, $R_{41}$ is $CH_2Ph$, and $R_{44}$ is

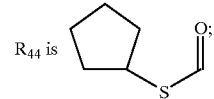

$R_3$ is $CH_2(p-CH_3)Ph$, Z is H, $Z_1$ together from

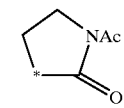

(where * indicates the point of attachment and the carbonyl group is cis to the $R_1$ group), $R_{41}$ is $CH(CH_3)_2$, and $R_{44}$ is

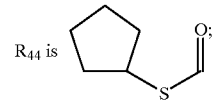

$R_3$ is $CH_2(p-F)Ph$, Z is H, $Z_1$ is $CO_2CH_2CH_3$, $R_{41}$ is $CH_2Ph$, and $R_{44}$ is

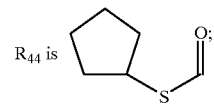

$R_3$ is $CH_2(p-F)Ph$, Z is H, $Z_1$ is $CO_2CH_2CH_3$, $R_{41}$ is $CH_2CH(CH_3)_2$, and $R_{44}$ is

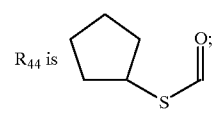

$R_3$ is $CH_2(p-CH_3)Ph$, Z is H, $Z_1$ is $CO_2CH_2CH_3$, $R_{41}$ is $CH(CH_3)_2$ and $R_{44}$ is

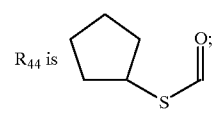

$R_3$ is $CH_2(p-CH_3)Ph$, Z is H, $Z_1$ is $CO_2CH_2CH_3$, $R_{41}$ is $CH_2CH(CH_3)_2$, and $R_{44}$ is $R_{44}$ is 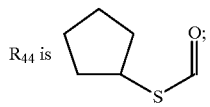

$R_3$ is $CH_2Ph$, Z is H, $Z_1$ is $CO_2CH_2CH_3$, $R_{41}$ is $CH(CH_3)_2$, and $R_{44}$ is 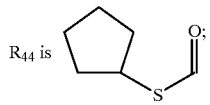

$R_3$ is $CH_2(p\text{---}CH_3)Ph$, Z is H, $Z_1$ is $CO_2CH_2CH_3$, $R_{41}$ is $CH(CH_3)_2$, and $R_{44}$ is 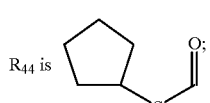

$R_3$ is $CH_2(p\text{-}F)Ph$, Z is H, $Z_1$ is $CO_2CH_2CH_3$, $R_{41}$ is cyclohexyl, and $R_{44}$ is 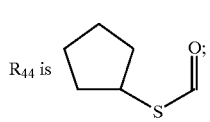

$R_3$ is $CH_2(p\text{---}F)Ph$, Z is H, $Z_1$ is $CO_2CH_2CH_3$, $R_{41}$ is cyclohexyl, and $R_{44}$ is 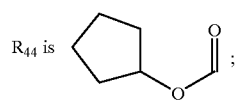

$R_3$ is $CH_2(p\text{---}F)Ph$, Z is H, $Z_1$ is $CO_2CH_2CH_3$, $R_{41}$ is $CH_2CH(CH_3)_2$, and $R_{44}$ is 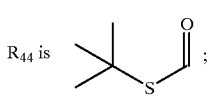

$R_3$ is $CH_2(p\text{---}F)Ph$, Z is H, $Z_1$ is $CO_2CH_2CH_3$, $R_{41}$ is $CH_2CH(CH_3)_2$, and $R_{44}$ is 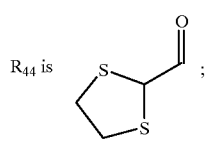

$R_3$ is $CH_2(p\text{---}F)Ph$, Z is H, $Z_1$ is 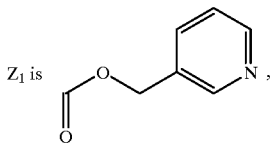

$R_{41}$ is $CH(CH_3)_2$, and $R_{44}$ is 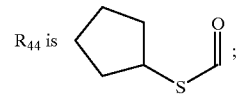

$R_3$ is $CH_2(p\text{---}F)Ph$, Z is H, $Z_1$ is 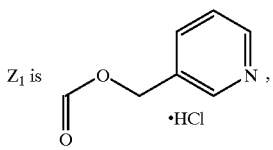

$R_{41}$ is $CH(CH_3)_2$, and $R_{44}$ is 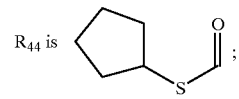

$R_3$ is $CH_2(p\text{---}F)Ph$, Z is H, $Z_1$ is 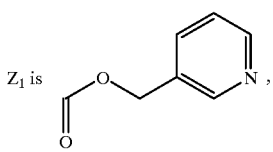

$R_{41}$ is $CH(CH_3)_2$, and $R_{44}$ is 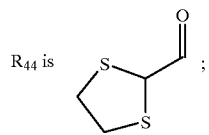

$R_3$ is $CH_2(p\text{---}F)Ph$, Z is H, $Z_1$ is $CO_2CH_2CH_3$, $R_{41}$ is $CH(CH_3)_2$ and $R_{44}$ is 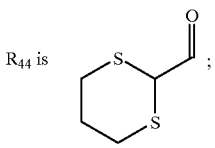

$R_3$ is $CH_2(p-F)Ph$, Z is H, $Z_1$ is

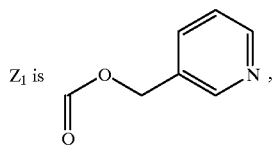

$R_{41}$ is $CH(CH_3)_2$, and $R_{44}$ is

$R_3$ is $CH_2(p-F)Ph$, Z is H, $Z_1$ is $CO_2CH_2CH_2OH$, $R_{41}$ is $CH(CH_3)_2$, and $R_{44}$ is

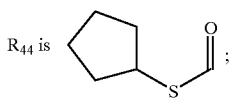

; and $R_3$ is $CH_2(p-F)Ph$, Z is H, $Z_1$ is $CO_2CH_2CH_2OH$, $R_{41}$ is $CH(CH_3)_2$, and $R_{44}$ is

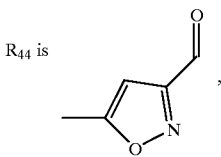

or a pharmaceutically acceptable prodrug, salt, active metalbolite, or solvate thereof.

28. A composition comprising an effective amount of at least one compound of formula II:

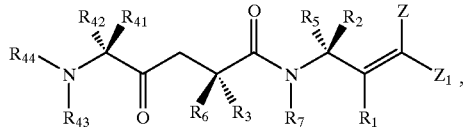

(II)

wherein $R_1$, $R_5$, $R_6$, $R_7$, $R_{42}$, $R_{43}$, and Z are H, $R_3$ is $CH_2Ph$, $R_2$ is $CH_2CH_2C(O)NH_2$, $R_{41}$ is $CH_2CH(CH_3)_2$, $Z_1$ is $CO_2CH_2CH_3$, and $R_{44}$ is

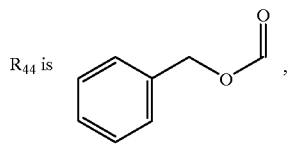

or a pharmaceutically acceptable prodrug, salt, active metalbolite, or solvate thereof. $_2C$ and at least one compound of formula III:

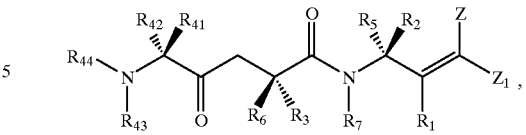

(III)

wherein $R_1$, $R_5$, $R_6$, $R_{42}$, $R_{43}$, and Z are H, $R_2$ is $CH_2CH_2C(O)NH_2$, $R_{41}$ is $CH_2CH(CH_3)_2$, $Z_1$ IS $CO_2CH_2CH_3$ and $R_{44}$ is

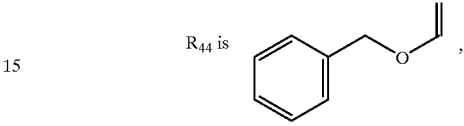

or a pharmaceutically acceptable prodrug, salt, active metalbolite, or solvate thereof.

29. A pharmaceutical composition comprising:
   (a) a therapeutically effective amount of at least one compound as defined in claim 1 or a pharmaceutically acceptable prodrug, salt, active metabolite, or solvate thereof; and
   (b) a pharmaceutically acceptable carrier, diluent, vehicle, or excipient.

30. A method of treating a mammalian disease condition mediated by picornaviral protease activity, comprising: administering to a mammal in need thereof a therapeutically effective amount of a least one compound as defined in claim 1 or a pharmaceutically acceptable prodrug, salt, active metabolite, or solvate thereof exhibiting antipicornaviral activity.

31. A method of inhibiting the activity of a picornaviral 3C protease, comprising: contacting the picornaviral 3C protease with an effective amount of at least one compound as defined in claim 1 or a pharmaceutically acceptable prodrug, salt, active metabolite, or solvate thereof.

32. A method of inhibiting the activity of a rhinoviral protease, comprising: contacting the rhinoviral protease with an effective amount of at least one compound as defined in claim 1 or a pharmaceutically acceptable prodrug, salt, active metabolite, or solvate thereof.

33. A compound according to claim 1, or a pharmaceutically acceptable prodrug, salt, active metabolite, or solvate thereof exhibiting antipicornaviral activity wherein said antipicornaviral activity is antirhinoviral activity.

34. A compound according to claim 1, or a pharmaceutically acceptable prodrug, salt, active metabolite, or solvate thereof, exhibiting antipicornaviral activity wherein said antipicornaviral activity is anticoxsackieviral activity.

35. A compound of claim 4, wherein $R_{44}$ is $-C(O)SR_{45}$ or $-C(O)OR_{45}$, or a pharmaceutically acceptable prodrug, salt, active metabolite, or solvate thereof.

36. A compound of claim 4, wherein both $R_{43}$ and $R_{44}$ are $-C(O)SR_{45}$ are $-C(O)OR_{45}$, or a pharmaceutically acceptable prodrug, salt, active metabolite, or solvate thereof provided that $R_{45}$ is not heterocyclic.

37. A compound of claim 35, wherein $R_{45}$ is an alkyl group, a cycloalkyl group, an aryl group, or a pharmaceutically acceptable prodrug, salt, active metabolite, or solvate thereof.

38. A compound of claim 36, wherein $R_{45}$ is an alkyl group, a cycloalkyl group, an aryl group, or a pharmaceutically acceptable prodrug, salt, active metabolite, or solvate thereof.

* * * * *